(12) United States Patent
Yang et al.

(10) Patent No.: US 10,857,158 B2
(45) Date of Patent: Dec. 8, 2020

(54) ANORDRIN COMPOSITIONS AND METHODS FOR TREATING DISEASES

(71) Applicants: Zhejiang Jiachi Development Pharmaceuticals LTD, Hangzhou (CN); Changzhou Ruiming Pharmaceutical Company, LTD, Changzhou (CN)

(72) Inventors: Jun Yang, Hangzhou (CN); Huijuan Shi, Hangzhou (CN); Wenping Xu, Hangzhou (CN)

(73) Assignees: ZHEJIANG JIACHI DEVELOPMENT PHARMACEUTICALS LTD, Hangzhou (CN); CHANGZHOU RUIMING PHARMACEUTICAL COMPANY, LTD, Changzhou (CN)

( * ) Notice: Subject to any disclaimer, the term of this patent is extended or adjusted under 35 U.S.C. 154(b) by 0 days.

(21) Appl. No.: 16/262,617

(22) Filed: Jan. 30, 2019

(65) Prior Publication Data

US 2019/0262360 A1     Aug. 29, 2019

Related U.S. Application Data

(62) Division of application No. 15/309,426, filed as application No. PCT/CN2015/077942 on Apr. 30, 2015, now Pat. No. 10,231,978.

(30) Foreign Application Priority Data

May 8, 2014   (CN) .......................... 2014 1 0192569

(51) Int. Cl.
| | |
|---|---|
| *A61K 31/569* | (2006.01) |
| *A61K 45/06* | (2006.01) |
| *A61K 31/138* | (2006.01) |
| *A61K 31/4196* | (2006.01) |
| *A61K 31/4535* | (2006.01) |

(52) U.S. Cl.
CPC .......... *A61K 31/569* (2013.01); *A61K 31/138* (2013.01); *A61K 31/4196* (2013.01); *A61K 31/4535* (2013.01); *A61K 45/06* (2013.01)

(58) Field of Classification Search
CPC ................ A61K 31/569; A61K 31/138; A61K 31/4196; A61K 31/4355; A61K 45/06
See application file for complete search history.

(56) References Cited

U.S. PATENT DOCUMENTS

| | | |
|---|---|---|
| 5,001,120 A | 3/1991 | Li et al. |
| 10,231,978 B2 | 3/2019 | Yang et al. |
| 2006/0024365 A1 | 2/2006 | Vaya et al. |
| 2017/0151263 A1 | 6/2017 | Yang et al. |

FOREIGN PATENT DOCUMENTS

| | | |
|---|---|---|
| CN | 101297970 A | 11/2008 |
| CN | 104208069 A | 12/2014 |
| JP | 2006-508061 A | 3/2006 |
| JP | 2008-505079 A | 2/2008 |
| JP | 2009536186 A | 10/2009 |
| JP | 2013532628 A | 8/2013 |
| JP | 2014508782 A | 4/2014 |
| WO | 2007129062 A1 | 11/2007 |
| WO | 2012007137 A1 | 1/2012 |
| WO | 2012125573 A2 | 9/2012 |
| WO | WO-2012/136133 A1 | 10/2012 |
| WO | 2012125573 A3 | 12/2012 |
| WO | WO-2015/169173 A1 | 11/2015 |

OTHER PUBLICATIONS

Alexanderson, P. et al. (2001). "Ipriflavone in the Treatment of Postmenopausal Osteoporosis a Randomized Controlled Trial," *JAMA.* 285(11): 1482-8.
Banik, U.K. et al. (Dec. 1962). "Effect of Steroidal Anti-Progestins on Implantation of Fertilized Eggs of Rats and Mice," *Proc. Soc. Expt. Biol. Med.* 111(3): 595-597.
Barrett-Connor, E. et al. (Jul. 13, 2006). "Effects of Raloxifene on Cardiovascular Events and Breast Cancer in Postmenopausal Women," *N Engl. J. Med.* 355 (2):125-137.
Barry, W.T. et al. (2005). "Significance Analysis of Functional Categories in Gene Expression Studies: A Structured Permutation Approach," *Bioinformatics* 21(9):1943-1949.
Bigarella, C.L. et al (2009; e-pub Mar. 4, 2009). "ARHGAP21 Modulates FAK Activity and Impairs Glioblastoma Cell Migration," *Biochim Biophys Acta.* 1793(5):806-16.
Boonyaratanakornkit, V. (2011). "Scaffolding Proteins Mediating Membrane-Initiated Extra-Nuclear Actions of Estrogen Receptor," *Steriods.* 76(9): 877-884.
Bussemaker, H J et al. (Sep. 27, 2007). "Dissecting Complex Transcriptional Responses Using Pathway-Level Scores Based on Prior Information," *BMC Bioinformatics* 8(Suppl. 6):S6, 7 pages.
Butler, W.B. et al. (Jan. 1981). "Effects of Serum and Insulin on the Sensitivity of the Human Breast Cancer Cell Line MCF-7 to Estrogen and Antiestrogens," *Cancer Res.* 41(1):82-88.
Cabodi, S. et al. (Mar. 15, 2004). "p130Cas Interacts With Estrogen Receptor α and Modulates Non-Genomic Estrogen Signaling in Breast Cancer Cells," *J Cell Sci.* 117(Pt. 8): 1603-11.
Cesarone, G, et al.(2006). "RNAi-Mediated Silencing of Insulin Receptor Substrate 1 (IRS-1) Enhances Tamoxifen-Induced Cell Death in MCF-7 Breast Cancer Cells," *J Cell Biochem.* 98(2): 440-450.
Cuesta, P.G. et al. "17β-estradiol Activates Glucose uptake via GLUT4 Translocation and P13K/Akt Signaling Pathway in MCF-7 Cells," *Endocrinology* 1-11.

(Continued)

*Primary Examiner* — Alicia L Otton
(74) *Attorney, Agent, or Firm* — Morrison & Foerster LLP

(57) ABSTRACT

The present invention provides methods and compositions for treating cancer, reducing side effects, and reducing postmenopausal symptoms comprising anordrin or analog thereof (such as anordrin) alone or in combination with at least one other agent selected from the group consisting of tamoxifen, raloxifene or functional equivalent thereof, and an aromatase inhibitor.

13 Claims, 38 Drawing Sheets

(56) References Cited

OTHER PUBLICATIONS

Filardo, E.J. et al. (Oct. 1, 2000). "Estrogen-Induced Activation of Erk-1 and Erk-2 Requires the G Protein-Coupled Receptor Homolog, GPR30, and Occurs via Trans-Activation of the Epidermal Growth Factor Receptor through Release of HB-EGF," *Mol. Endocrinol.* 14(10):1649-1660.
Filardo, EJ, et al.(2006). "Distribution of GPR30, a Seven Membrane-Spanning Estrogen Receptor, in Primary Breast Cancer and Its Association With Clinicopathologic Determinants of Tumor Progression," *Clin. Cancer* 12(21):6359-1666.
Filardo, E.J. et al. (Jul. 2012). "Minireview: G Protein-Coupled Estrogen Receptor-1,GPER-1: Its Mechanism of Action and Role in Female Reproductive Cancer, Renal and Vascular Physiology," *Endocrinology* 153(7):2953-2962.
Foulstone, E.J. et al. (May 2013, e-pub Mar. 20, 2013). "Insulin-Like Growth Factor Binding Protein 2 (IGFBP-2) Promotes Growth and Survival of Breast Epithelial Cells: Novel Regulation of the Estrogen Receptor," *Endocrinology* 154(5):1780-1793.
Fukatsu, K. et al. (Sep. 2010). "Lateral Diffusion of Inositol 1,4,5-Trisphosphate Receptor Type 1 in Purkinje Cells is Regulated by Calcium and Actin Filaments," *J Neurochem.* 114(6):1720-33.
Garrido, P. et al. (2013). "17 β-Estradiol Activates Glucose Uptake via GLUT4 Translocation and PI3K/Akt Signaling Pathway in MCF-7 Cells," *Endocrinology.* 154(6):1979-89.
Garris, D.R. et al. (Feb. 2005). "Estrogenic Restoration of Functional Pancreatic Islet Cytoarchitecture in Diabetes (Db/Db) Mutant C57BL/Ksj Mice: Relationship to Estradiol Localization, Systemic Glycemia, and Persistent Hyperinsulinemia," *Cell Tissue Res.* 319(2):231-242.
Geary, N. et al. (Nov. 2001). "Deficits in E2-Dependent Control of Feeding, Weight Gain, and Cholecystokinin Satiation in ER-α Null Mice," *Endocrinology* 142(11):4751-4757.
Gorres, B.K. et al. (2011). "In Vivo Stimulation of Oestrogen Receptor α Increases Insulin-Stimulated Skeletal Muscle Glucose Uptake," *J Physiol.* 2041-2054.
Hershberger, P.A. et al. (Aug. 2009 e-pub May 19, 2009). "Estrogen Receptor Beta (Erβ) Subtype-Specific Ligands Increase Transcription, p44/p42 Mitogen Activated Protein Kinase (MAPK) Activation and Growth in Human Non-Small Cell Lung Cancer Cells 1," *J. of Steroid Biochem. & Mol. Biol.* 116(1-2):102-109.
International Preliminary report on Patentability dated Nov. 17, 2016 for PCT/CN2015/077942 filed on Apr. 30, 2015, 8 pages.
International Search Report dated Aug. 5, 2015, for PCT/CN2015/077942 filed on Apr. 30, 2015, 4 pages.
Jian, G. et al. (1994). "Comparison of anti-tumor effect of a-α-nordrin and its metabolite AF-45," *Tumor* 14(2):66-69 (Abstract Only).
Kang, L.G. et al. (Apr. 2010). "Involvement of Estrogen Receptor Variant ER-α36, Not GPR30, in Nongenomic Estrogen Signaling," *Molecular Endocrinology* 24(4):709-721.
Langer, G., et al. (Aug.-Sep. 2010; e-pub Dec. 23, 2009). "A Critical Review of Fundamental Controversies in the Field of GPR30 Research," *Steroids* 75(8-9):603-610.
Liang, X. et al. (2007). "Aromatase inhibitor having anti-tumor effect," *Foreign medicine and pharmacology abstracts* 34(2):147.
Luo, H. et al. (Apr. 2014, e-pub. Jan. 30, 2014). "GPER-Mediated Proliferation and Estradiol Production in Breast Cancer-Associated Fibroblasts," *Endocr. Relat. Cancer.* 21(2):355-369.
Lou, Liguang et al, "Induction of apoptosis of human leukemia cells by α-anordrin", CA, Chemical Abstracts Service, Columbus, Ohio, US, Database accession No. 1999:170147, 2 pages.
Lou, Lijun et al. (1999). "Induction of apoptosis by .alpha.-anordrin in adriamycin-resistant MCF-7", Henan Yike Daxue Xuebao 34(3):37-39.
Ma, Z.C. et al. (Oct. 2000). "Antiangiogenic Effect of Alpha-Anordrin In Vitro and In Vivo," *Acta Pharmacol. Sin* 21(10):939-944.

Ma, Zhongcai et al, "The inhibitory effect of α-anordrin and other drugs on the growth of Swarm rat chondrosarcoma", CA, Chemical Abstracts Service, Columbus, Ohio, US, Database accession No. 2000:183111, 3 pages.
Maglietta, R. et al. (2007, e-pub Aug. 15, 2007) "Statistical Assessment of Functional Categories of Genes Deregulated in Pathological Conditions by Using Microarray Data," *Bioinformatics* 23(16):2063-72.
Mauvais-Jarvis, F. et al. (Jun. 2013). "The Role of Estrogens in Control of Energy Balance and Glucose Homeostasis," *Endocrine Reviews* 34(3):309-338.
Mehta, R.R. et al. (Dec. 1981). "Antiestrogenic and Antifertility Actions of Anordrin, (2α, 17α-diethynyl-A-nor-5α-androstane-$2_{\beta,17\beta\text{-}diol\ 2,17\text{-}dipropionate}$)," *Steroids* 38(6):679-691.
Melchiori, A., et al. (1995). "The α3β1 Integrin Is Involved in Melanoma Cell Migration and Invasion," *Exp. Cell Res.* 219:233-242.
Morini, M. et al. (Aug. 1, 2000). "The α3β1 Integrin is Associated With Mammary Carcinoma Cell Metastasis, Invasion, and Gelatinase B (Mmp-9) Activity," *Int. J. Cancer* 87:336-342.
Muthusamy, T, et al. (2009) "Sex Steroids Deficiency Impairs Glucose Transporter 4 Expression and its Translocation Through Defective Akt Phosphorylation in Target Tissues of Adult Male Rat," *Metabolism* 58(11):1581-1592.
Nehra, R. et al. (Jun. 2010). "BCL2 and CASP8 Regulation by NF-kB Differentially Affect Mitochondrial Function and Cell Fate in Antiestrogen-Sensitive and -Resistant Breast Cancer Cells," *FASEB J.* 24(6):2040-2055.
Nilsson, B.O. et al. (Jul. 2011). "G Protein-Coupled Oestrogen Receptor 1(GPER1)/GPR30: A New Player in Cardiovascular and Metabolic Oestrogenic Signaling," *British Journal of Pharmacology.* 163(6):1131-1139.
Novak, B.A.et al. (Jan. 15, 2006). "Pathway Recognition and Augmentation by Computational Analysis of Microarray Expression Data," *Bioinformatics* 22(2):233-241.
O'Brien, J.E. et al. (Jul. 17, 2006) "Estrogen Induced Proliferation of Uterine Epithelial Cells is Independent of Estrogen Receptor a Binding to Classical Estrogen Response Elements," *J. of Biol. Chem.* 281(36):26683-26692.
Ohlsson, C. et al. (Nov. 30, 2000). "Obesity and Disturbed Lipoprotein Profile in Estrogen Receptor-α-Deficient Male Mice," *Biochem. Biophys. Res. Commun.* 278(3):640-645.
Otto, C. et al. (2008, e-pub. Jun. 19, 2008). "G Protein-Coupled Receptor 30 Localizes to the Endoplasmic Reticulum and is Not Activated by Estradiol," *Endocrinology* 149(10):4846-56.
Pedram, A. et al. (2006, e-pub. Apr. 27, 2006) "Nature of Functional Estrogen Receptors at the Plasma Membrane," *Mol. Endocrinol.* 20(9):1996-2009.
Pin, X. et al. Antitumor Action of Anordrin on Experimental Tumors. Tumor (1989) 9(5): 197-199. This is on pp. 38-40. English abstract on p. 40.
Pincus, G. et al. (1965). "Steroidal Inhibitors of a Cell-Division-Inducing System In Vitro," *Steroids* 58(SUPPL 1):193-7.
Rao, J. et al. (2011). "Advances in the Understanding of the Structure and Function of ER-A36, A Novel Variant of Human Estrogen Receptor-Alpha," *Journal of Steroid Biochemistry and Molecular Biology.* 127(Issues 3-5): 231-237.
Revankar, C.M.et al. (Mar. 11, 2005). "A Transmembrane Intracellular Estrogen Receptor Mediates Rapid Cell Signaling," *Science* 307 (Issue 5715):1625-1630.
Segal, E. et al. (Jun. 2003). "Module Networks: Identifying Regulatory Modules and Their Condition-Specific Regulators From Gene Expression Data," *Nat. Genet.* 34(2):166-179.
Segal, E. et al. (Oct. 2004, e-pub.Sep. 26, 2004) "A Module Map Showing Conditional Activity of Expression Modules in Cancer," *Nat. Genet.* 36(10):1090-1098.
Szatkowski, C. et al.(2010) "Inositol 1,4,5-Trisphosphate-Induced Ca2+ Signalling is Involved in Estradiol-Induced Breast Cancer Epithelial Cell Growth," *Mol. Cancer.*9(156):1-13.
Takamura, T. et al. (2007 e-pub May 1, 2007)"Selective Estrogen Receptor Modulator Raloxifene-Associated Aggravation of Nonalcoholic Steatohepatitis," *Internal Med.* 46(9):579-581.

(56) References Cited

OTHER PUBLICATIONS

Tian, L. et al. (Sep. 20, 2005). "Discovering Statistically Significant Pathways in Expression Profiling Studies," *Proc Nat'l Acad Sci* 102(38):13544-13549.

Wang, Q. et al. (Apr. 2009) "Abrogation of Hepatic ATP-Citrate Lyase Protects Against Fatty Liver and Ameliorates Hyperglycemia in Leptin Receptor-Deficient Mice," *Hepatology* 49(4):1166-75.

Watanabe, T. et al. (Jan. 1998) "Isolation of Estrogen-Responsive Genes with a CpG Island Library," *Mol. Cell. Biol.* 18(1):442-449.

Weng, Xiuhua et al, "Comparison of the effects of α-anordrin on androgen-dependent and independent human prostate cancer", CA, Chemical Abstracts Service, Columbus, Ohio, US, Database accession No. 2010:1411820, abstract.

Weng, Xiuhua et al, "Comparison of the different effects between two epimerides of anordrin α and β monomer on human prostatic cancer in vitro", CA, Chemical Abstracts Service, Columbus, Ohio, US, (2010), Database accession No. 2010:376254, URL: STN, XP002775209 [X] 4,7-13,15.

Westwell, A.D. et al. (Nov. 2006). "New Aromatase Inhibitors With Potential in Breast Cancer Treatment," *Drug Discovery Today* 11(21/22):1041.

White, C. et al. (Oct. 7, 2005). "The Endoplasmic Reticulum Gateway to Apoptosis by Bcl-$X_L$ Modulation of the $InsP_3R$," *Nat. Cell Biol.* 7(10):1021-8.

Written Opinion of the International Searching Authority dated Aug. 5, 2015, for PCT/CN2015/077942 filed on Apr. 30, 2015, 6 pages.

Xu, Bin et al. (1997). "α-Anordrin (AF-53, 2α, 17α-Diethynyl-A-nor-5α-androstane-2β, 17β-diol dipropionate)", *Drugs of the Future* 22(10):1073-1078.

Xu, B. et al. (1989). "Antitumor Action of Anordrin on Experimental Tumors," *Tumor* 9(12):197-199 (Translation of Abstract Only).

Zhang, J. et al. (2012). "Estrogen-Independent Effects of Er-α36 in ER-Negative Breast Cancer," *Steroids* 77(6):666-673.

Zhang, X.T.et al. (Jan. 2012). "Estrogen Receptor-α 36 Mediates Mitogenic Antiestrogen Signaling in ER-Negative Breast Cancer Cells," *PLos one.* 7(1): e30174, 12 pages.

Mehta, R.R. et al. (Jul. 1982). "Antagonism of the Actions of Estrogens, Androgens and Progesterone by Anordrin (2α,17α-diethynyl-A-nor-5α-androstane-2β, 17β-diol dipropionate)," *Steroids* 40(1):65-80.

|  |  | Column1 | Column2 | Column3 |  |
|---|---|---|---|---|---|
| $IC_{50}$ of MCF-7 for 144h (n=3) |  | Anordrin (μM) | Tamoxifen (μM) | P-value |  |
| Insulin | Plus | 5.823±0.9214 | 1.361±0.284 | 0.00437 | Row1 |
|  | Minus | 3.847±0.737 | 6.277±0.614 | 3.03659 | Row2 |
| P-value |  | 0.04285 | 0.0163 |  | Row3 |
| $IC_{50}$ of MCF-7+200nM[ANO] |  |  | 1.137±0.201 |  | Row4 |

| Drug | BRCA1 | ApoD | COX7a |
|---|---|---|---|
| ANO | -1.815046 | -1.369631 | 1.554124 |
| TAM | -2.885235 | 6.054308 | -3.183801 |
|  | 0.545574 | 0.240776 | ±0.571488 |
|  | P<0.02 | P<0.01 | P<0.01 |
| RAL | -1.580719 | 3.347769 | -3.29644 |
|  |  | ±0.248253 | ±0.641845 |
|  |  | P<0.01 | P<0.01 |

Hec1A

Ishikawa

| [Drug] μM | 0 | 2.5 | 5 | 7.5 | 10 | 12.5 |
|---|---|---|---|---|---|---|
| ANO | 7.1 | 7.1 | 6.8 | 6.2 | 5.8 | 5.3 |
| TAM | 7.1 | 7.2 | 7.1 | 7.2 | 7.4 | 7.4 |

A

B

| Compound | Exchanged Group | Activity Range |
|---|---|---|
| AF-53-08 | -NH-C10 | 1-3μM |
| AF-53-09 | -NH-C12 | 6-15μM |
| AF-53-10 | -NH-C6:1=2 | 2-4μM |

ANORDRIN COMPOSITIONS AND METHODS FOR TREATING DISEASES

CROSS REFERENCE TO RELATED APPLICATIONS

This application is a division of U.S. patent application Ser. No. 15/309,426, which adopts the international filing date of Apr. 30, 2015, now U.S. Pat. No. 10,231,978, which is the national phase application under 35 U.S.C. § 371 of International Application No. PCT/CN2015/077942, filed on Apr. 30, 2015, which claims the benefit and earlier filing date of Chinese Application No. 201410192569.2, filed on May 8, 2014, the disclosures of which are incorporated herein by reference in their entirety.

TECHNICAL FIELD

The present invention relates to methods and compositions for the treatment of cancer or other diseases comprising a combination of anordrin or analog thereof (such as anordrin), alone or in combination with another agent.

BACKGROUND

Estrogen binds to its receptors to regulate RNA transcription, stimulate cell proliferation and modulate metabolic signaling in many tissues during mammalian reproduction and development. Three genes for estrogenic binding proteins have been identified, encoding estrogen receptor (ER) α and β, and G-protein coupled estrogen receptor 1 (GPER1). ER-α and β have similar structural and functional domains, containing activation function domain 1 (AF-1), a DNA binding domain (DBD), a dimerization domain and activation function domain 2 (AF-2), which is the ligand binding domain (LBD). They both belong to the nuclear super family of ligand-dependent transcription factors and have highly conserved DBD and LBD regions (95%). They regulate RNA transcription upon ligand binding, which results in ligand-receptor complexes that can dimerize and translocate into the nucleus, where they bind to estrogen response elements (EREs) found in the promoters of estrogen-responsive genes. This type of modulation is typically referred to as the classical estrogen pathway. ER-α and β also regulate diverse biological functions through membrane-initiated estrogen signaling (MIES), associating with plasma membrane by interaction with their ligand binding domain. The detailed molecular mechanisms of signaling by membrane-associated ERs are still unclear. The modulatory effects of estrogen mediated by membrane-associated receptors on cell proliferation, matrix/migration, metabolism and glucose homeostasis have been reviewed (1, 2). Furthermore, studies on ER knockout mice indicate that ER-α is the dominant functional estrogen receptor, as compared to ER-β. Three transcription variants of ER-α, -66, -46 and -36, have been found. ER-α-36 lacks the AF-1 domain and contains a partial ligand binding domain. It has been found localized to the cell membrane and cytosol. Since ER-α-36 is restricted to modulating MIES and was found to be uniquely expressed in tamoxifen-resisted cancer cells, such as MDA-MB-231 and Hec1A, MIES modulated by membrane-associated ER is thought to be responsible for the resistance to anti-estrogen therapy found by some researchers (3,4).

Orphan G-protein coupled receptor 30 (GPER1) was found to bind E2 (17-beta estradiol, an estrogen) (5) and modulate cell proliferation, resulting in resistance to anti-estrogen therapy. However, its physiological function is still a matter of controversy among some investigators (3). GPER1 knockout mice have been shown to exhibit cardiovascular and metabolic defects, with no apparent effect on fertility (6). Thus GPER1 may be involved in the modulation of estrogen-mediated metabolic signaling.

The decreased production of estrogen in postmenopausal women leads to symptoms that may adversely affect their quality of life for decades. Hormone (estrogen) replacement therapy (HRT/ERT) has been utilized to treat these symptoms since the 1940s. Studies showing an increased risk of breast and uterine cancer, as well as thromboembolism morbidity, associated with HRT have lead to a recent decline in its usage, and postmenopausal symptoms remain a problem for many older women. Selective estrogen receptor modulators (SERMs) have been utilized as treatments to regulate estrogen signaling since the 1990s. However, the lack of a more complete understanding of the molecular mechanisms involved and interfering cross-talk between selective modulators with different estrogen receptors have made it difficult to design treatment regimens that avoid the development of drug resistance and serious side effects during clinical usage.

Tamoxifen was marketed as an antagonist of the estrogen classical pathway to treat breast cancer patients, and was also reported as an agonist of ESR-α-36, potentially leading to anti-estrogen therapy resistance while stimulating the growth of endometrial epithelium cells, resulting in endometrium cancer (7, 8). Raloxifene was marketed as an upgraded version of tamoxifen, having fewer side effects and the advantages of inhibiting cancer cell migration and preventing postmenopausal symptoms, such as osteoporosis. However, raloxifene can still cause serious side effects common to tamoxifen treatment, such as thromboembolism and non-alcohol steatohepatitis (NASH) (9,10). The detailed mechanisms responsible for the side effects caused by either raloxifene or tamoxifen are still unclear. Ipriflavone is a derivative of phytohormone, and its metabolite binds to the ER-α LBD with a lower affinity than E2, exhibiting reduced estrogenic effects. The metabolites of ipriflavone and isoflavone show comparable binding affinity and activity with ER-β as E2, and they have been utilized in some countries as a medicine to prevent osteoporosis. However, their effectiveness was not supported in at least one clinical trial (11). Moreover, potential side effects as seen with traditional HRT are still a concern to some investigators (12).

2β, 7α-diethyl-A-nor-5α-androstane-2α, 17β-diol (anordiol) was first reported as possessing anti-estrogenic activity by Pincus et al in the 1960s (13, 14). Li, R. L. esterified anordiol using propionic acid to synthesize 2α,17α-diethynyl-A-nor-5α-androstane-2β,17β-diol dipropionate (anordrin, ANO) in 1969. Anordrin was marketed as an antifertility medicine using the brand name AF-53 in China beginning in 1976. Estrogen is known to cause hormone-induced cancer, and anordrin, as an estrogen receptor antagonist, was subsequently found to inhibit malignant cell growth (15, 16, 17). As a non-prescription medicine in China, Chinese physicians used it as an anti-tumor agent for nearly a decade under legally licensed conditions. However, confusing results were reported for many patients during clinical therapy. Its clinical usage as an anti-tumor agent was stopped in 1998 after the introduction of the clinical trial law in China, and all of the relevant clinical data were never collected and studied.

The disclosures of all publications, patents, patent applications and published patent applications referred to herein are hereby incorporated herein by reference in their entirety.

BRIEF SUMMARY OF THE INVENTION

The present application in one aspect provides a method of treating a cancer in an individual comprising administering to the individual: a) an effective amount of an anordrin or analog thereof (such as anordrin); and optionally b) an effective amount of at least one other agent selected from the group consisting of tamoxifen, raloxifene or functional equivalent thereof, and an aromatase inhibitor. In some embodiments, there is provided a method of reducing side effect of at least one other agent by anordrin or analog thereof (such as anordrin), comprising administering to the individual an effective amount of anordrin or analog thereof (such as anordrin) in combination with the other agent, wherein the other agent is selected from the group consisting of tamoxifen, raloxifene or functional equivalent thereof, and an aromatase inhibitor. In some embodiments, the other agent is tamoxifen. In some embodiments, the other agent is raloxifene or functional equivalent thereof (such as raloxifene, lasofoxifene or bazedoxifene). In some embodiments, the other agent is an aromatase inhibitor, such as anastrozole. In some embodiments, the side effects of at least one other agent comprise elevated sugar uptake, decreased cellular ATP concentrations, or both. In some embodiments, the side effects comprise insulin resistance.

In some embodiments according to any one of the embodiments above, the cancer is selected from the group consisting of breast cancer, lung cancer, pancreatic cancer, gastric cancer, colon cancer, liver cancer, and CLL. In some embodiments, the cancer is resistant to treatment with the other agent when not administered in combination with anordrin or analog thereof (such as anordrin).

In some embodiments according to any one of the embodiments above, the individual is positive for membrane bound estrogen receptor. In some embodiments, the individual is positive for VEGFR or EGFR.

In another aspect, there is provided a method of reducing a postmenopausal symptom in an individual, comprising administering to the individual: a) an effective amount of an anordrin or analog thereof (such as anordrin); and optionally b) an effective amount of at least one other agent selected from the group consisting of raloxifene or functional equivalent thereof and an aromatase inhibitor. In some embodiments, the other agent is raloxifene or functional equivalent thereof (such as raloxifene, lasofoxifene, or bazedoxifene). In some embodiments, the other agent is an aromatase inhibitor, such as anastrozole. In some embodiments, the postmenopausal symptom is selected from the group consisting of fat liver, insulin resistance, high sugar uptake and/or low cellular ATP concentrations, weight gain, high blood triglyceride, and osteoporosis and organ atrophy.

In some embodiments according to any one of the embodiments described above, the anordrin or analog thereof (such as anordrin) and the other agent are administered sequentially. In some embodiments, the anordrin or analog thereof (such as anordrin) and the other agent are administered simultaneously.

In some embodiments according to any one of the embodiments described above, the individual is human.

In yet another aspect, there is provided a pharmaceutical composition comprising anordrin or analog thereof (such as anordrin) and at least one other agent selected from the group consisting of tamoxifen, raloxifene or functional equivalent thereof, and an aromatase inhibitor. In some embodiments, the other agent is tamoxifen. In some embodiments, the other agent is raloxifene or functional equivalent thereof (including for example raloxifene, lasofoxifene, or bazedoxifene). In some embodiments, the other agent is an aromatase inhibitor, such as anastrozole.

In some embodiments, the pharmaceutical composition further comprises a lipid (such as corn oil). In some embodiments, the pharmaceutical composition further comprises protein (such as casein).

In some embodiments, the weight ratio of anordrin or analog thereof (such as anordrin) and the other agent in the composition is about 1:20 to about 20:1 (including for example about 10:1 to about 1:10, or about 1:10 to about 1:15).

The pharmaceutical composition can be present in a unit dosage form, for example an oral unit dosage form, such as capsules, tablets, pills, caplets, gels, liquids (e.g., suspensions, solutions, emulsions), powders or other particulates, and so forth.

Also provided are methods of using the pharmaceutical composition described herein for treating cancer, reducing side effects, and reducing a postmenopausal symptom as described herein.

These and other aspects and advantages of the present invention will become apparent from the subsequent detailed description and the appended claims. It is to be understood that one, some, or all of the properties of the various embodiments described herein may be combined to form other embodiments of the present invention.

BRIEF DESCRIPTION OF FIGURES

FIG. 1A: The percent of $^3$H-E2 bound to ER-α-LBD after competition with E2, tamoxifen (TAM) or ANO, normalized with $^3$H-E2 alone after subtracting blank; FIG. 1B: 10% SGS-PAGE stained with coomassie Blue R250 showing the GST fusion proteins purified by glutathione beads; FIG. 1C: Gel1 shows the expression of Bcl-2 in MCF-7 cells treated by TAM, ANO or blank using western blotting and probing with anti-Bcl-2 antibody; Gel2 shows the amount of actin protein in each sample; Gel3 is a longer exposure of Gel1.

FIG. 2A: The percent of $^3$H-E2 bound to ER-α-36 expressed in HEK-293 and competed by ANO or TAM, normalized with blank; FIG. 2B: The expression of ER-α-36 in HEK-293 cells was detected by western blotting with anti-ER-α antibody;

FIG. 2C: ANO significantly inhibits MDA-MB-231 cell growth (red columns) dependent on its dosage compared to tamoxifen (TAM) (blue columns); FIG. 2D: ANO and EGF together inhibit MDA-MB-231 cell growth; FIG. 2E: 6 µM [ANO] inhibits MDA-MB-231 cells migration tested by 8 µm transwell; FIG. 2F: 6 µM [ANO] plus 10 ng/ml [EGF] inhibits MDA-MB-231 cells migration tested by 8 µm transwell; FIG. 2G: 6 µM [ANO] inhibits integrin β1 distribution onto plasma membrane in MDA-MB-231 cells; FIG. 2H: 6 µM [ANO] inhibits integrin β1 distribution onto plasma membrane in MCF-7 cells.

FIG. 3A: ANO enhances glucose consumption in MCF-7 cells compared to the inhibition by TAM; FIG. 3B: 250 nM [ANO] not only neutralized the inhibition of 1 μM [TAM] on glucose consumption in MCF-7 cells but enhanced above basal levels; FIG. 3C: ANO can significantly decrease blood glucose concentration of female db/db mice.

FIG. 4A: ANO significantly blocks increased body mass compared to ipriflavone (IP) in OVX mice; FIG. 4B: ANO significantly blocks TAM-induced body mass increase; FIG. 4C and FIG. 4D: Paraffin sections of liver show that ANO can significantly decrease triglyceride accumulation compared to the same dose of IP in liver of OVX mice; FIG. 4E and FIG. 4F: Paraffin sections of liver show that ANO can significantly decrease the amount of triglyceride and non-alcohol steatohepatitis (NASH) induced by tamoxifen (TAM) compared to the same amount of IF in liver of normal mice; FIG. 4G: The grade of NASH is increased in liver cells closer to capillary vessels.

FIGS. 13A-13C: Effects of tamoxifen and anordrin or anordrin analog (such as anordrin) on cell growth, estrogen-controlled gene expression, and their interactions with the insulin pathway. FIG. 13A. $IC_{50}$ of anordin or tamoxifen for inhibiting growth of MCF-7 cells under culturing conditions with or without insulin in the media. Presence of insulin in the media reduces sensistivity of MCF-7 cells to tamoxifen, but increases sensitivity of MCF-7 cells to anordrin. FIG. 13B. RT-qPCR results showing $log_2$ fold changes of expression levels of genes under regulation by the estrogen classic pathway (such as BRCA1, ApoD, and COX7a), when MCF-7 cells were treated with anordrin (ANO), tamoxifen (TAM), or raloxifene (RAL), compared to MCF-7 cells without drug treatment. Anordrin treatment did not significantly affect BRCA1 transcription, but tamoxifen treatment significantly inhibited transcription of BRCA1 and COX7a mRNAs. FIG. 13C. Western blot showing that removal of insulin from the culture medium of MCF-7 cells resulted in increased expression of ER-α-36 at the protein level, but no visible difference in the expression levels of GPER1 or ER-α-66.

FIG. 16A: ANO does not significantly change food uptake in db/db mice; FIG. 16B: ANO does not significantly change food uptake compared with other groups in ovariectomized (OVX) mice; FIG. 16C: ANO does not significantly change food uptake compared to tamoxifen (TAM) groups in normal mice.

FIG. 17A: Total cholesterol in liver of ovariectomized (OVX) group; FIG. 17B: Total cholesterol in liver of TAM/ANO group.

FIG. 19A: Concentration-dependent morphological change and death of MDA-MB-231cells; FIG. 19B: The active drugs and concentration ranges.

FIG. 22A. Transient knockdown of ER-α-36 using specific siRNA decreased migration of MDA-MB-231 cells, but transient knockdown of GPER1 (using specific siRNA) or control using scrambled siRNA resulted in no significant effect on migration of MDA-MB-231 cells. Cell migration was measured used a matrixgel assay. FIG. 22B. Western blot showing that specific siRNAs were effective at knocking down ER-α-36 and GPER1 respectively at the protein level.

FIG. 23A. Glucose uptake by MCF-7-cells treated with tamoxifen and/or anordrin (ANO) were measured using a fluorescent glucose analog 2-NBDG (2-deoxy-2-[(7-nitro-2,1,3-benzoxadiazol-4-yl)amino]-D-glucose). Knockdown of ER-α-36 or GPER1 by specific siRNAs resulted in a significant decrease in glucose uptake in tamoxifen (TAM) or anordrin (ANO)-treated MCF-7 cells, as compared to drug-treated MCF-7 cells without RNAi knockdown of ER-α-36 or GPER1. FIG. 23B. ATP concentrations in MCF-7 cells treated with tamoxifen and/or anordrin (ANO) were measured using a fluorescence-based ATP analysis kit. Knockdown of ER-α-36 or GPER1 by specific siRNAs resulted in an increase in APT concentration in tamoxifen-treated cells, but a decrease in anordrin-treated cells, as compared with cells treated with corresponding drug but without RNAi knockdown. FIG. 23C. Western blot showing effective knockdown of ER-α-36 or GPER1 at the protein level by specific siRNAs.

DETAILED DESCRIPTION OF THE INVENTION

Figure 1A:
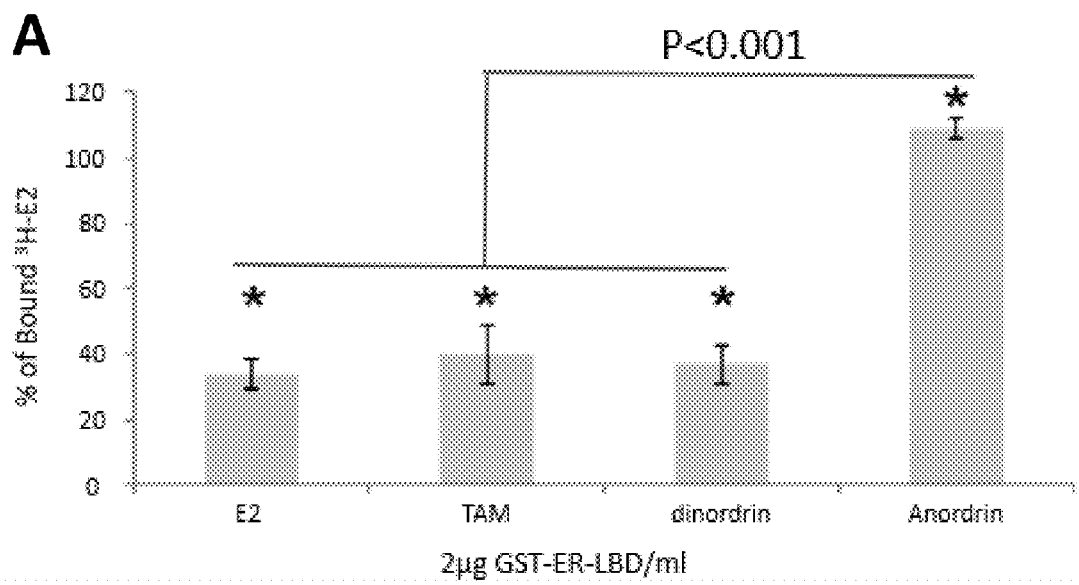
FIGS. 1A-1C: Anordrin or analog thereof (such as anordrin) does not bind to the ligand binding domain (LBD) of ER (2 µg GST-fusion protein couple onto beads) resulting in inability to modulate the estrogen classical pathway.
Figure 1B:
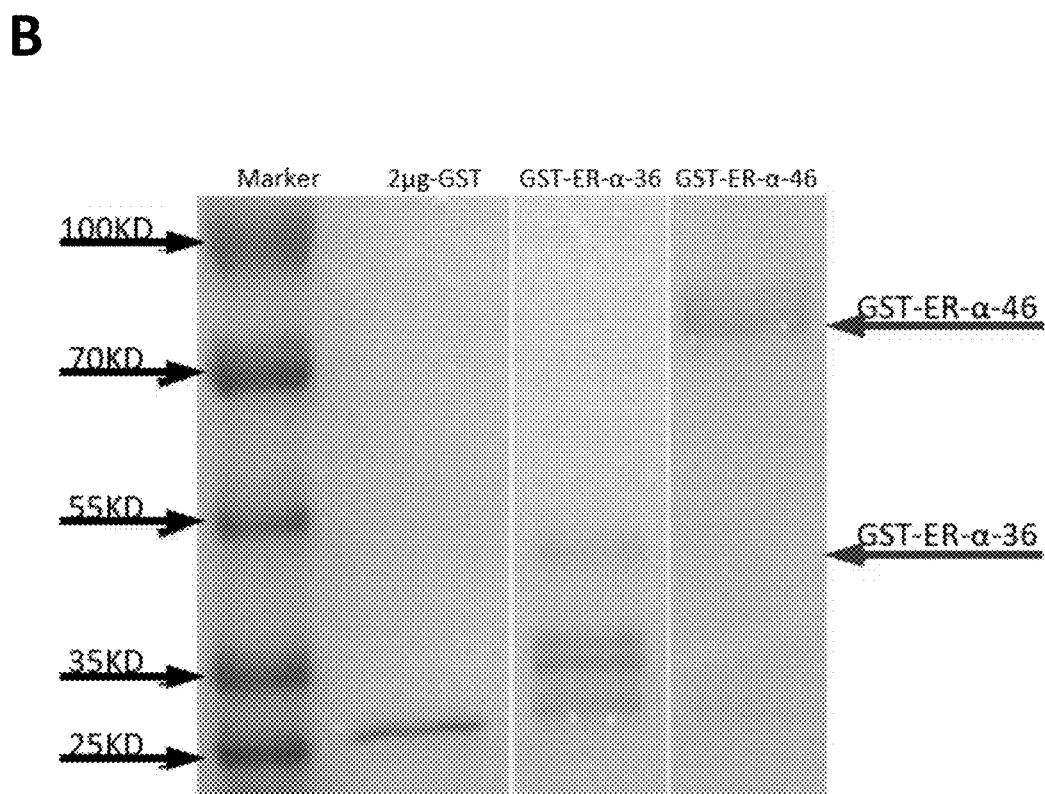

The present application provides methods and compositions for combination therapy comprising anordrin or analog thereof (such as anordrin) in conjunction with a second agent for treatment of cancer, reducing side effects, and reducing postmenopausal symptom(s). The inventions are based on the discovery of the unique properties and mechanism of actions of anordrin or analog thereof (such as anordrin). After a large scale screening, we surprisingly found that anordrin or analog thereof (such as anordrin) is a specifically selective estrogen receptor modulator of membrane-associated estrogen binding proteins. On the other hand, anordrin or analog thereof (such as anordrin) binds to GPER1 and functions as an agonist on the GPER1 pathway, which modulates metabolic signals to balance the consumption of bioenergy. The beneficial effects of anordrin or analog thereof (such as anordrin) thus include: i) the inhibition of malignant cell migration and growth regulated by membrane-associated estrogen receptors through estrogen-mediated HER/VEGFR pathways, ii) the modulation of estrogen metabolic effect as an agonist which leads to reduction of postmenopausal symptoms such as fat liver, weight gain, high blood triglyceride, and osteoporosis and organ atrophy, iii) the neutralization of detrimental effects by drugs such as tamoxifen, raloxifene and anastrozole, which include, for example, osteoporosis, non-alcohol steatohepatitis (NASH), atrophy of organs and endometrium cancer Thus, the present invention in one aspect provides methods for treating cancer comprising administering an anordrin or analog thereof (such as anordrin) alone or in combination with at least one other agent selected from the group consisting of tamoxifen, raloxifene or functional equivalent thereof, and an aromatase inhibitor.

In another aspect, there is provided a method of reducing side effect of at least one other agent selected from the group consisting of tamoxifen, raloxifene or functional equivalent thereof, and an aromatase inhibitor, by administering anordrin or analog thereof (such as anordrin) in combination with such other agent.

In another aspect, there is provided a method of reducing a postmenopausal syndrome by administering an anordrin or analog thereof (such as anordrin) alone or in combination with at least one other agent, wherein the other agent is raloxifene or functional equivalent thereof.

In another aspect, there is provided a method of reducing blood viscosity and thromboembolism by administering an anordrin or analog thereof (such as anordrin) alone or in combination with at least one other agent, wherein the other agent is raloxifene or functional equivalent thereof.

Also provided are pharmaceutical compositions comprising anordrin or analog thereof (such as anordrin) and at least one other agent selected from the group consisting of tamoxifen, raloxifene or functional equivalent thereof, and an aromatase inhibitor.

Definitions

It is to be understood by a person of ordinary skill in the art that the combination therapy methods described herein requires that one agent or composition be administered in conjunction with another agent. "In conjunction with" refers to administration of one treatment modality in addition to another treatment modality, such as administration of anordrin or analog thereof (such as anordrin) described herein in addition to administration of the second agent to the same individual. As such, "in conjunction with" refers to administration of one treatment modality before, during or after delivery of the other treatment modality to the individual.

The methods described herein are generally useful for treatment of diseases. As used herein, "treatment" is an approach for obtaining beneficial or desired clinical results. For example, for treatment of cancer, beneficial or desired clinical results include, but are not limited to, any one or more of: alleviation of one or more symptoms, diminishment of extent of disease, preventing or delaying spread (e.g., metastasis, for example metastasis to the lung or to the lymph node) of disease, preventing or delaying recurrence of disease, delay or slowing of disease progression, amelioration of the disease state, and remission (whether partial or total). Also encompassed by "treatment" is a reduction of pathological consequence of a proliferative disease. The methods of the invention contemplate any one or more of these aspects of treatment.

Individuals having "triple negative breast cancer" used herein refer to individuals who are clinically negative for expression of estrogen receptor (ER), progesterone receptors (PR) and HER2 protein.

"mER" refers to membrane-bound estrogen receptor. ER was facilitated onto plasma membrane through the palmitoylation modification at a Cysteine residue of its estrogen binding domain (LBD). ER-α-36 is a truncated ER-α variant. It remains palmitoylation motif (445-453) and possesses a unique 27 amino acid instead of 140 amino acid region (456-595) of fullength ER-α at C-terminus. Since ER-α-36 possesses a partial LBD and predominantly localizes at plasma membrane and cytosol, it does not bind with estrogen resulting in losing the modulating ability of estrogen classical pathway.

"mER" "EGFR positive," "VEGFR positive" used herein refer to individuals who are clinically positive for membrane-bound estrogen receptor, epidermal growth factor receptor (EGFR), or vascular epidermal growth factor receptor (VEGFR).

The term "effective amount" used herein refers to an amount of a compound or composition sufficient to treat a specified disorder, condition or disease such as ameliorate, palliate, lessen, and/or delay one or more of its symptoms. In reference to cancers, an effective amount comprises an amount sufficient to cause a tumor to shrink and/or to decrease the growth rate of the tumor (such as to suppress tumor growth) or to prevent or delay other unwanted cell proliferation.

The term "individual" is a mammal, including humans. An individual includes, but is not limited to, human, bovine, horse, feline, canine, rodent, or primate. In some embodiments, the individual is human.

The methods may be practiced in an adjuvant setting. "Adjuvant setting" refers to a clinical setting in which an individual has had a history of a proliferative disease, particularly cancer, and generally (but not necessarily) been responsive to therapy, which includes, but is not limited to, surgery (such as surgical resection), radiotherapy, and chemotherapy. However, because of their history of the proliferative disease (such as cancer), these individuals are considered at risk of development of the disease. Treatment or administration in the "adjuvant setting" refers to a subsequent mode of treatment. The degree of risk (i.e., when an individual in the adjuvant setting is considered as "high risk" or "low risk") depends upon several factors, most usually the extent of disease when first treated.

The methods provided herein may also be practiced in a "neoadjuvant setting," i.e., the method may be carried out before the primary/definitive therapy. In some embodiments, the individual has previously been treated. In some embodiments, the individual has not previously been treated. In some embodiments, the treatment is a first line therapy.

"Alkyl" is a linear or branched saturated hydrocarbon. For example, an alkyl group can have 1 to 12 carbon atoms (i.e., ($C_1$-$C_{12}$alkyl)), or 1 to 10 carbon atoms (i.e., ($C_1$-$C_{10}$alkyl)), or 1 to 8 carbon atoms (i.e., ($C_1$-$C_8$alkyl)), or 1 to 6 carbon atoms (i.e., ($C_1$-$C_6$alkyl)), or 1 to 4 carbon atoms (i.e., ($C_1$-$C_4$alkyl)). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —CH($CH_3$)$CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—CH($CH_2CH_3$)$_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—CH($CH_2CH_3$)($CH_2CH_2CH_3$)), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, and octyl (—$(CH_2)_7CH_3$).

"Alkenyl" is a linear or branched hydrocarbon with at least one carbon-carbon double bond. For example, an alkenyl group can have 2 to 12 carbon atoms (i.e., $C_2$-$C_{12}$alkenyl), or 2 to 10 carbon atoms (i.e., $C_2$-$C_{10}$alkenyl), or 2 to 8 carbon atoms (i.e., $C_2$-$C_8$alkenyl), or 2 to 6 carbon atoms (i.e., $C_2$-$C_6$alkenyl), or 2 to 4 carbon atoms (i.e., $C_2$-$C_4$alkenyl). Examples of suitable alkenyl groups include, but are not limited to, ethylene or vinyl (—CH=$CH_2$), allyl (—$CH_2$CH=$CH_2$) and 5-hexenyl (—$CH_2CH_2CH_2CH_2$CH=$CH_2$).

It is understood that aspect and embodiments of the invention described herein include "consisting" and/or "consisting essentially of" aspects and embodiments.

Reference to "about" a value or parameter herein includes (and describes) variations that are directed to that value or parameter per se. For example, description referring to "about X" includes description of "X".

As used herein and in the appended claims, the singular forms "a," "or," and "the" include plural referents unless the context clearly dictates otherwise. It is understood that aspects and variations of the invention described herein include "consisting" and/or "consisting essentially of" aspects and variations.

Methods for Cancer Treatment

The present invention in one aspect provides methods of treating cancer in an individual, comprising administering to the individual an effective amount of anordrin or analog thereof (such as anordrin). In some embodiments, there is provided a method of treating cancer in an individual, comprising administering to the individual: a) an effective amount of anordrin or analog thereof (such as anordrin); and b) an effective amount of at least one other agent selected from the group consisting of tamoxifen, raloxifene or functional equivalent thereof, and an aromatase inhibitor. In some embodiments, there is provided a method of treating cancer in an individual, comprising administering to the individual: a) an effective amount of anordrin or analog thereof (such as anordrin); and b) an effective amount of raloxifene. In some embodiments, there is provided a method of treating cancer in an individual, comprising administering to the individual: a) an effective amount of anordrin or analog thereof (such as anordrin); and b) an effective amount of tamoxifen. In some embodiments, there is provided a method of treating cancer in an individual, comprising administering to the individual: a) an effective amount of anordrin or analog thereof (such as anordrin); and b) an effective amount of lasofoxidene or bazedoxifene. In some embodiments, there is provided a method of treating cancer in an individual, comprising administering to the individual: a) an effective amount of anordrin or analog thereof (such as anordrin); and b) an effective amount of anastrozole. In some embodiments, the anordrin or analog thereof (such as anordrin) and the other agent are both administered orally. In some embodiments, the anordrin or analog thereof (such as anordrin) and the other agent are present in a single composition (such as the pharmaceutical compositions described herein), for example in the form of an oral dosage form.

In some embodiments, the cancer is selected from the group consisting of breast cancer, lung cancer (such as small cell lung cancer and non-small cell lung cancer), renal cancer, bladder cancer, pancreatic cancer, ovarian cancer, prostate cancer, brain cancer, colorectal cancer, leukemia, lymphoma, and multiple myeloma. In some embodiments, the individual is mER positive. In some embodiments, the individual is EGFR positive. In some embodiments, the individual is VEGFR positive. In some embodiments, the individual has solid tumor.

In some embodiments, there is provided a method of treating cancer in an individual, comprising administering to the individual: a) an effective amount of anordrin or analog thereof (such as anordrin); and b) an effective amount of at least one other agent, wherein the other agent is an EGFR inhibitor. In some embodiments, there is provided a method of treating cancer in an individual, comprising administering to the individual: a) an effective amount of anordrin or analog thereof (such as anordrin); and b) an effective amount of at least one other agent, wherein the other agent is a VEGFR inhibitor. In some embodiments, there is provided a method of treating cancer in an individual, comprising administering to the individual: a) an effective amount of anordrin or analog thereof (such as anordrin); and b) an effective amount of at least two other agents, wherein the two other agent are an EGFR inhibitor and a VEGFR inhibitor. In some embodiments, the method further comprises administering to the individual another agent selected from the group consisting of tamoxifen, raloxifene or functional equivalent thereof, and an aromatase inhibitor. In some embodiments, the cancer is EGFR positive. In some embodiments, the cancer is VEGFR positive. In some embodiments, the cancer is mER positive. In some embodiments, the cancer is EGFR positive and VEGFR positive. In some embodiments, the cancer is mER positive, EGFR positive, and VEGFR positive.

Suitable EGFR inhibitors include, for example, cetuximab, panitumumab, erlotinib, gefitinib, and vandetanib. Suitable VEGFR inhibitors include, for example, bevacizumab, pazopanib, regorafenib, and sorafenib.

In some embodiments, the anordrin or analog thereof (such as anordrin) and the other agent are administered sequentially. In some embodiments, the anordrin or analog thereof (such as anordrin) and the other agent are administered simultaneously.

In some embodiments, the anordrin or analog thereof (such as anordrin) and the other agent are administered concurrently. For example, in some embodiments, the administrations of the anordrin or analog thereof (such as anordrin) and the other agent are initiated at about the same time (for example, within any one of 1, 2, 3, 4, 5, 6, or 7 days). In some embodiments, the administrations of the anordrin or analog thereof (such as anordrin) and the other agent are terminated at about the same time (for example, within any one of 1, 2, 3, 4, 5, 6, or 7 days). In some embodiments, the administration of the other agent continues (for example for about any one of 0.5, 1, 2, 3, 4, 5, 6, 7, 8, 9, 10, 11, or 12 months) after the termination of the administration of the anordrin or analog thereof (such as anordrin). In some embodiments, the administration of the other agent is initiated after (for example after about any one of 0.5, 1, 2, 3, 4, 5, 6, 7, 8, 9, 10, 11, or 12 months) the initiation of the administration of the anordrin or analog thereof (such as anordrin). In some embodiments, the administrations of the anordrin or analog thereof (such as anordrin) and the other agent are initiated and terminated at about the same time. In some embodiments, the administrations of the anordrin or analog thereof (such as anordrin) and the other agent are initiated at about the same time and the administration of the other agent continues (for example for about any one of 0.5, 1, 2, 3, 4, 5, 6, 7, 8, 9, 10, 11, or 12 months) after the termination of the administration of the anordrin or analog thereof (such as anordrin). In some embodiments, the administration of the anordrin or analog thereof (such as anordrin) and the other agent stop at about the same time and the administration of the other agent is initiated after (for example after about any one of 0.5, 1, 2, 3, 4, 5, 6, 7, 8, 9, 10, 11, or 12 months) the initiation of the administration of the anordrin or analog thereof (such as anordrin). In some embodiments, the administration of the anordrin or analog thereof (such as anordrin) and the other agent stop at about the same time and the administration of the anordrin or analog thereof (such as anordrin) is initiated after (for example after about any one of 0.5, 1, 2, 3, 4, 5, 6, 7, 8, 9, 10, 11, or 12 months) the initiation of the administration of the other agent.

The anordrin or analog thereof (such as anordrin) and other agents described herein can be the agents themselves, pharmaceutically acceptable salts thereof, and pharmaceutically acceptable esters thereof, as well as stereoisomer, enantiomers, racemic mixtures, and the like. The other agent or agents as described can be administered as well as a pharmaceutical composition containing the agent(s), wherein the pharmaceutical composition comprises a pharmaceutically acceptable carrier vehicle, or the like.

The methods described herein require administration of the anordrin and/or analog thereof (such as anordrin) and the other agent in effective amounts. In some embodiments, an effective amount is an amount sufficient to delay development. In some embodiments, an effective amount is an amount sufficient to prevent or delay recurrence. An effective amount can be administered in one or more administrations. In the case of cancer, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

Thus, in some embodiments, there is provided a method of inhibiting cell proliferation (such as tumor growth) in an individual, comprising administering to the individual: a) an effective amount an anordrin or analog thereof (such as anordrin), and optionally b) an effective amount of at least one other agent selected from the group consisting of tamoxifen, raloxifene or functional equivalent thereof, and an aromatase inhibitor. In some embodiments, the effective amounts of the anordrin or analog thereof (such as anordrin) and the other agent synergistically inhibit cell proliferation (such as tumor cell growth). In some embodiments, at least about 10% (including for example at least about any of 20%, 30%, 40%, 60%, 70%, 80%, 90%, or 100%) cell proliferation is inhibited.

In some embodiments, there is provided a method of inhibiting tumor metastasis (such as metastasis of breast cancer, pulmonary metastasis or metastasis to the lymph node) in an individual, comprising administering to the individual: a) an effective amount an anordrin or analog thereof (such as anordrin), and optionally b) an effective amount of at least one other agent selected from the group consisting of tamoxifen, raloxifene or functional equivalent thereof, and an aromatase inhibitor. In some embodiments, the effective amounts of the anordrin or analog thereof (such as anordrin) and the other agent synergistically inhibit tumor metastasis. In some embodiments, at least about 10% (including for example at least about any of 20%, 30%, 40%, 60%, 70%, 80%, 90%, or 100%) metastasis is inhibited. In some embodiments, method of inhibiting metastasis to lymph node is provided. In some embodiments, method of inhibiting metastasis to the lung is provided.

In some embodiments, there is provided a method of reducing incidence or burden of preexisting tumor metastasis (such as pulmonary metastasis or metastasis to the lymph node) in an individual, comprising administering to the individual: a) an effective amount an anordrin or analog thereof (such as anordrin), and optionally b) an effective amount of at least one other agent selected from the group consisting of tamoxifen, raloxifene or functional equivalent thereof, and an aromatase inhibitor.

In some embodiments, there is provided a method of reducing tumor size in an individual, comprising administering to the individual: a) an effective amount an anordrin or analog thereof (such as anordrin), and optionally b) an effective amount of at least one other agent selected from the group consisting of tamoxifen, raloxifene or functional equivalent thereof, and an aromatase inhibitor. In some embodiments, the tumor size is reduced at least about 10% (including for example at least about any of 20%, 30%, 40%, 60%, 70%, 80%, 90%, or 100%).

In some embodiments, there is provided a method of prolonging time to disease progression of a cancer in an individual, comprising administering to the individual: a) an effective amount an anordrin or analog thereof (such as anordrin), and optionally b) an effective amount of at least one other agent selected from the group consisting of tamoxifen, raloxifene or functional equivalent thereof, and an aromatase inhibitor. In some embodiments, the method prolongs the time to disease progression by at least any of 1, 2, 3, 4, 5, 6, 7, 8, 9, 10, 11, or 12 weeks.

In some embodiments, there is provided a method of prolonging survival of an individual having a proliferative disease (such as cancer), comprising administering to the individual: a) an effective amount an anordrin or analog thereof (such as anordrin), and optionally b) an effective amount of at least one other agent selected from the group consisting of tamoxifen, raloxifene or functional equivalent thereof, and an aromatase inhibitor. In some embodiments, the method prolongs the survival of the individual by at least any of 1, 2, 3, 4, 5, 6, 7, 8, 9, 10, 11, 12, 18, or 24 month.

In some embodiments, the method is used to treat a primary tumor. In some embodiments, a method of treating metastatic cancer (that is, cancer that has metastasized from the primary tumor) is provided. In some embodiments, the method is for the treatment of an advanced disease or a lesser extent of disease, such as low tumor burden. In some embodiments, there is provided a method of treating cancer at an advanced stage. In some embodiments, the method is for the treatment of an early stage breast cancer. The methods may be practiced in an adjuvant setting. The methods provided herein may also be practiced in a neoadjuvant setting, i.e., the method may be carried out before the primary/definitive therapy. In some embodiments, the method further comprises conducting surgery on the individual following the completion of the treatment. For example, in some embodiments when the cancer is breast cancer, breast conserving surgery or mastectomy can be carried out within about 2, 3, 4, 5, 6, 7, 8, 9, 10, 11, or 12 weeks after completion of the neoadjuvant chemotherapy.

In some embodiments, the individual has previously been treated. In some embodiments, the individual has not previously been treated. In some embodiments, the treatment is a first line therapy. In some embodiments, the breast cancer has reoccurred after a remission.

In some embodiments, the cancer is breast cancer. These methods can be used, for example, to treat, stabilize, prevent, and/or delay any type or stage of breast cancer, such as early stage breast cancer, non-metastatic breast cancer, advanced breast cancer, stage IV breast cancer, locally advanced breast cancer, metastatic breast cancer, breast cancer in remission, breast cancer in an adjuvant setting, or breast cancer in a neoadjuvant setting. In some embodiments, the method is useful for preoperative systemic therapy (PST).

In some embodiments, there is provided a method of treating breast cancer (which may be HER2 positive or HER2 negative), including, for example, advanced breast cancer, stage IV breast cancer, locally advanced breast cancer, and metastatic breast cancer. In some embodiments, the breast cancer is luminal type B breast cancer. In some embodiments, the breast cancer is basal cell breast cancer. In some embodiments, the individual is diagnosed with T2, T3, or T4 lesion, or a stage N, M0 or T1c, N1-3 and M0. In some embodiments, the individual has an ECOG performance status of 0-1. In some embodiments, the individual has skin metastasis to the ipsilateral breast. In some embodiments, the individual has undergone prior therapy (such as hormonal therapy). In some embodiments, the individual has not undergone prior therapy (such as hormonal therapy). In some embodiments, the individual is awaiting definitive surgery. In some embodiments, the breast cancer is resected breast cancer. In some embodiments, the breast cancer is unresected breast cancer, such as unresected stage II or III breast cancer.

In some embodiments, the method is for treating an individual having one or more of these risk factors resulting in a higher probability of developing breast cancer than an individual without these risk factor(s). These risk factors include, but are not limited to, age, sex, race, diet, history of previous disease, presence of precursor disease, genetic (i.e., hereditary) considerations, and environmental exposure. In some embodiments, the individual may be a human who is genetically or otherwise predisposed to developing breast cancer who has or has not been diagnosed with breast cancer. Individuals at risk for breast cancer include, e.g., those having relatives who have experienced this disease, and those whose risk is determined by analysis of genetic or biochemical markers. For example, the individual may be a human who has a gene, genetic mutation, or polymorphism associated with breast cancer (e.g., BRCA1, BRCA2, ATM, CHEK2, RAD51, AR, DIRAS3, ERBB2, and/or TP53) or has one or more extra copies of a gene (e.g., one or more extra copies of the HER2 gene) associated with breast cancer. In some embodiments, the breast cancer is HER2 negative. In some embodiments, the breast cancer is ER negative. In some embodiments, the breast cancer is PR negative. In some embodiments, the breast cancer is EP negative and HER2 negative. In some embodiments, the breast cancer is PR negative and HER2 negative. In some embodiments, the breast cancer is ER negative and PR negative. In some embodiment, the breast cancer is ER negative, PR negative, and HER2 negative.

The methods described herein are also useful for treating other solid tumors (such as advanced solid tumors). In some embodiments, there is provided a method of treating lung cancer, including, for example, non-small cell lung cancer (NSCLC, such as advanced NSCLC), small cell lung cancer (SCLC, such as advanced SCLC), and advanced solid tumor malignancy in the lung. In some embodiments, there is provided a method of treating any of ovarian cancer, head and neck cancer, gastric malignancies, melanoma (including metastatic melanoma and malignant melanoma), ovarian cancer, colorectal cancer, and pancreatic cancer.

In some embodiments, the method is useful for treating one or more of the following: cutaneous T cell lymphoma (CTCL), leukemia, follicular lymphoma, Hodgkin lymphoma, and acute myeloid leukemia.

In some embodiments, the disease is a cancer of any one of the following: basal cell carcinoma, medulloblastoma, glioblastoma, multiple myeloma, chronic myelogenous leukemia (CML), acute myelogenous leukemia, pancreatic cancer, lung cancer (small cell lung cancer and non-small cell lung cancer), esophageal cancer, stomach cancer, billary cancer, prostate cancer, liver cancer, hepatocellular cancer, gastrointestinal cancer, gastric cancer, and ovarian and bladder cancer. In some embodiments, the cancer is selected from the group consisting of pancreas ductal adenocarcinoma, colon adenocarcinoma, and ovary cystadenocarcinoma. In some embodiments, the cancer is pancreas ductal adenocarcinoma. In some embodiments, the cancer is a tumor that is poorly perfused and/or poorly vascularized.

In some embodiments, the cancer is pancreatic cancer, including for example pancreatic adenocarcinoma, pancreatic adenosquamous carcinoma, pancreatic squamous cell carcinoma, and pancreatic giant cell carcinoma. In some embodiments, the pancreatic cancer is exocrine pancreatic cancer. In some embodiments, the pancreatic cancer is endocrine pancreatic cancer (such as islet cell carcinoma). In some embodiments, the pancreatic cancer is advanced metastatic pancreatic cancer.

Other examples of cancers that may be treated by the methods of the invention include, but are not limited to, adenocortical carcinoma, agnogenic myeloid metaplasia, AIDS-related cancers (e.g., AIDS-related lymphoma), anal cancer, appendix cancer, astrocytoma (e.g., cerebellar and cerebral), basal cell carcinoma, bile duct cancer (e.g., extrahepatic), bladder cancer, bone cancer, (osteosarcoma and malignant fibrous histiocytoma), brain tumor (e.g., glioma, brain stem glioma, cerebellar or cerebral astrocytoma (e.g., pilocytic astrocytoma, diffuse astrocytoma, anaplastic (malignant) astrocytoma), malignant glioma, ependymoma, oligodenglioma, meningioma, craniopharyngioma, haemangioblastomas, medulloblastoma, supratentorial primitive neuroectodermal tumors, visual pathway and hypothalamic glioma, and glioblastoma), breast cancer, bronchial adenomas/carcinoids, carcinoid tumor (e.g., gastrointestinal carcinoid tumor), carcinoma of unknown primary, central nervous system lymphoma, cervical cancer, colon cancer, colorectal cancer, chronic myeloproliferative disorders, endometrial cancer (e.g., uterine cancer), ependymoma, esophageal cancer, Ewing's family of tumors, eye cancer (e.g., intraocular melanoma and retinoblastoma), gallbladder cancer, gastric (stomach) cancer, gastrointestinal carcinoid tumor, gastrointestinal stromal tumor (GIST), germ cell tumor, (e.g., extracranial, extragonadal, ovarian), gestational trophoblastic tumor, head and neck cancer, hepatocellular (liver) cancer (e.g., hepatic carcinoma and heptoma), hypopharyngeal cancer, islet cell carcinoma (endocrine pancreas), laryngeal cancer, laryngeal cancer, leukemia, lip and oral cavity cancer, oral cancer, liver cancer, lung cancer (e.g., small cell lung cancer, non-small cell lung cancer, adenocarcinoma of the lung, and squamous carcinoma of the lung), lymphoid neoplasm (e.g., lymphoma), medulloblastoma, ovarian cancer, mesothelioma, metastatic squamous neck cancer, mouth cancer, multiple endocrine neoplasia syndrome, myelodysplastic syndromes, myelodysplastic/myeloproliferative diseases, nasal cavity and paranasal sinus cancer, nasopharyngeal cancer, neuroblastoma, neuroendocrine cancer, oropharyngeal cancer, ovarian cancer (e.g., ovarian epithelial cancer, ovarian germ cell tumor, ovarian low malignant potential tumor), pancreatic cancer, parathyroid cancer, penile cancer, cancer of the peritoneal, pharyngeal cancer, pheochromocytoma, pineoblastoma and supratentorial primitive neuroectodermal tumors, pituitary tumor, pleuropulmonary blastoma, lymphoma, primary central nervous system lymphoma (microglioma), pulmonary lymphangiomyomatosis, rectal cancer, renal cancer, renal pelvis and ureter cancer (transitional cell cancer), rhabdomyosarcoma, salivary gland cancer, skin cancer (e.g., non-melanoma (e.g., squamous cell carcinoma), melanoma, and Merkel cell carcinoma), small intestine cancer, squamous cell cancer, testicular cancer, throat cancer, thymoma and thymic carcinoma, thyroid cancer, tuberous sclerosis, urethral cancer, vaginal cancer, vulvar cancer, Wilms' tumor, and post-transplant lymphoproliferative disorder (PTLD), abnormal vascular proliferation associated with phakomatoses, edema (such as that associated with brain tumors), and Meigs' syndrome.

In some embodiments, the cancer is a solid tumor (such as advanced solid tumor). Solid tumor includes, but is not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, Kaposi's sarcoma, soft tissue sarcoma, uterine sacronomasynovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma (including for example adenocarcinoma, clear cell renal cell carcinoma, papillary renal cell carcinoma, chromophobe renal cell carcinoma, collecting duct renal cell carcinoma, granular renal cell carcinoma, mixed granular renal cell carcinoma, renal angiomyolipomas, or spindle renal cell carcinoma.), hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

In some embodiments the lymphoid neoplasm (e.g., lymphoma) is a B-cell neoplasm. Examples of B-cell neoplasms include, but are not limited to, precursor B-cell neoplasms (e.g., precursor B-lymphoblastic leukemia/lymphoma) and peripheral B-cell neoplasms (e.g., B-cell chronic lymphocytic leukemia/prolymphocytic leukemia/small lymphocytic lymphoma (small lymphocytic (SL) NHL), lymphoplasmacytoid lymphoma/immunocytoma, mantel cell lymphoma, follicle center lymphoma, follicular lymphoma (e.g., cytologic grades: I (small cell), II (mixed small and large cell), III (large cell) and/or subtype: diffuse and predominantly small cell type), low grade/follicular non-Hodgkin's lymphoma (NHL), intermediate grade/follicular NHL, marginal zone B-cell lymphoma (e.g., extranodal (e.g., MALT-type +/−monocytoid B cells) and/or Nodal (e.g., +/−monocytoid B cells)), splenic marginal zone lymphoma (e.g., +/−villous lymphocytes), Hairy cell leukemia, plasmacytoma/plasma cell myeloma (e.g., myeloma and multiple myeloma), diffuse large B-cell lymphoma (e.g., primary mediastinal (thymic) B-cell lymphoma), intermediate grade diffuse NHL, Burkitt's lymphoma, High-grade B-cell lymphoma, Burkitt-like, high grade immunoblastic NHL, high grade lymphoblastic NHL, high grade small non-cleaved cell NHL, bulky disease NHL, AIDS-related lymphoma, and Waldenstrom's macroglobulinemia).

In some embodiments the lymphoid neoplasm (e.g., lymphoma) is a T-cell and/or putative NK-cell neoplasm. Examples of T-cell and/or putative NK-cell neoplasms include, but are not limited to, precursor T-cell neoplasm (precursor T-lymphoblastic lymphoma/leukemia) and peripheral T-cell and NK-cell neoplasms (e.g., T-cell chronic lymphocytic leukemia/prolymphocytic leukemia, and large granular lymphocyte leukemia (LGL) (e.g., T-cell type and/or NK-cell type), cutaneous T-cell lymphoma (e.g., mycosis fungoides/Sezary syndrome), primary T-cell lymphomas unspecified (e.g., cytological categories (e.g., medium-sized cell, mixed medium and large cell), large cell, lymphoepitheloid cell, subtype hepatosplenic γδ T-cell lymphoma, and subcutaneous panniculitic T-cell lymphoma), angioimmunoblastic T-cell lymphoma (AILD), angiocentric lymphoma, intestinal T-cell lymphoma (e.g., +/−enteropathy associated), adult T-cell lymphoma/leukemia (ATL), anaplastic large cell lymphoma (ALCL) (e.g., CD30+, T- and null-cell types), anaplastic large-cell lymphoma, and Hodgkin's like).

In some embodiments the lymphoid neoplasm (e.g., lymphoma) is Hodgkin's disease. For example, the Hodgkin's disease may be lymphocyte predominance, nodular sclerosis, mixed cellularity, lymphocyte depletion, and/or lymphocyte-rich.

In some embodiments, the cancer is leukemia. In some embodiments, the leukemia is chronic leukemia. Examples of chronic leukemia include, but are not limited to, chronic myelocytic I (granulocytic) leukemia, chronic myelogenous, and chronic lymphocytic leukemia (CLL). In some embodiments, the leukemia is acute leukemia. Examples of acute leukemia include, but are not limited to, acute lymphoblastic leukemia (ALL), acute myeloid leukemia, acute lymphocytic leukemia, and acute myelocytic leukemia (e.g., myeloblastic, promyelocytic, myelomonocytic, monocytic, and erythroleukemia).

In some embodiments, the cancer is liquid tumor or plasmacytoma. Plasmacytoma includes, but is not limited to, myeloma. Myeloma includes, but is not limited to, an extramedullary plasmacytoma, a solitary myeloma, and multiple myeloma. In some embodiments, the plasmacytoma is multiple myeloma.

In some embodiments, the cancer is multiple myeloma. Examples of multiple myeloma include, but are not limited to, IgG multiple myeloma, IgA multiple myeloma, IgD multiple myeloma, IgE multiple myeloma, and nonsecretory multiple myeloma. In some embodiments, the multiple myeloma is IgG multiple myeloma. In some embodiments, the multiple myeloma is IgA multiple myeloma. In some embodiments, the multiple myeloma is a smoldering or indolent multiple myeloma. In some embodiments, the multiple myeloma is progressive multiple myeloma. In some embodiments, multiple myeloma may be resistant to a drug, such as, but not limited to, bortezomib, dexamethasone (Dex-), doxorubicin (Dox-), and melphalan (LR).

In some embodiments, there are provided methods of reducing side effect of at least one other agent by anordrin or analog thereof (such as anordrin), comprising administering to the individual an effective amount of anordrin or analog thereof (such as anordrin) in combination with the other agent, wherein the other agent is selected from the group consisting of tamoxifen, raloxifene or functional equivalent thereof, and an aromatase inhibitor. In some embodiments, the individual is mER positive. In some embodiments, the individual is EGFR positive. In some embodiments, the individual is VEGFR positive.

Side effects of tamoxifen include, e.g., uterine cancer, non-alcohol steatohepatitis (NASH), cardiovascular and heart attack, diarrhea, nausea, headache, hot flashes, sinusitis, weight gain, leg cramps, and ankle swelling. Side effects of raloxifene include, e.g., decreasing blood triglyceride, NASH, cardiovascular and heart attack, blood clots, stoke, deep vein thrombosis, and pulomary embolism. Side effects of anastrozole include, e.g., diarrhea, nausea, headache, hot flashes, sinusitis, weight gain, muscle pain, organ atrophy, and osteoporosis.

In some embodiments, mER status is used as a basis for selecting individuals for cancer treatment (or reducing side effects of the other agents in cancer treatment). The levels of mER can be used, for example, for determining (and aiding assessment) in any one or more of the following: a) probably or likely suitability of an individual to initially receive treatment; b) probable or likely unsuitability of an individual to initially receive treatment(s); c) responsiveness to treatment; d) probable or likely suitability of an individual to continue to receive treatment; e) probable or likely unsuitability of an individual to receive treatment(s); f) adjusting dosages; g) predicting likelihood of clinical benefits. The present application encompasses any of these methods.

For example, in some embodiments, there is provided a method of treating cancer in an individual (such as a human individual) comprising administering to the individual: a) an effective amount of anordrin or analog thereof (such as anordrin); and optionally b) an effective amount of at least one other agent selected from the group consisting of tamoxifen, raloxifene or functional equivalent thereof, and an aromatase inhibitor, wherein the individual has a high level of mER. In some embodiments, there is provided a method of treating cancer in an individual (such as a human individual) comprising administering to the individual: a) an effective amount of anordrin or analog thereof (such as anordrin); and optionally b) an effective amount of at least one other agent selected from the group consisting of tamoxifen, raloxifene or functional equivalent thereof, and an aromatase inhibitor, wherein the level of mER is used as a basis for selecting the individual for treatment. In some embodiments, the individual is selected for treatment if the individual has a high level of mER. In some embodiments, the level of mER is determined by immunohistochemistry method. In some embodiments, the level of the mER is based on protein expression level. In some embodiments, the level of the mER is based on mRNA level. In some embodiments, the level of the mER is based on Ca2+ signal in response to estrogen stimulation. In some embodiments, the method further comprises determining the level of the mER prior to the treatment. In some embodiments, the method further comprises selecting the individual for treatment based on the mER level.

The levels of mER may be a high level or a low level as compared to a control sample. In some embodiments, the level of the mER in an individual is compared to the level of the mER in a control sample. In some embodiments the level of the mER in a subject is compared to the level of the mER in multiple control samples. In some embodiments, multiple control samples are used to generate a statistic that is used to classify the level of the mER in an individual with cancer.

The classification or ranking of the mER level (i.e., high or low) may be determined relative to a statistical distribution of control levels. In some embodiments, the classification or ranking is relative to a control sample obtained from the individual. In some embodiment the levels of the mER is classified or ranked relative to a statistical distribution of control levels. In some embodiments, the level of the mER is classified or ranked relative to the level from a control sample obtained from the subject.

Control samples can be obtained using the same sources and methods as non-control samples. In some embodiments, the control sample is obtained from a different individual (for example an individual not having cancer and/or an individual sharing similar ethnic, age, and gender identity). In some embodiments when the sample is a tumor tissue sample, the control sample may be a non-cancerous sample from the same individual. In some embodiments, multiple control samples (for example from different individuals) are used to determine a range of levels of mER in a particular tissue, organ, or cell population. In some embodiments, the control sample is a cultured tissue or cell that has been determined to be a proper control. In some embodiments, the control is a cell that does not express the mER In some embodiments, a clinically accepted normal level in a standardized test is used as a control level for determining the mER level. In some embodiments, the reference level of mER in the subject is classified as high, medium or low according to a scoring system, such as an immunohistochemistry-based scoring system.

In some embodiments, the mER level is determined by measuring the level of a mER in an individual and comparing to a control or reference (e.g., the median level for the given patient population or level of a second individual). For example, if the level of mER for the single individual is determined to be above the median level of the patient population, that individual is determined to have high expression of the mER. Alternatively, if the level of a mER for the single individual is determined to be below the median level of the patient population, that individual is determined to have low expression of the mER. In some embodiments, the individual is compared to a second individual and/or a patient population which is responsive to treatment. In some embodiments, the individual is compared to a second individual and/or a patient population which is not responsive to treatment. In any of the embodiments herein, the levels are determined by measuring the level of mER. For example, if the level of an mRNA encoding mER for the single individual is determined to be above the median level of the patient population, that individual is determined to have a high level of an mRNA encoding mER. Alternatively, if the level of mRNA encoding the mER for the single individual is determined to be below the median level of the patient population, that individual is determined to have a low level of an mRNA encoding mER.

In some embodiments, the reference level of mER is determined by obtaining a statistical distribution of mER levels.

In some embodiments, bioinformatics methods are used for the determination and classification of the levels of mER. Numerous alternative bioinformatics approaches have been developed to assess gene set expression profiles using gene expression profiling data. Methods include but are not limited to those described in Segal, E. et al. Nat. Genet. 34:66-176 (2003); Segal, E. et al. Nat. Genet. 36:1090-1098 (2004); Barry, W. T. et al. Bioinformatics 21:1943-1949 (2005); Tian, L. et al. Proc Nat'l Acad Sci USA 102:13544-13549 (2005); Novak B A and Jain A N. Bioinformatics 22:233-41 (2006); Maglietta R et al. Bioinformatics 23:2063-72 (2007); Bussemaker H J, BMC Bioinformatics 8 Suppl 6:S6 (2007).

In some embodiments, mRNA level is determined, and a low level is an mRNA level less than about 1.1, 1.2, 1.3, 1.5, 1.7, 2, 2.2, 2.5, 2.7, 3, 5, 7, 10, 20, 50, 70, 100, 200, 500, 1000 times or less than 1000 times to that of what is considered as clinically normal or to the level obtained from a control. In some embodiments, high level is an mRNA level more than about 1.1, 1.2, 1.3, 1.5, 1.7, 2, 2.2, 2.5, 2.7, 3, 5, 7, 10, 20, 50, 70, 100, 200, 500, 1000 times or more than 1000 times to that of what is considered as clinically normal or to the level obtained from a control.

In some embodiments, protein expression level is determined, for example by immunohistochemistry. For example, the criteria for low or high levels can be made based on the number of positive staining cells and/or the intensity of the staining, for example by using an antibody that specifically recognizes the mER protein. In some embodiments, the level is low if less than about 1%, 5%, 10%, 15%, 20%, 25%, 30%, 35%, 40%, 45%, or 50% cells have positive staining. In some embodiments, the level is low if the staining is 1%, 5%, 10%, 15%, 20%, 25%, 30%, 35%, 40%, 45%, or 50% less intense than a positive control staining.

In some embodiments, the level is high if more than about 40%, 45%, 50%, 55%, 60%, 65%, 70%, 75%, 80%, 85%, or 90%, cells have positive staining. In some embodiments, the level is high if the staining is as intense as positive control staining. In some embodiments, the level is high if the staining is 80%, 85%, or 90% as intense as positive control staining.

In some embodiments, strong staining, moderate staining, and weak staining are calibrated levels of staining, wherein a range is established and the intensity of staining is binned within the range. In some embodiments, strong staining is staining above the 75th percentile of the intensity range, moderate staining is staining from the 25th to the 75th percentile of the intensity range, and low staining is staining is staining below the 25th percentile of the intensity range. In some aspects one skilled in the art, and familiar with a particular staining technique, adjusts the bin size and defines the staining categories.

In some embodiments, estrogen sensitive level is determined, for example by Ca2+ oscillation or electrophysiological pathclamp. For example, the criteria for low or high levels can be made based on the change of Ca2+ concentration or responsive signal of positive cells, for example by using estrogen. In some embodiments, the level is low if less than about 1%, 5%, 10%, 15%, 20%, 25%, 30%, 35%, 40%, 45%, or 50% cells have positive sensitivity. In some embodiments, the level is low if the change of Ca2+ concentration or responsive signal is 1%, 5%, 10%, 15%, 20%, 25%, 30%, 35%, 40%, 45%, or 50% less intense than a positive control sensitivity.

In some embodiments, the level is high if more than about 40%, 45%, 50%, 55%, 60%, 65%, 70%, 75%, 80%, 85%, or 90%, cells have positive change. In some embodiments, the level is high if the sensitivity is as intense as positive control sensitivity. In some embodiments, the level is high if the change is 80%, 85%, or 90% as intense as positive control.

In some embodiments, most sensitivity, moderate sensitivity, and weak sensitivity are calibrated levels of Ca2+ signal in cells, wherein a range is established and the intensity of Ca2+ signal is binned within the range. In some embodiments, most sensitivity is the change of Ca2+ signal above the 75th percentile of the intensity range, moderate sensitivity is the change of Ca2+ signal from the 25th to the 75th percentile of the intensity range, and low sensitivity is the change of Ca2+ signal is measuring below the 25th percentile of the intensity range. In some aspects one skilled in the art, and familiar with a particular perfusion technique, adjusts the bin size and defines the signal recording categories.

Methods of Reducing Postmenopausal Syndrome

In some embodiments, there are provided methods of reducing a postmenopausal symptom in an individual, comprising administering to the individual an effective amount of an anordrin or analog thereof (such as anordrin).

In some embodiments, there are provided methods of reducing a postmenopausal symptom in an individual, comprising administering to the individual: a) an effective amount of an anordrin or analog thereof (such as anordrin); and b) an effective amount of at least one other agent is selected from the group consisting of raloxifene or functional equivalent thereof and an aromatase inhibitor. In some embodiments, the anordrin or analog thereof (such as anordrin) and the other agent are administered sequentially. In some embodiments, the anordrin or analog thereof (such as anordrin) and the other agent are administered simultaneously (for example in a single composition, such as the pharmaceutical compositions described herein).

Postmenopausal syndromes described herein include, but are not limited to, fat liver, weight gain, high blood triglyceride, and osteoporosis and organ atrophy.

Thus, for example, in some embodiments, there is provided a method of preventing (or reducing symptoms of) osteoporosis in an individual, comprising administering to the individual an effective amount of an anordrin or analog thereof (such as anordrin). In some embodiments, there is provided a method of preventing (or reducing symptoms of) osteoporosis in an individual, comprising administering to the individual: a) an effective amount of an anordrin or analog thereof (such as anordrin); and b) an effective amount of at least one other agent, wherein the other agent is raloxifene or functional equivalent thereof. In some embodiments, the other agent is raloxifene. In some embodiments, the other agent is selected from the group consisting of tamoxifen, raloxifene, lasofoxifene, bazedoxifene, arzoxifene, ormeloxifene, ospemifene, and levormeloxifene. In some embodiments, there is provided a method of preventing (or reducing symptoms of) osteoporosis in an individual, comprising administering to the individual: a) an effective amount of an anordrin or analog thereof (such as anordrin); and b) an effective amount of at least one other agent, wherein the other agent is an aromatase inhibitor. In some embodiments, the other agent is anastrozole. In some embodiments, the method further comprises administering to the individual an effective amount of calcium. Suitable amounts of calcium include, but are not limited to, about 1 to about 500 mg/day, such as about 10 to about 200 mg/day, about 50 to about 1500 mg/day. In some embodiments, the method further comprises administering to the individual an effective amount of vitamin D. Suitable amounts of vitamin D include, but are not limited to, about 400 to about 800 IU/day, such as about 500 to about 600 IU/day.

In some embodiments, there is provided a method of preventing (or reducing symptoms of) fatty liver in an individual, comprising administering to the individual an effective amount of an anordrin or analog thereof (such as anordrin). In some embodiments, there is provided a method of preventing (or reducing symptoms of) fatty liver in an individual, comprising administering to the individual: a) an effective amount of an anordrin or analog thereof (such as anordrin); and b) an effective amount of at least one other agent, wherein the other agent is raloxifene or functional equivalent thereof. In some embodiments, the other agent is raloxifene. In some embodiments, the other agent is selected from the group consisting of tamoxifen, raloxifene, lasofoxifene, bazedoxifene, arzoxifene, ormeloxifene, ospemifene, and levormeloxifene. In some embodiments, there is provided a method of preventing (or reducing symptoms of) fatty liver in an individual, comprising administering to the individual: a) an effective amount of an anordrin or analog thereof (such as anordrin); and b) an effective amount of at least one other agent, wherein the other agent is an aromatase inhibitor. In some embodiments, the other agent is anastrozole.

In some embodiments, there is provided a method of preventing (or reducing symptoms of) insulin resistance in an individual, comprising administering to the individual an effective amount of an anordrin or analog thereof (such as anordrin). In some embodiments, there is provided a method of preventing (or reducing symptoms of) insulin resistance in an individual, comprising administering to the individual: a) an effective amount of an anordrin or analog thereof (such as anordrin); and b) an effective amount of at least one other agent, wherein the other agent is raloxifene or functional equivalent thereof. In some embodiments, the other agent is raloxifene. In some embodiments, the other agent is selected from the group consisting of tamoxifen, raloxifene, lasofoxifene, bazedoxifene, arzoxifene, ormeloxifene, ospemifene, and levormeloxifene. In some embodiments, there is provided a method of preventing (or reducing symptoms of) insulin resistance in an individual, comprising administering to the individual: a) an effective amount of an anordrin or analog thereof (such as anordrin); and b) an effective amount of at least one other agent, wherein the other agent is an aromatase inhibitor. In some embodiments, the other agent is anastrozole.

In some embodiments, there is provided a method of reducing sugar uptake or increasing cellular ATP concentrations or both in an individual, comprising administering to the individual an effective amount of an anordrin or analog thereof (such as anordrin). In some embodiments, there is provided a method of reducing sugar uptake or increasing cellular ATP concentrations or both in an individual, comprising administering to the individual: a) an effective amount of an anordrin or analog thereof (such as anordrin); and b) an effective amount of at least one other agent, wherein the other agent is raloxifene or functional equivalent thereof. In some embodiments, the other agent is raloxifene. In some embodiments, the other agent is selected from the group consisting of tamoxifen, raloxifene, lasofoxifene, bazedoxifene, arzoxifene, ormeloxifene, ospemifene, and levormeloxifene. In some embodiments, there is provided a method of reducing sugar uptake or increasing cellular ATP concentrations or both in an individual, comprising administering to the individual: a) an effective amount of an anordrin or analog thereof (such as anordrin); and b) an effective amount of at least one other agent, wherein the other agent is an aromatase inhibitor. In some embodiments, the other agent is anastrozole.

In some embodiments, there is provided a method of preventing (or reducing symptoms of) organ atrophy in an individual, comprising administering to the individual an effective amount of an anordrin or analog thereof (such as anordrin). In some embodiments, there is provided a method of preventing (or reducing symptoms of) organ atrophy in an individual, comprising administering to the individual: a) an effective amount of an anordrin or analog thereof (such as anordrin); and b) an effective amount of at least one other agent, wherein the other agent is raloxifene or functional equivalent thereof. In some embodiments, the other agent is raloxifene. In some embodiments, the other agent is selected from the group consisting of tamoxifen, raloxifene, lasofoxifene, bazedoxifene, arzoxifene, ormeloxifene, ospemifene, and levormeloxifene. In some embodiments, there is provided a method of preventing (or reducing symptoms of) organ atrophy in an individual, comprising administering to the individual: a) an effective amount of an anordrin or analog thereof (such as anordrin); and b) an effective amount of at least one other agent, wherein the other agent is an aromatase inhibitor. In some embodiments, the other agent is anastrozole.

In some embodiments, there is provided a method of preventing (or reducing symptoms of) weight gain in an individual, comprising administering to the individual an effective amount of an anordrin or analog thereof (such as anordrin). In some embodiments, there is provided a method of preventing (or reducing symptoms of) weight gain in an individual, comprising administering to the individual: a) an effective amount of an anordrin or analog thereof (such as anordrin); and b) an effective amount of at least one other agent, wherein the other agent is raloxifene or functional equivalent thereof. In some embodiments, the other agent is raloxifene. In some embodiments, the other agent is selected from the group consisting of tamoxifen, raloxifene, lasofoxifene, bazedoxifene, arzoxifene, ormeloxifene, ospemifene, and levormeloxifene. In some embodiments, there is provided a method of preventing (or reducing symptoms of) weight gain in an individual, comprising administering to the individual: a) an effective amount of an anordrin or analog thereof (such as anordrin); and b) an effective amount of at least one other agent, wherein the other agent is an aromatase inhibitor. In some embodiments, the other agent is anastrozole.

In some embodiments, there is provided a method of reducing blood triglyceride in an individual, comprising administering to the individual an effective amount of an anordrin or analog thereof (such as anordrin). In some embodiments, there is provided a method of reducing blood triglyceride in an individual, comprising administering to the individual: a) an effective amount of an anordrin or analog thereof (such as anordrin); and b) an effective amount of at least one other agent, wherein the other agent is raloxifene or functional equivalent thereof. In some embodiments, the other agent is raloxifene. In some embodiments, the other agent is selected from the group consisting of tamoxifen, raloxifene, lasofoxifene, bazedoxifene, arzoxifene, ormeloxifene, ospemifene, and levormeloxifene. In some embodiments, there is provided a method of reducing blood triglyceride in an individual, in an individual, comprising administering to the individual: a) an effective amount of an anordrin or analog thereof (such as anordrin); and b) an effective amount of at least one other agent, wherein the other agent is an aromatase inhibitor. In some embodiments, the other agent is anastrozole.

In some embodiments, there is provided a method of reducing blood viscocity and/or thromboembolism in an individual, comprising administering to the individual an effective amount of an anordrin or analog thereof (such as anordrin). In some embodiments, there is provided a method of reducing blood viscocity and/or thromboembolism in an individual, comprising administering to the individual: a) an effective amount of an anordrin or analog thereof (such as anordrin); and b) an effective amount of at least one other agent, wherein the other agent is raloxifene or functional equivalent thereof. In some embodiments, the other agent is raloxifene. In some embodiments, the other agent is selected from the group consisting of tamoxifen, raloxifene, lasofoxifene, bazedoxifene, arzoxifene, ormeloxifene, ospemifene, and levormeloxifene. In some embodiments, there is provided a method of reducing blood viscocity and/or thromboembolism in an individual, in an individual, comprising administering to the individual: a) an effective amount of an anordrin or analog thereof (such as anordrin); and b) an effective amount of at least one other agent, wherein the other agent is an aromatase inhibitor. In some embodiments, the other agent is anastrozole.

Modes of Administration

In the context of combination therapy, the composition comprising anordrin or analog thereof (such as anordrin) and the other agent can be administered simultaneously (i.e., simultaneous administration) and/or sequentially (i.e., sequential administration). In some embodiments, the anordrin or analog thereof (such as anordrin) and the other agent (including the specific agents described herein) are administered simultaneously. The term "simultaneous administration," as used herein, means that the anordrin or analog thereof (such as anordrin) and the other agent are administered with a time separation of no more than about 15 minute(s), such as no more than about any of 10, 5, or 1 minutes. When the drugs are administered simultaneously, the anordrin or analog thereof (such as anordrin) and the other agent may be contained in the same composition (e.g., a composition comprising both the anordrin or analog thereof (such as anordrin) and the other agent, for example the pharmaceutical composition comprised herein) or in separate compositions (e.g., the anordrin or analog thereof (such as anordrin) and the other agent are contained in separate compositions).

In some embodiments, the anordrin or analog thereof (such as anordrin) and the other agent are administered sequentially. The term "sequential administration" as used herein means that the drug in the anordrin or analog thereof (such as anordrin) and the other agent are administered with a time separation of more than about 15 minutes, such as more than about any of 20, 30, 40, 50, 60 or more minutes. Either the anordrin or analog thereof (such as anordrin) or the other agent may be administered first. The anordrin or analog thereof (such as anordrin) and the other agent are contained in separate compositions, which may be contained in the same or different packages.

In some embodiments, the administration of the anordrin or analog thereof (such as anordrin) and the other agent are concurrent, i.e., the administration period of the anordrin or analog thereof (such as anordrin) and that of the other agent overlap with each other. In some embodiments, the anordrin or analog thereof (such as anordrin) is administered for at least one cycle (for example, at least any of 2, 3, or 4 cycles) prior to the administration of the other agent. In some embodiments, the other agent is administered for at least any of one, two, three, or four weeks. In some embodiments, the administrations of the anordrin or analog thereof (such as anordrin) and the other agent are initiated at about the same time (for example, within any one of 1, 2, 3, 4, 5, 6, or 7 days). In some embodiments, the administrations of the anordrin or analog thereof (such as anordrin) and the other agent are terminated at about the same time (for example, within any one of 1, 2, 3, 4, 5, 6, or 7 days). In some embodiments, the administration of the other agent continues (for example for about any one of 1, 2, 3, 4, 5, 6, 7, 8, 9, 10, 11, or 12 months) after the termination of the administration of the anordrin or analog thereof (such as anordrin). In some embodiments, the administration of the other agent is initiated after (for example after about any one of 1, 2, 3, 4, 5, 6, 7, 8, 9, 10, 11, or we months) the initiation of the administration of the anordrin or analog thereof (such as anordrin). In some embodiments, the administrations of the anordrin or analog thereof (such as anordrin) and the other agent are initiated and terminated at about the same time. In some embodiments, the administrations of the anordrin or analog thereof (such as anordrin) and the other agent are initiated at about the same time and the administration of the other agent continues (for example for about any one of 1, 2, 3, 4, 5, 6, 7, 8, 9, 10, 11, or 12 months) after the termination of the administration of the anordrin or analog thereof (such as anordrin). In some embodiments, the administration of the anordrin or analog thereof (such as anordrin) and the other agent stop at about the same time and the administration of the other agent is initiated after (for example after about any one of 1, 2, 3, 4, 5, 6, 7, 8, 9, 10, 11, or we months) the initiation of the administration of the anordrin or analog thereof (such as anordrin).

The dosing frequency of the anordrin or analog thereof (such as anordrin) and/or the other agent may be adjusted over the course of the treatment, based on the judgment of the administering physician. When administered separately, the anordrin or analog thereof (such as anordrin) and the other agent can be administered at different dosing frequency or intervals. For example, the anordrin or analog thereof (such as anordrin) can be administered weekly, while another agent can be administered more or less frequently. Various formulations and devices for achieving sustained release are known in the art. Exemplary dosing frequencies are further provided herein.

The anordrin or analog thereof (such as anordrin) and the other agent can be administered using the same route of administration or different routes of administration. Exemplary administration routes are further provided herein. In some embodiments (for both simultaneous and sequential administrations), the anordrin or analog thereof (such as anordrin) and the other agent are administered at a predetermined ratio. For example, in some embodiments, the ratio by weight of the anordrin or analog thereof (such as anordrin) and the other agent is about 1 to 1. In some embodiments, the weight ratio may be between about 0.001 to about 1 and about 1000 to about 1, or between about 0.01 to about 1 and 100 to about 1. In some embodiments, the ratio by weight of the anordrin or analog thereof (such as anordrin) and the other agent is less than about any of 100:1, 50:1, 30:1, 10:1, 9:1, 8:1, 7:1, 6:1, 5:1, 4:1, 3:1, 2:1, and 1:1 In some embodiments, the ratio by weight of the anordrin or analog thereof (such as anordrin) and the other agent is more than about any of 1:1, 2:1, 3:1, 4:1, 5:1, 6:1, 7:1, 8:1, 9:1, 30:1, 50:1, 100:1. Other ratios are contemplated.

The doses required for the anordrin or analog thereof (such as anordrin) and/or the other agent may (but not necessarily) be lower than what is normally required when each agent is administered alone. Thus, in some embodiments, a subtherapeutic amount of the drug in the anordrin or analog thereof (such as anordrin) and/or the other agent are administered. "Subtherapeutic amount" or "subtherapeutic level" refer to an amount that is less than therapeutic amount, that is, less than the amount normally used when the drug in the anordrin or analog thereof (such as anordrin) and/or the other agent are administered alone. The reduction may be reflected in terms of the amount administered at a given administration and/or the amount administered over a given period of time (reduced frequency).

In some embodiments, enough other agent is administered so as to allow reduction of the normal dose of the anordrin or analog thereof (such as anordrin) required to effect the same degree of treatment by at least about any of 5%, 10%, 20%, 30%, 50%, 60%, 70%, 80%, 90%, or more. In some embodiments, enough anordrin or analog thereof (such as anordrin) is administered so as to allow reduction of the normal dose of the other agent required to effect the same degree of treatment by at least about any of 5%, 10%, 20%, 30%, 50%, 60%, 70%, 80%, 90%, or more.

In some embodiments, the doses of both the anordrin or analog thereof (such as anordrin) and the other agent are reduced as compared to the corresponding normal dose of each when administered alone. In some embodiments, both the anordrin or analog thereof (such as anordrin) and the other agent are administered at a subtherapeutic, i.e., reduced, level. In some embodiments, the dose of the anordrin or analog thereof (such as anordrin) and/or the other agent is substantially less than the established maximum toxic dose (MTD). For example, the dose of the anordrin or analog thereof (such as anordrin) and/or the other agent is less than about 50%, 40%, 30%, 20%, or 10% of the MTD.

In some embodiments, the dose of anordrin or analog thereof (such as anordrin) and/or the dose of the other agent is higher than what is normally required when each agent is administered alone. For example, in some embodiments, the dose of the anordrin or analog thereof (such as anordrin) and/or the other agent is substantially higher than the established maximum toxic dose (MTD). For example, the dose of the anordrin or analog thereof (such as anordrin) and/or the other agent is more than about 50%, 40%, 30%, 20%, or 10% of the MTD of the agent when administered alone.

In some embodiments, the amount of a anordrin or analog thereof (such as anordrin) (alone or in combination with an other agent) is included in any of the following ranges: about 0.1 to about 0.5 mg, about 0.5 to about 5 mg, about 5 to about 10 mg, about 10 to about 15 mg, about 15 to about 20 mg, about 20 to about 25 mg, about 20 to about 50 mg, about 25 to about 50 mg, about 50 to about 75 mg, about 50 to about 100 mg, about 75 to about 100 mg, about 100 to about 125 mg, about 125 to about 150 mg, about 150 to about 175 mg, about 175 to about 200 mg, about 200 to about 225 mg, about 225 to about 250 mg, about 250 to about 300 mg, about 300 to about 350 mg, about 350 to about 400 mg, about 400 to about 450 mg, or about 450 to about 500 mg. In some embodiments, the amount of a anordrin or analog thereof (such as anordrin) (e.g., a unit dosage form) is in the range of about 5 mg to about 500 mg, such as about 30 mg to about 300 mg or about 50 mg to about 200 mg.

In some embodiments, the amount of the anordrin or analog thereof (such as anordrin) (alone or in combination with another agent) includes at least about any of 0.01 mg/kg, 0.05 mg/kg, 0.1 mg/kg, 0.25 mg/kg, 0.5 mg/kg, 1 mg/kg, 2.5 mg/kg, 3.5 mg/kg, 5 mg/kg, 6.5 mg/kg, 7.5 mg/kg, 10 mg/kg, 15 mg/kg or 20 mg/kg. In some embodiments, the amount of the anordrin or analog thereof (such as anordrin) (alone or in combination with another agent) includes at least about any of 0.01 mg/kg/day, 0.05 mg/kg/day, 0.1 mg/kg/day, 0.25 mg/kg/day, 0.5 mg/kg/day, 1 mg/kg/day, 2.5 mg/kg/day, 3.5 mg/kg/day, 5 mg/kg/day, 6.5 mg/kg/day, 7.5 mg/kg/day, 10 mg/kg/day, 15 mg/kg/day or 20 mg/kg/day.

In some embodiments, the amount of the other agent includes at least about any of 0.01 mg/kg, 0.05 mg/kg, 0.1 mg/kg, 0.25 mg/kg, 0.5 mg/kg, 1 mg/kg, 2.5 mg/kg, 3.5 mg/kg, 5 mg/kg, 6.5 mg/kg, 7.5 mg/kg, 10 mg/kg, 15 mg/kg or 20 mg/kg. In some embodiments, the amount of the anordrin or analog thereof (such as anordrin) (alone or in combination with another agent) includes at least about any of 0.01 mg/kg/day, 0.05 mg/kg/day, 0.1 mg/kg/day, 0.25 mg/kg/day, 0.5 mg/kg/day, 1 mg/kg/day, 2.5 mg/kg/day, 3.5 mg/kg/day, 5 mg/kg/day, 6.5 mg/kg/day, 7.5 mg/kg/day, 10 mg/kg/day, 15 mg/kg/day or 20 mg/kg/day.

Exemplary dosing frequencies for the anordrin or analog thereof (such as anordrin) (and for the other agent) include, but are not limited to, once every 2 weeks, once every 3 weeks, once every 4 weeks, once every 6 weeks, or once every 8 weeks. In some embodiments, the composition is administered at least about any of 1×, 2×, 3×, 4×, 5×, 6×, or 7× (i.e., daily) a week, or three times daily, two times daily. In some embodiments, the intervals between each administration are less than about any of 6 months, 3 months, 1 month, 20 days, 15 days, 12 days, 10 days, 9 days, 8 days, 7 days, 6 days, 5 days, 4 days, 3 days, 2 days, or 1 day. In some embodiments, the intervals between each administration are more than about any of 1 month, 2 months, 3 months, 4 months, 5 months, 6 months, 8 months, or 12 months. In some embodiments, there is no break in the dosing schedule. In some embodiments, the interval between each administration is no more than about a week.

The administration of the anordrin or analog thereof (such as anordrin) (and for the other agent) can be extended over an extended period of time, such as from about a month up to about seven years. In some embodiments, the composition is administered over a period of at least about any of 2, 3, 4, 5, 6, 7, 8, 9, 10, 11, 12, 18, 24, 30, 36, 48, 60, 72, or 84 months.

In some embodiments, the individual is treated for at least about any of one, two, three, four, five, six, seven, eight, nine, or ten treatment cycles.

The dosing frequency of the other agent can be the same or different from that of the anordrin or analog thereof (such as anordrin). Exemplary frequencies are provided above.

The anordrin or analog thereof (such as anordrin) (and the other agent) described herein can be administered to an individual (such as human) via various routes, including, for example, oral, intravenous, intra-arterial, intraperitoneal, intrapulmonary, inhalation, intravesicular, intramuscular, intra-tracheal, subcutaneous, intraocular, intrathecal, transmucosal, and transdermal. In some embodiments, sustained continuous release formulation of the composition may be used.

A combination of the administration configurations described herein can be used. The combination therapy methods described herein may be performed alone or in conjunction with another therapy, such as surgery, radiation, chemotherapy, immunotherapy, gene therapy, and the like. Additionally, a person having a greater risk of developing the proliferative disease may receive treatments to inhibit or and/or delay the development of the disease.

As will be understood by those of ordinary skill in the art, the appropriate doses of other agents will be approximately those already employed in clinical therapies wherein the other agent are administered alone or in combination with other agents. Variation in dosage will likely occur depending on the condition being treated. As described above, in some embodiments, the other agents may be administered at a reduced level.

Compositions, Kits, and Medicines

The invention also provides compositions (such as pharmaceutical compositions), medicine, kits, and unit dosages useful for methods described herein. Also provided are any use described herein whether in the context of use as a medicament and/or use for manufacture of a medicament.

The methods of the present application comprise administration of anordrin or analog thereof (such as anordrin). Suitable anordrin or analogs thereof are described in more details below.

The methods of the present application in some aspects comprise administration of raloxifene or functional equivalent thereof. "Functional equivalent thereof" used herein refers to compounds that functions through the same mechanism as raloxifene. For example, functional equivalents of raloxifene include, but are not limited to, lasofoxifene, bazedoxifene, arzoxifene, ormeloxifene, ospemifene, and levormeloxifene.

In another aspect, the method comprises administration of an aromatase inhibitor. "Aromatase inhibitor" refers to a class of agents that inhibit aromatase activity. Aromatase inhibitors have been used in the treatment of breast cancer and ovarian cancer in postmenopausal women to reduce increase of estrogen conversion during cycle with external testosterone. Suitable aromatase inhibitors include, but are not limited to, anastrozole (Arimidex), letrozole (Femara), exemestane (Aromasin), vorozole (Rivizor), formestane (Lentaron), and fadrozole (Afema).

In another aspect, there is provided a pharmaceutical composition comprising an anordrin or analog thereof (such as anordrin) and at least one other agent selected from the group consisting of tamoxifen, raloxifene or functional equivalent thereof, and an aromatase inhibitor. In some embodiments, there is provided a pharmaceutical composition comprising an anordrin or analog thereof (such as anordrin) and at least one other agent, wherein the other agent is tamoxifen. In some embodiments, there is provided a pharmaceutical composition comprising an anordrin or analog thereof (such as anordrin) and at least one other agent, wherein the other agent is raloxifene. In some embodiments, there is provided a pharmaceutical composition comprising an anordrin or analog thereof (such as anordrin) and at least one other agent, wherein the other agent is anastrozole.

In some embodiments, the pharmaceutical composition further comprises a lipid, which includes, but is not limited to, corn oil. The lipid can be present, for example, in the amount of about 1%-5% (w/w).

In some embodiments, the pharmaceutical composition further comprises protein (such as casein). Protein (such as casein) can be present, for example, in the amount of about 5%-50% (w/w).

In some embodiments, the ratio by weight of the anordrin or analog thereof (such as anordrin) and the other agent in the composition is about 1 to 1. In some embodiments, the weight ratio is between about 0.001 to about 1 and about 1000 to about 1, or between about 0.01 to about 1 and 100 to about 1. In some embodiments, the ratio by weight of the anordrin or analog thereof (such as anordrin) and the other agent is less than about any of 100:1, 50:1, 30:1, 10:1, 9:1, 8:1, 7:1, 6:1, 5:1, 4:1, 3:1, 2:1, and 1:1 In some embodiments, the ratio by weight of the anordrin or analog thereof (such as anordrin) and the other agent is more than about any of 1:1, 2:1, 3:1, 4:1, 5:1, 6:1, 7:1, 8:1, 9:1, 30:1, 50:1, 100:1. In some embodiments, the weight ratio of anordrin or analog thereof (such as anordrin) and the other agent in the composition is about 1:20 to about 20:1 (including for example about 10:1 to about 1:10, or about 1:10 to about 1:15).

The composition in some embodiments may be present in a unit dosage form (such as an oral unit dosage form). Suitable unit dosage forms include, but are not limited to, capsules, tablets, pills, caplets, gels, liquids (e.g., suspensions, solutions, emulsions), powders or other particulates, and so forth.

In another aspect, there are provided kits comprising anordrin or analog thereof (such as anordrin) and the other agent either in separate containers or in the same container. Kits of the invention include one or more containers comprising anordrin or analog thereof (such as anordrin) (or unit dosage forms and/or articles of manufacture) and/or at least one other agent, and in some embodiments, further comprise instructions for use in accordance with any of the methods described herein. The kit may further comprise a description of selection an individual suitable or treatment. Instructions supplied in the kits of the invention are typically written instructions on a label or package insert (e.g., a paper sheet included in the kit), but machine-readable instructions (e.g., instructions carried on a magnetic or optical storage disk) are also acceptable.

In some embodiments, the kit comprises a) an effective amount an anordrin or analog thereof (such as anordrin), and b) an effective amount of at least one other agent selected from the group consisting of tamoxifen, raloxifene or functional equivalent thereof, and an aromatase inhibitor. In some embodiments, the kit comprises: a) an effective amount an anordrin or analog thereof (such as anordrin), and b) an effective amount of at least one other agent selected from the group consisting of tamoxifen, raloxifene or functional equivalent thereof, and an aromatase inhibitor, and c) instructions for administering the anordrin or analog thereof (such as anordrin) and the other agents simultaneously, sequentially, or concurrently for treatment of cancer (or other uses described herein).

The anordrin or analog thereof (such as anordrin) and the other agents can be present in separate containers or in a single container. It is understood that the kit may comprise one distinct composition or two or more compositions wherein one composition comprises anordrin or analog thereof (such as anordrin) and one composition comprises another agent.

The kits of the invention are in suitable packaging. Suitable packaging include, but is not limited to, vials, bottles, jars, flexible packaging (e.g., sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

The instructions relating to the use of the anordrin or analog thereof (such as anordrin) generally include information as to dosage, dosing schedule, and route of administration for the intended treatment. The containers may be unit doses, bulk packages (e.g., multi-dose packages) or sub-unit doses. For example, kits may be provided that contain sufficient dosages of the anordrin or analog thereof (such as anordrin) (such as anordrin or analog thereof (such as anordrin)) as disclosed herein to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the anordrin or analog thereof (such as anordrin) and pharmaceutical compositions and instructions for use and packaged in quantities sufficient for storage and use in pharmacies, for example, hospital pharmacies and compounding pharmacies. Anordrin and its analogs The present application provides methods and compositions comprising anordrin or its analogs.

In some embodiments, the anordrin or analog therefore has the structure of Formula (I),

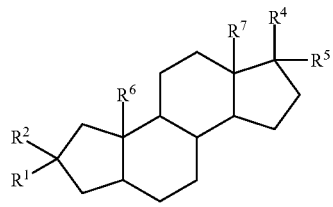

(I)

wherein
$R^1$ is hydroxyl or —O(CO)$R^{1a}$ wherein $R^{1a}$ is $C_1$-$C_4$alkyl;
$R^2$ is

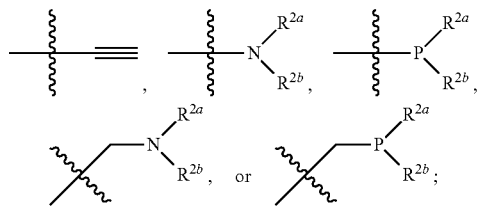

wherein $R^{2a}$ and $R^{2b}$ are independently hydrogen, $C_1$-$C_{12}$alkyl, $C_2$-$C_{12}$alkenyl, or phenyl;
$R^4$ is hydroxyl or —O(CO)$R^{4a}$, wherein $R^{4a}$ is $C_1$-$C_4$alkyl;
$R^5$ is

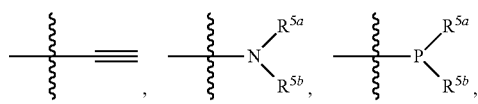

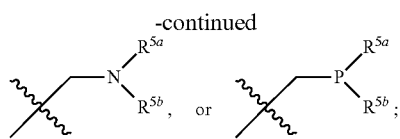

wherein $R^{5a}$ and $R^{5b}$ are independently hydrogen, $C_1$-$C_{12}$alkyl, $C_2$-$C_{12}$alkenyl, or phenyl;
$R^6$ is $C_1$-$C_6$alkyl or $C_2$-$C_6$alkenyl; and
$R^7$ is $C_1$-$C_6$alkyl or $C_2$-$C_6$alkenyl;
or a pharmaceutically acceptable salt thereof.

In some embodiments, Formula (I) is Formula (Ia):

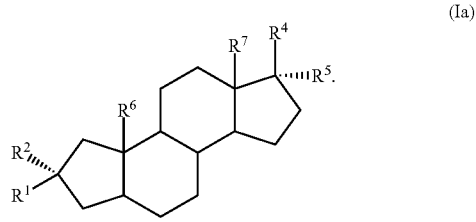

(Ia)

In some embodiments, Formula (I) is Formula (Ib):

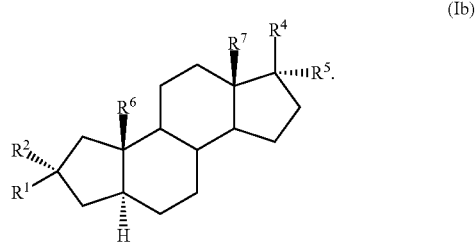

(Ib)

In some embodiments, $R^1$ is —O(CO)$R^{1a}$, wherein $R^{1a}$ is $C_1$-$C_4$alkyl (e.g., $C_1$alkyl, $C_2$alkyl, $C_3$alkyl, or $C_4$alkyl). In some embodiments, $R^{1a}$ is $C_1$-$C_4$alkyl, such as $C_1$-$C_3$alkyl or $C_1$-$C_2$alkyl. In some embodiments, $R^{1a}$ is methyl. In some embodiments, $R^{1a}$ is ethyl. In some embodiments, $R^1$ is hydroxyl.

In some embodiments, $R^2$ is

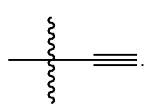

In some embodiments, $R^2$ is

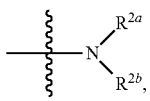

wherein $R^{2a}$ and $R^{2b}$ are independently hydrogen, $C_1$-$C_{12}$alkyl (e.g., $C_1$alkyl, $C_2$alkyl, $C_3$alkyl, $C_4$alkyl, $C_5$alkyl, $C_6$alkyl, $C_7$alkyl, $C_8$alkyl, $C_9$alkyl, $C_{10}$alkyl, $C_{11}$alkyl, or $C_{12}$alkyl), $C_2$-$C_{12}$alkenyl (e.g., $C_2$alkenyl, $C_3$alkenyl, $C_4$alkenyl, $C_5$alkenyl, $C_6$alkenyl, $C_7$alkenyl, $C_8$alkenyl, $C_9$alkenyl, $C_{10}$alkenyl, $C_{11}$alkenyl, or $C_{12}$alkenyl), or phenyl.

In some embodiments, $R^2$ is

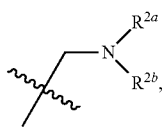

wherein $R^{2a}$ and $R^{2b}$ are independently hydrogen, $C_1$-$C_{12}$alkyl (e.g., $C_1$alkyl, $C_2$alkyl, $C_3$alkyl, $C_4$alkyl, $C_5$alkyl, $C_6$alkyl, $C_7$alkyl, $C_8$alkyl, $C_9$alkyl, $C_{10}$alkyl, $C_{11}$alkyl, or $C_{12}$alkyl), $C_2$-$C_{12}$alkenyl (e.g., $C_2$alkenyl, $C_3$alkenyl, $C_4$alkenyl, $C_5$alkenyl, $C_6$alkenyl, $C_7$alkenyl, $C_8$alkenyl, $C_9$alkenyl, $C_{10}$alkenyl, $C_{11}$alkenyl, or $C_{12}$alkenyl), or phenyl.

In some embodiments, $R^2$ is

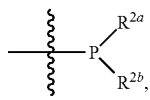

wherein $R^{2a}$ and $R^{2b}$ are independently hydrogen, $C_1$-$C_{12}$alkyl (e.g., $C_1$alkyl, $C_2$alkyl, $C_3$alkyl, $C_4$alkyl, $C_5$alkyl, $C_6$alkyl, $C_7$alkyl, $C_8$alkyl, $C_9$alkyl, $C_{10}$alkyl, $C_{11}$alkyl, or $C_{12}$alkyl), $C_2$-$C_{12}$alkenyl (e.g., $C_2$alkenyl, $C_3$alkenyl, $C_4$alkenyl, $C_5$alkenyl, $C_6$alkenyl, $C_7$alkenyl, $C_8$alkenyl, $C_9$alkenyl, $C_{10}$alkenyl, $C_{11}$alkenyl, or $C_{12}$alkenyl), or phenyl.

In some embodiments, $R^2$ is

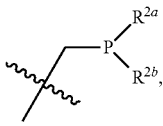

wherein $R^{2a}$ and $R^{2b}$ are independently hydrogen, $C_1$-$C_{12}$alkyl (e.g., $C_1$alkyl, $C_2$alkyl, $C_3$alkyl, $C_4$alkyl, $C_5$alkyl, $C_6$alkyl, $C_7$alkyl, $C_8$alkyl, $C_9$alkyl, $C_{10}$alkyl, $C_{11}$alkyl, or $C_{12}$alkyl), $C_2$-$C_{12}$alkenyl (e.g., $C_2$alkenyl, $C_3$alkenyl, $C_4$alkenyl, $C_5$alkenyl, $C_6$alkenyl, $C_7$alkenyl, $C_8$alkenyl, $C_9$alkenyl, $C_{10}$alkenyl, $C_{11}$alkenyl, or $C_{12}$alkenyl), or phenyl.

In some embodiments, $R^{2a}$ and $R^{2b}$ are independently hydrogen, $C_1$-$C_{12}$alkyl, or $C_2$-$C_{12}$alkenyl. In some embodiments, $R^{2a}$ and $R^{2b}$ are independently hydrogen or $C_1$-$C_{12}$alkyl. In some embodiments, $R^{2a}$ and $R^{2b}$ are independently hydrogen or $C_2$-$C_{12}$alkenyl.

In some embodiments, $R^{2a}$ and $R^{2b}$ are independently hydrogen, $C_1$-$C_4$alkyl, or $C_2$-$C_4$alkenyl. In some embodiments, $R^{2a}$ and $R^{2b}$ are independently hydrogen or $C_1$-$C_4$alkyl. In some embodiments, $R^{2a}$ and $R^{2b}$ are independently hydrogen or $C_2$-$C_4$alkenyl.

In some embodiments, $R^{2a}$ and $R^{2b}$ are independently hydrogen, $C_{10}$-$C_{12}$alkyl, or $C_{10}$-$C_{12}$alkenyl. In some embodiments, $R^{2a}$ and $R^{2b}$ are independently hydrogen or $C_{10}$-$C_{12}$alkyl. In some embodiments, $R^{2a}$ and $R^{2b}$ are independently hydrogen or $C_{10}$-$C_{12}$alkenyl.

In some embodiments, $R^{2a}$ is hydrogen and $R^{2b}$ is $C_1$-$C_{12}$alkyl, such as $C_1$-$C_4$alkyl, $C_1$-$C_3$alkyl, $C_1$-$C_2$alkyl, or $C_{10}$-$C_{12}$alkyl. In some embodiments, $R^{2a}$ is hydrogen and $R^{2b}$ is $C_2$-$C_{12}$alkenyl, such as $C_2$-$C_4$alkenyl, $C_2$-$C_3$alkenyl, $C_2$alkenyl, or $C_{10}$-$C_{12}$alkenyl.

In some embodiments, $R^4$ is —O(CO)$R^{1a}$, wherein $R^{4a}$ is $C_1$-$C_4$alkyl (e.g., $C_1$alkyl, $C_2$alkyl, $C_3$alkyl, or $C_4$alkyl). In some embodiments, $R^{4a}$ is $C_1$-$C_4$alkyl, such as $C_1$-$C_3$alkyl or $C_1$-$C_2$alkyl. In some embodiments, $R^{4a}$ is methyl. In some embodiments, $R^{4a}$ is ethyl. In some embodiments, $R^4$ is hydroxyl.

In some embodiments, $R^5$ is

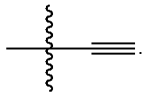

In some embodiments, $R^5$ is

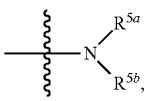

wherein $R^{5a}$ and $R^{5b}$ are independently hydrogen, $C_1$-$C_{12}$alkyl (e.g., $C_1$alkyl, $C_2$alkyl, $C_3$alkyl, $C_4$alkyl, $C_5$alkyl, $C_6$alkyl, $C_7$alkyl, $C_8$alkyl, $C_9$alkyl, $C_{10}$alkyl, $C_{11}$alkyl, or $C_{12}$alkyl), $C_2$-$C_{12}$alkenyl (e.g., $C_2$alkenyl, $C_3$alkenyl, $C_4$alkenyl, $C_5$alkenyl, $C_6$alkenyl, $C_7$alkenyl, $C_8$alkenyl, $C_9$alkenyl, $C_{10}$alkenyl, $C_{11}$alkenyl, or $C_{12}$alkenyl), or phenyl.

In some embodiments, $R^5$ is

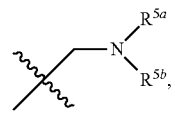

wherein $R^{5a}$ and $R^{5b}$ are independently hydrogen, $C_1$-$C_{12}$alkyl (e.g., $C_1$alkyl, $C_2$alkyl, $C_3$alkyl, $C_4$alkyl, $C_5$alkyl, $C_6$alkyl, $C_7$alkyl, $C_8$alkyl, $C_9$alkyl, $C_{10}$alkyl, $C_{11}$alkyl, or $C_{12}$alkyl), $C_2$-$C_{12}$alkenyl (e.g., $C_2$alkenyl, $C_3$alkenyl, $C_4$alkenyl, $C_5$alkenyl, $C_6$alkenyl, $C_7$alkenyl, $C_8$alkenyl, $C_9$alkenyl, $C_{10}$alkenyl, $C_{11}$alkenyl, or $C_{12}$alkenyl), or phenyl.

In some embodiments, $R^5$ is

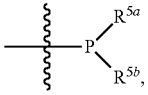

wherein $R^{5a}$ and $R^{5b}$ are independently hydrogen, $C_1$-$C_{12}$alkyl (e.g., $C_1$alkyl, $C_2$alkyl, $C_3$alkyl, $C_4$alkyl, $C_5$alkyl, $C_6$alkyl, $C_7$alkyl, $C_8$alkyl, $C_9$alkyl, $C_{10}$alkyl, $C_{11}$alkyl, or $C_{12}$alkyl), $C_2$-$C_{12}$alkenyl (e.g., $C_2$alkenyl, $C_3$alkenyl, $C_4$alkenyl, $C_5$alkenyl, $C_6$alkenyl, $C_7$alkenyl, $C_8$alkenyl, $C_9$alkenyl, $C_{10}$alkenyl, $C_{11}$alkenyl, or $C_{12}$alkenyl), or phenyl.

In some embodiments, $R^5$ is

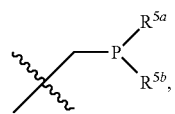

wherein $R^{5a}$ and $R^{5b}$ are independently hydrogen, $C_1$-$C_{12}$alkyl (e.g., $C_1$alkyl, $C_2$alkyl, $C_3$alkyl, $C_4$alkyl, $C_5$alkyl, $C_6$alkyl, $C_7$alkyl, $C_8$alkyl, $C_9$alkyl, $C_{10}$alkyl, $C_{11}$alkyl, or $C_{12}$alkyl), $C_2$-$C_{12}$alkenyl (e.g., $C_2$alkenyl, $C_3$alkenyl, $C_4$alkenyl, $C_5$alkenyl, $C_6$alkenyl, $C_7$alkenyl, $C_8$alkenyl, $C_9$alkenyl, $C_{10}$alkenyl, $C_{11}$alkenyl, or $C_{12}$alkenyl), or phenyl.

In some embodiments, $R^{5a}$ and $R^{5b}$ are independently hydrogen, $C_1$-$C_{12}$alkyl, or $C_2$-$C_{12}$alkenyl. In some embodiments, $R^{5a}$ and $R^{5b}$ are independently hydrogen or $C_1$-$C_{12}$alkyl. In some embodiments, $R^{5a}$ and $R^{5b}$ are independently hydrogen or $C_2$-$C_{12}$alkenyl.

In some embodiments, $R^{5a}$ and $R^{5b}$ are independently hydrogen, $C_1$-$C_4$alkyl, or $C_2$-$C_4$alkenyl. In some embodiments, $R^{5a}$ and $R^{5b}$ are independently hydrogen or $C_1$-$C_4$alkyl. In some embodiments, $R^{5a}$ and $R^{5b}$ are independently hydrogen or $C_2$-$C_4$alkenyl.

In some embodiments, $R^{5a}$ and $R^{5b}$ are independently hydrogen, $C_{10}$-$C_{12}$alkyl, or $C_{10}$-$C_{12}$alkenyl. In some embodiments, $R^{5a}$ and $R^{5b}$ are independently hydrogen or $C_{10}$-$C_{12}$alkyl. In some embodiments, $R^{5a}$ and $R^{5b}$ are independently hydrogen or $C_{10}$-$C_{12}$alkenyl.

In some embodiments, $R^{5a}$ is hydrogen and $R^{5b}$ is $C_1$-$C_{12}$alkyl, such as $C_1$-$C_4$alkyl, $C_1$-$C_3$alkyl, $C_1$-$C_2$alkyl, or $C_{10}$-$C_{12}$alkyl. In some embodiments, $R^{5a}$ is hydrogen and $R^{5b}$ is $C_2$-$C_2$alkenyl, such as $C_2$-$C_4$alkenyl, $C_2$-$C_3$alkenyl, $C_2$alkenyl, or $C_{10}$-$C_{12}$alkenyl.

In some embodiments, $R^6$ is $C_1$-$C_6$alkyl (e.g., $C_1$alkyl, $C_2$alkyl, $C_3$alkyl, $C_4$alkyl, $C_5$alkyl, or $C_6$alkyl). In some embodiments, $R^6$ is $C_1$-$C_6$alkyl, such as $C_1$-$C_3$alkyl or $C_1$-$C_2$alkyl. In some embodiments, $R^6$ is methyl. In some embodiments, $R^6$ is ethyl. In some embodiments, $R^6$ is $C_2$-$C_6$alkenyl (e.g., $C_2$alkenyl, $C_3$alkenyl, $C_4$alkenyl, $C_5$alkenyl, or $C_6$alkenyl).

In some embodiments, $R^7$ is $C_1$-$C_6$alkyl (e.g., $C_1$alkyl, $C_2$alkyl, $C_3$alkyl, $C_4$alkyl, $C_5$alkyl, or $C_6$alkyl). In some embodiments, $R^7$ is $C_1$-$C_6$alkyl, such as $C_1$-$C_3$alkyl, $C_1$-$C_2$alkyl, or $C_3$-$C_6$alkyl. In some embodiments, $R^7$ is methyl. In some embodiments, $R^7$ is ethyl. In some embodiments, $R^7$ is $C_1$-$C_2$alkyl. In some embodiments, $R^7$ is $C_3$-$C_6$alkyl.

In some embodiments, the compounds may have any one or more of the following structural features. In some embodiments, $R^1$ and $R^4$ are same moiety and $R^2$ and $R^5$ are the same moiety.
a) $R^1$ is-O(CO)$R^{1a}$, wherein $R^{1a}$ is $C_1$-$C_4$alkyl;
b) $R^4$ is O(CO)$R^{4a}$ wherein $R^{4a}$ is $C_1$-$C_4$alkyl;
c) $R^2$ is

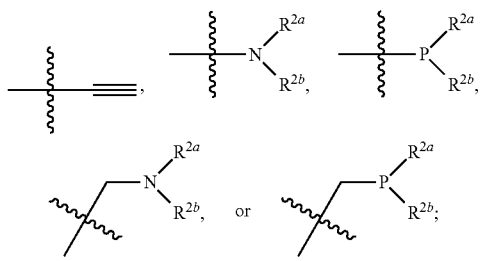

wherein $R^{2a}$ and $R^{2b}$ are independently hydrogen, $C_1$-$C_{12}$alkyl (e.g., $C_1$-$C_4$alkyl or $C_{10}$-$C_{12}$alkyl), $C_2$-$C_{12}$alkenyl (e.g., $C_2$-$C_4$alkenyl or $C_{10}$-$C_{12}$alkenyl), or phenyl; and d) $R^5$ is

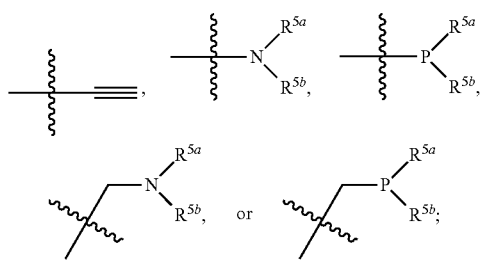

wherein $R^{5a}$ and $R^{5b}$ are independently hydrogen, $C_1$-$C_{12}$alkyl (e.g., $C_1$-$C_4$alkyl or $C_{10}$-$C_{12}$alkyl), $C_2$-$C_{12}$alkenyl (e.g., $C_2$-$C_4$alkenyl or $C_{10}$-$C_{12}$alkenyl), or phenyl.

In some embodiments, the compounds may have any one or more of the following structural features. In some embodiments, $R^1$ and $R^4$ are same moiety.
a) $R^1$ is —O(CO)$R^{1a}$, wherein $R^{1a}$ is $C_1$-$C_4$alkyl;
b) $R^4$ is —O(CO)$R^{4a}$, wherein $R^{4a}$ is $C_1$-$C_4$alkyl;
c) $R^2$ is

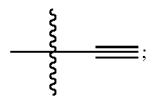

and
d) $R^5$ is

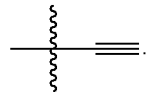 [SMILES: *C#C]

In some embodiments, the compounds may have any one or more of the following structural features. In some embodiments, $R^1$ and $R^4$ are same moiety and $R^2$ and $R^5$ are the same moiety.
a) $R^1$ is-O(CO)$R^{1a}$, wherein $R^1$ is $C_1$-$C_4$alkyl;
b) $R^4$ is —O(CO)$R^{4a}$ wherein $R^{4a}$ is $C_1$-$C_4$alkyl;
c) $R^2$ is

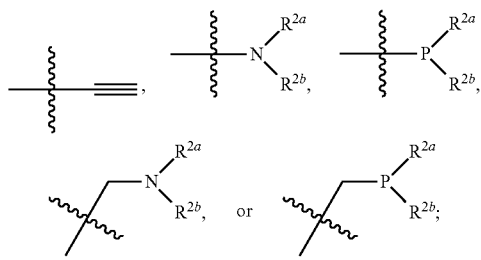

wherein $R^{2a}$ and $R^{2b}$ are independently hydrogen, $C_1$-$C_4$alkyl, $C_2$-$C_4$alkenyl, or phenyl; and
d) $R^5$ is

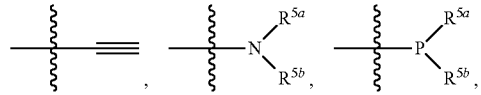

-continued

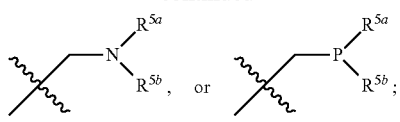

wherein $R^{5a}$ and $R^{5b}$ are independently hydrogen, $C_1$-$C_4$alkyl, $C_2$-$C_4$alkenyl, or phenyl.

In some embodiments, the compounds may have any one or more of the following structural features. In some embodiments, $R^1$ and $R^4$ are same moiety and $R^2$ and $R^5$ are the same moiety.

a) $R^1$ is —O(CO)$R^{1a}$, wherein $R^{1a}$ is $C_1$-$C_4$alkyl;
b) $R^4$ is —O(CO)$R^{4a}$, wherein $R^{4a}$ is $C_1$-$C_4$alkyl;
c) $R^2$ is

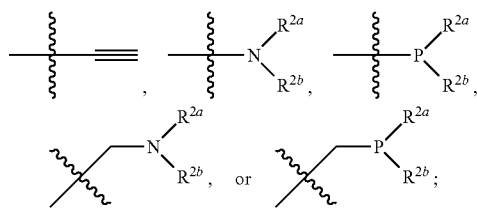

wherein $R^{2a}$ and $R^{2b}$ are independently hydrogen, $C_{10}$-$C_{12}$alkyl, $C_{10}$-$C_{12}$alkenyl, or phenyl; and
d) $R^5$ is

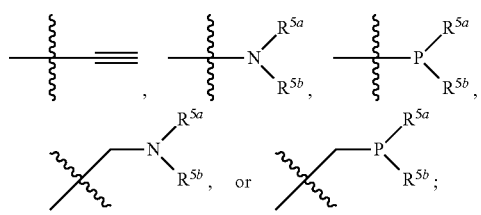

wherein $R^{5a}$ and $R^{5b}$ are independently hydrogen, $C_{10}$-$C_{12}$alkyl, $C_{10}$-$C_{12}$alkenyl, or phenyl.

In some embodiments, the compounds may have any one or more of the following structural features. In some embodiments, $R^2$ and $R^5$ are the same moiety.

a) $R^2$ is

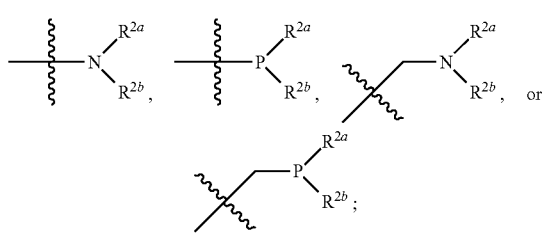

wherein $R^{2a}$ and $R^{2b}$ are independently hydrogen, $C_1$-$C_{12}$alkyl (e.g., $C_1$-$C_4$alkyl or $C_{10}$-$C_{12}$alkyl), $C_2$-$C_{12}$alkenyl (e.g., $C_2$-$C_4$alkenyl or $C_{10}$-$C_{12}$alkenyl), or phenyl;

b) $R^5$ is

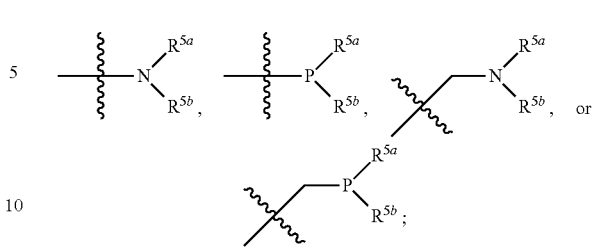

wherein $R^{5a}$ and $R^{5b}$ are independently hydrogen, $C_1$-$C_{12}$alkyl (e.g., $C_1$-$C_4$alkyl or $C_{10}$-$C_{12}$alkyl), $C_2$-$C_{12}$alkenyl (e.g., $C_2$-$C_4$alkenyl or $C_{10}$-$C_{12}$alkenyl), or phenyl;
c) $R^1$ is hydroxyl; and
d) $R^4$ is hydroxyl.

In some embodiments, the compounds may have any one or more of the following structural features. In some embodiments, $R^2$ and $R^5$ are the same moiety.

a) $R^2$ is

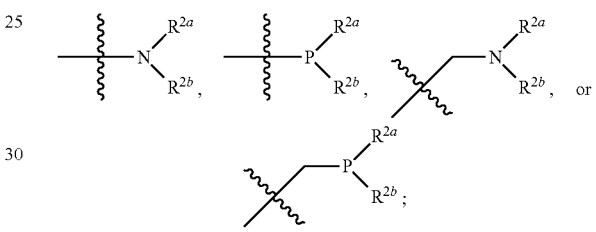

wherein $R^{2a}$ and $R^{2b}$ are independently hydrogen, $C_1$-$C_4$alkyl, $C_2$-$C_4$alkenyl, or phenyl;

b) $R^5$ is

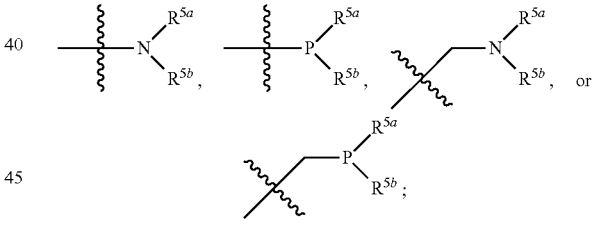

wherein $R^{5a}$ and $R^{5b}$ are independently hydrogen, $C_1$-$C_4$alkyl, $C_2$-$C_4$alkenyl, or phenyl;
c) $R^1$ is hydroxyl; and
d) $R^4$ is hydroxyl.

In some embodiments, the compounds may have any one or more of the following structural features. In some embodiments $R^2$ and $R^5$ are the same moiety.

a) $R^2$ is

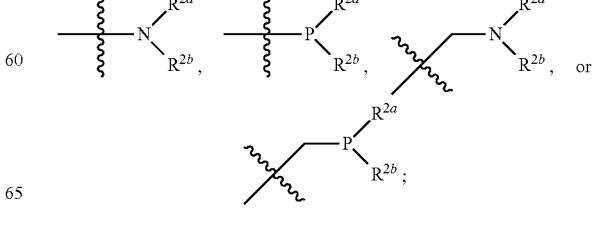

wherein $R^{2a}$ and $R^{2b}$ are independently hydrogen, $C_{10}$-$C_{12}$alkyl, $C_{10}$-$C_{12}$alkenyl, or phenyl;

b) $R^5$ is

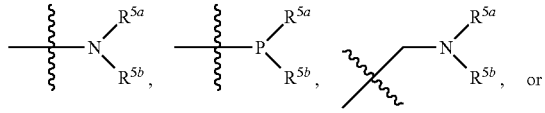

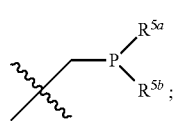

wherein $R^{5a}$ and $R^{5b}$ are independently hydrogen, $C_{10}$-$C_{12}$alkyl, $C_{10}$-$C_{12}$alkenyl, or phenyl;

c) $R^1$ is hydroxyl; and d) $R^4$ is hydroxyl.

In some embodiments, the compounds may have any one or more of the following structural features:

a) $R^6$ is $C_1$-$C_6$alkyl (e.g., methyl or ethyl); and b) $R^7$ is methyl or ethyl.

In some embodiments, the anordrin or analog thereof has the structure of Formula (II),

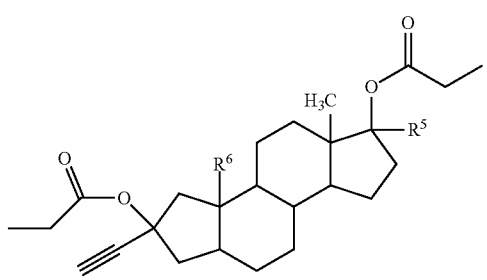

wherein
$R^5$ is

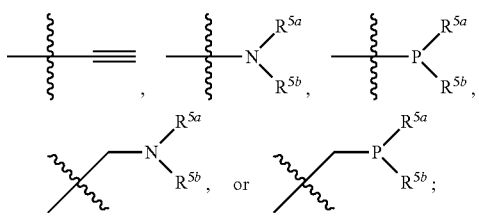

wherein $R^{5a}$ and $R^{5b}$ are independently hydrogen, $C_1$-$C_{12}$alkyl, $C_2$-$C_{12}$alkenyl, or phenyl; and $R^6$ is $C_1$-$C_6$alkyl or $C_2$-$C_6$alkenyl;

or a pharmaceutically acceptable salt thereof.

In some embodiments, Formula (II) is Formula (IIa):

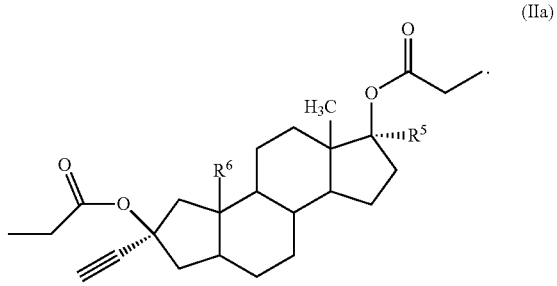

In some embodiments, Formula (II) is Formula (IIb):

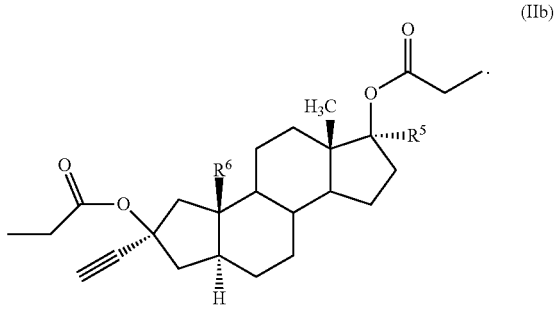

In some embodiments, $R^5$ is

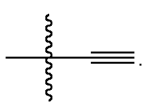

In some embodiments, $R^5$ is

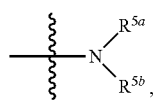

wherein $R^{5a}$ and $R^{5b}$ are independently hydrogen, $C_1$-$C_{12}$alkyl (e.g., $C_1$alkyl, $C_2$alkyl, $C_3$alkyl, $C_4$alkyl, $C_5$alkyl, $C_6$alkyl, $C_7$alkyl, $C_8$alkyl, $C_9$alkyl, $C_{10}$alkyl, $C_{11}$alkyl, or $C_{12}$alkyl), $C_2$-$C_{12}$alkenyl (e.g., $C_2$alkenyl, $C_3$alkenyl, $C_4$alkenyl, $C_5$alkenyl, $C_6$alkenyl, $C_7$alkenyl, $C_8$alkenyl, $C_9$alkenyl, $C_{10}$alkenyl, $C_{11}$alkenyl, or $C_{12}$alkenyl), or phenyl.

In some embodiments, $R^5$ is

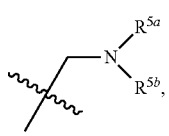

wherein $R^{5a}$ and $R^{5b}$ are independently hydrogen, $C_1$-$C_{12}$alkyl (e.g., $C_1$alkyl, $C_2$alkyl, $C_3$alkyl, $C_4$alkyl, $C_5$alkyl, $C_6$alkyl, $C_7$alkyl, $C_8$alkyl, $C_9$alkyl, $C_{10}$alkyl, $C_{11}$alkyl, or $C_{12}$alkyl), $C_2$-$C_{12}$alkenyl (e.g., $C_2$alkenyl, $C_3$alkenyl, $C_4$alkenyl, $C_5$alkenyl, $C_6$alkenyl, $C_7$alkenyl, $C_8$alkenyl, $C_9$alkenyl, $C_{10}$alkenyl, $C_{11}$alkenyl, or $C_{12}$alkenyl), or phenyl.

In some embodiments, $R^5$ is

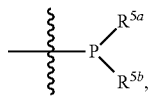

wherein $R^{5a}$ and $R^{5b}$ are independently hydrogen, $C_1$-$C_{12}$alkyl (e.g., $C_1$alkyl, $C_2$alkyl, $C_3$alkyl, $C_4$alkyl, $C_5$alkyl, $C_6$alkyl, $C_7$alkyl, $C_8$alkyl, $C_9$alkyl, $C_{10}$alkyl, $C_{11}$alkyl, or $C_{12}$alkyl), $C_2$-$C_{12}$alkenyl (e.g., $C_2$alkenyl, $C_3$alkenyl, $C_4$alkenyl, $C_5$alkenyl, $C_6$alkenyl, $C_7$alkenyl, $C_8$alkenyl, $C_9$alkenyl, $C_{10}$alkenyl, $C_{11}$alkenyl, or $C_{12}$alkenyl), or phenyl.

In some embodiments, $R^5$ is

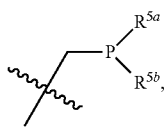

wherein $R^{5a}$ and $R^{5b}$ are independently hydrogen, $C_1$-$C_{12}$alkyl (e.g., $C_1$alkyl, $C_2$alkyl, $C_3$alkyl, $C_4$alkyl, $C_5$alkyl, $C_6$alkyl, $C_7$alkyl, $C_8$alkyl, $C_9$alkyl, $C_{10}$alkyl, $C_{11}$alkyl, or $C_{12}$alkyl), $C_2$-$C_{12}$alkenyl (e.g., $C_2$alkenyl, $C_3$alkenyl, $C_4$alkenyl, $C_5$alkenyl, $C_6$alkenyl, $C_7$alkenyl, $C_8$alkenyl, $C_9$alkenyl, $C_{10}$alkenyl, $C_{11}$alkenyl, or $C_{12}$alkenyl), or phenyl.

In some embodiments, $R^{5a}$ and $R^{5b}$ are independently hydrogen, $C_1$-$C_{12}$alkyl, or $C_2$-$C_{12}$alkenyl. In some embodiments, $R^{5a}$ and $R^{5b}$ are independently hydrogen or $C_1$-$C_{12}$alkyl. In some embodiments, $R^{5a}$ and $R^{5b}$ are independently hydrogen or $C_2$-$C_{12}$alkenyl.

In some embodiments, $R^{5a}$ and $R^{5b}$ are independently hydrogen, $C_1$-$C_4$alkyl, or $C_2$-$C_4$alkenyl. In some embodiments, $R^{5a}$ and $R^{5b}$ are independently hydrogen or $C_1$-$C_4$alkyl. In some embodiments, $R^{5a}$ and $R^{5b}$ are independently hydrogen or $C_2$-$C_4$alkenyl.

In some embodiments, $R^{5a}$ and $R^{5b}$ are independently hydrogen, $C_{10}$-$C_{12}$alkyl, or $C_{10}$-$C_{12}$alkenyl. In some embodiments, $R^{5a}$ and $R^{5b}$ are independently hydrogen or $C_{10}$-$C_{12}$alkyl. In some embodiments, $R^{5a}$ and $R^{5b}$ are independently hydrogen or $C_{10}$-$C_{12}$alkenyl.

In some embodiments, $R^{5a}$ is hydrogen and $R^{5b}$ is $C_1$-$C_{12}$alkyl, such as $C_1$-$C_4$alkyl, $C_1$-$C_3$alkyl, $C_1$-$C_2$alkyl, or $C_{10}$-$C_{12}$alkyl. In some embodiments, $R^5$ is hydrogen and $R^5$ is $C_2$-$C_2$alkenyl, such as $C_2$-$C_4$alkenyl, $C_2$-$C_3$alkenyl, $C_2$alkenyl, or $C_{10}$-$C_{12}$alkenyl.

In some embodiments, $R^6$ is $C_1$-$C_6$alkyl (e.g., $C_1$alkyl, $C_2$alkyl, $C_3$alkyl, $C_4$alkyl, $C_5$alkyl, or $C_6$alkyl). In some embodiments, $R^6$ is $C_1$-$C_6$alkyl, such as $C_1$-$C_3$alkyl or $C_1$-$C_2$alkyl. In some embodiments, $R^6$ is methyl. In some embodiments, $R^6$ is ethyl. In some embodiments, $R^6$ is $C_2$-$C_6$alkenyl (e.g., $C_2$alkenyl, $C_3$alkenyl, $C_4$alkenyl, $C_5$alkenyl, or $C_6$alkenyl).

In some embodiments, the anordrin or analog therefore has a structure of Formula (III),

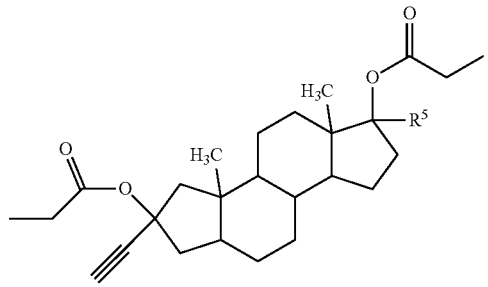

wherein
$R^5$ is

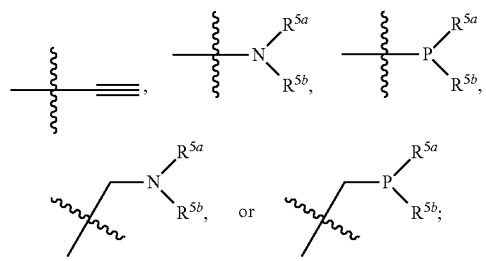

wherein $R^{5a}$ and $R^{5b}$ are independently hydrogen, $C_1$-$C_{12}$alkyl, $C_2$-$C_{12}$alkenyl, or phenyl;

or a pharmaceutically acceptable salt thereof.

In some embodiments, Formula (III) is Formula (IIIa):

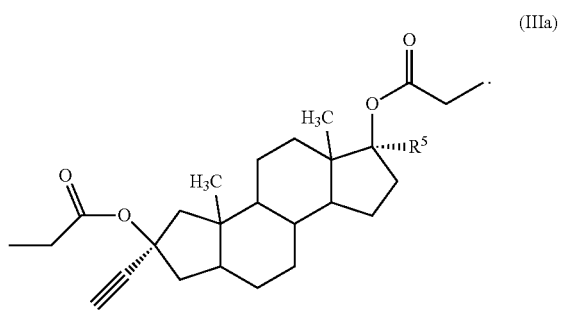

In some embodiments, Formula (III) is Formula (IIIb):

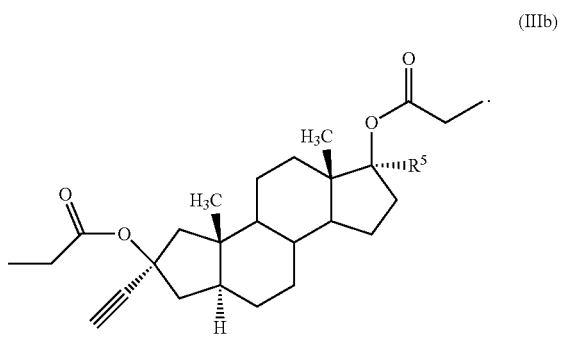

In some embodiments, $R^5$ is

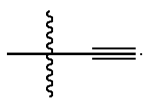

In some embodiments, $R^5$ is

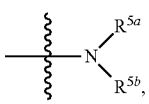

wherein $R^{5a}$ and $R^{5b}$ are independently hydrogen, $C_1$-$C_{12}$alkyl (e.g., $C_1$alkyl, $C_2$alkyl, $C_3$alkyl, $C_4$alkyl, $C_5$alkyl, $C_6$alkyl, $C_7$alkyl, $C_8$alkyl, $C_9$alkyl, $C_{10}$alkyl, $C_{11}$alkyl, or $C_{12}$alkyl), $C_2$-$C_{12}$alkenyl (e.g., $C_2$alkenyl, $C_3$alkenyl, $C_4$alkenyl, $C_5$alkenyl, $C_6$alkenyl, $C_7$alkenyl, $C_8$alkenyl, $C_9$alkenyl, $C_{10}$alkenyl, $C_{11}$alkenyl, or $C_{12}$alkenyl), or phenyl.

In some embodiments, $R^5$ is

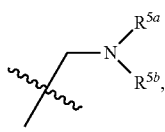

wherein $R^{5a}$ and $R^{5b}$ are independently hydrogen, $C_1$-$C_{12}$alkyl (e.g., $C_1$alkyl, $C_2$alkyl, $C_3$alkyl, $C_4$alkyl, $C_5$alkyl, $C_6$alkyl, $C_7$alkyl, $C_8$alkyl, $C_9$alkyl, $C_{10}$alkyl, $C_{11}$alkyl, or $C_{12}$alkyl), $C_2$-$C_{12}$alkenyl (e.g., $C_2$alkenyl, $C_3$alkenyl, $C_4$alkenyl, $C_5$alkenyl, $C_6$alkenyl, $C_7$alkenyl, $C_8$alkenyl, $C_9$alkenyl, $C_{10}$alkenyl, $C_{11}$alkenyl, or $C_{12}$alkenyl), or phenyl.

In some embodiments, $R^5$ is

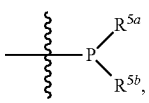

wherein $R^{5a}$ and $R^{5b}$ are independently hydrogen, $C_1$-$C_{12}$alkyl (e.g., $C_1$alkyl, $C_2$alkyl, $C_3$alkyl, $C_4$alkyl, $C_5$alkyl, $C_6$alkyl, $C_7$alkyl, $C_8$alkyl, $C_9$alkyl, $C_{10}$alkyl, $C_{11}$alkyl, or $C_{12}$alkyl), $C_2$-$C_{12}$alkenyl (e.g., $C_2$alkenyl, $C_3$alkenyl, $C_4$alkenyl, $C_5$alkenyl, $C_6$alkenyl, $C_7$alkenyl, $C_8$alkenyl, $C_9$alkenyl, $C_{10}$alkenyl, $C_{11}$alkenyl, or $C_{12}$alkenyl), or phenyl.

In some embodiments, $R^5$ is

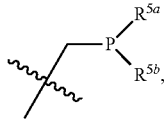

wherein $R^{5a}$ and $R^{5b}$ are independently hydrogen, $C_1$-$C_{12}$alkyl (e.g., $C_1$alkyl, $C_2$alkyl, $C_3$alkyl, $C_4$alkyl, $C_5$alkyl, $C_6$alkyl, $C_7$alkyl, $C_8$alkyl, $C_9$alkyl, $C_{10}$alkyl, $C_{11}$alkyl, or $C_{12}$alkyl), $C_2$-$C_{12}$alkenyl (e.g., $C_2$alkenyl, $C_3$alkenyl, $C_4$alkenyl, $C_5$alkenyl, $C_6$alkenyl, $C_7$alkenyl, $C_8$alkenyl, $C_9$alkenyl, $C_{10}$alkenyl, $C_{11}$alkenyl, or $C_{12}$alkenyl), or phenyl.

In some embodiments, $R^{5a}$ and $R^{5b}$ are independently hydrogen, $C_1$-$C_{12}$alkyl, or $C_2$-$C_{12}$alkenyl. In some embodiments, $R^{5a}$ and $R^{5b}$ are independently hydrogen or $C_1$-$C_{12}$alkyl. In some embodiments, $R^{5a}$ and $R^{5b}$ are independently hydrogen or $C_2$-$C_{12}$alkenyl.

In some embodiments, $R^{5a}$ and $R^{5b}$ are independently hydrogen, $C_1$-$C_4$alkyl, or $C_2$-$C_4$alkenyl. In some embodiments, $R^{5a}$ and $R^{5b}$ are independently hydrogen or $C_1$-$C_4$alkyl. In some embodiments, $R^{5a}$ and $R^{5b}$ are independently hydrogen or $C_2$-$C_4$alkenyl.

In some embodiments, $R^{5a}$ and $R^{5b}$ are independently hydrogen, $C_{10}$-$C_{12}$alkyl, or $C_{10}$-$C_{12}$alkenyl. In some embodiments, $R^{5a}$ and $R^{5b}$ are independently hydrogen or $C_{10}$-$C_{12}$alkyl. In some embodiments, $R^{5a}$ and $R^{5b}$ are independently hydrogen or $C_{10}$-$C_{12}$alkenyl.

In some embodiments, $R^5$ is hydrogen and $R^5$ is $C_1$-$C_{12}$alkyl, such as $C_1$-$C_4$alkyl, $C_1$-$C_3$alkyl, $C_1$-$C_2$alkyl, or $C_{10}$-$C_{12}$alkyl. In some embodiments, $R^{5a}$ is hydrogen and $R^{5b}$ is $C_2$-$C_{12}$alkenyl, such as $C_2$-$C_4$alkenyl, $C_2$-$C_3$alkenyl, $C_2$alkenyl, or $C_{10}$-$C_{12}$alkenyl.

In some embodiments, the anordrin or analog thereof has the structure of Formula (IV),

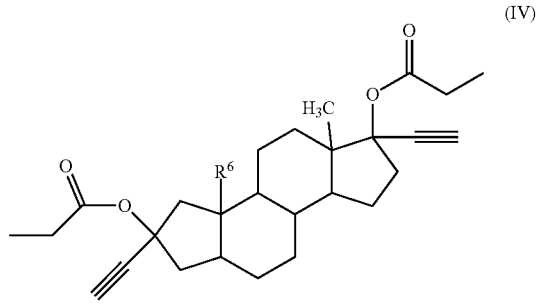

wherein $R^6$ is $C_1$-$C_6$alkyl or $C_2$-$C_6$alkenyl;
or a pharmaceutically acceptable salt thereof.

In some embodiments, Formula (IV) is Formula (IVa):

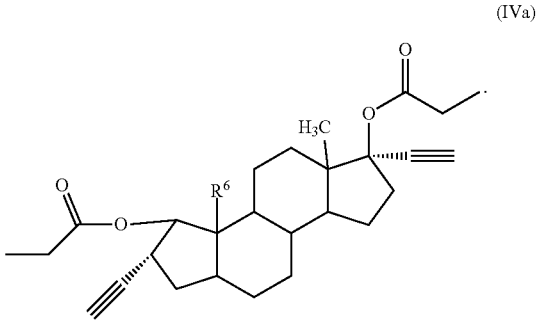

In some embodiments, Formula (IV) is Formula (IVa):

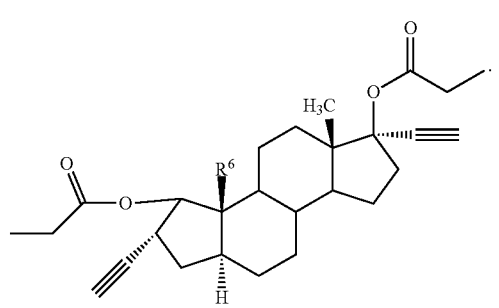

(IVa)

In some embodiments, $R^6$ is $C_1$-$C_6$alkyl (e.g., $C_1$alkyl, $C_2$alkyl, $C_3$alkyl, $C_4$alkyl, $C_5$alkyl, or $C_6$alkyl). In some embodiments, $R^6$ is $C_1$-$C_6$alkyl, such as $C_1$-$C_3$alkyl or $C_1$-$C_2$alkyl. In some embodiments, $R^6$ is methyl. In some embodiments, $R^6$ is ethyl. In some embodiments, $R^6$ is $C_2$-$C_6$alkenyl (e.g., $C_2$alkenyl, $C_3$alkenyl, $C_4$alkenyl, $C_5$alkenyl, or $C_6$alkenyl).

In some embodiments, the anordrin or analog thereof is anordrin. In some embodiments, the anordrin or analog thereof is a compound having a structure depicted below.

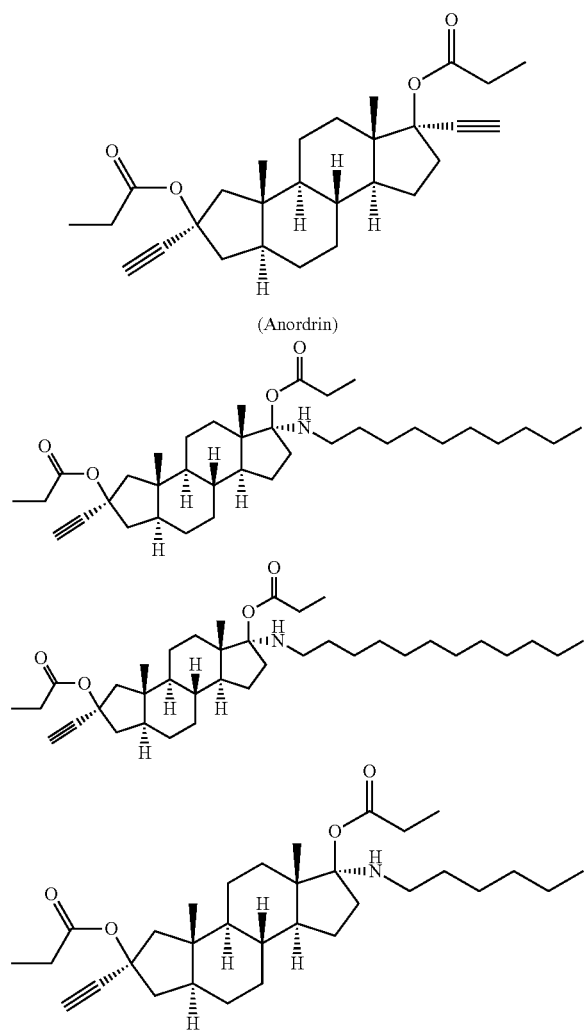

(Anordrin)

-continued

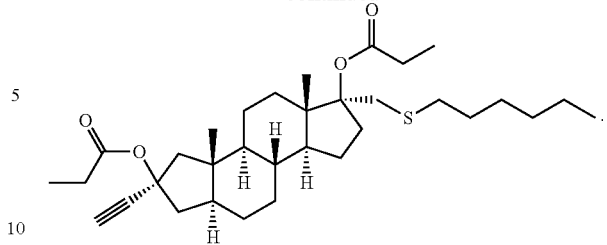

Those skilled in the art will recognize that several embodiments are possible within the scope and spirit of this invention. The invention will now be described in greater detail by reference to the following non-limiting examples. The following examples further illustrate the invention but, of course, should not be construed as in any way limiting its scope.

EXAMPLES

Example 1

Two estrogen-binding complexes, 4S and 8S, named with respect to the rate of ultracentrifugation sedimentation, were reported in uterine cytosol by Mehta et al (18). Anordiol, the unesterified and active metabolite of anordrin or analog thereof (such as anordrin), was found to preferentially bind the 8S complex with an affinity of approximately 2×105 M−1. In contrast, tamoxifen was found to bind both estrogen-binding complexes. The selective binding of anordrin or analog thereof (such as anordrin) with only one of the estrogen-binding uterine cytosolic complexes suggests that anordrin or analog thereof (such as anordrin) may modulate specific biological functions regulated by estrogen. There are currently two known pathways modulated by estrogen to regulate specific biological functions. We first tested whether anordrin or analog thereof (such as anordrin) was involved in the classical pathway of estrogen modulation. The ER-α ligand binding domain was expressed as a GST fusion protein (GST-ER-α-LBD) in $E.$ $coli$ and purified using glutathione beads. The binding affinities of anordrin or analog thereof (such as anordrin), tamoxifen and E2 to the ER-α LBD were compared using a 3H-E2 competition assay. It was found that 50 nM anordrin or analog thereof (such as anordrin) could not inhibit the binding of 0.5 nM 3H-E2 to 2 μg GST-ER-α-LBD. In contrast, the same concentration of either tamoxifen or E2 blocked over 60 percent of 3H-E2 binding to GST-ER-α LBD (FIG. 1A). Based on these results, we postulated that anordrin or analog thereof (such as anordrin) is not involved in regulating gene expression through the classical pathway of estrogen signaling.

Figure 1C:
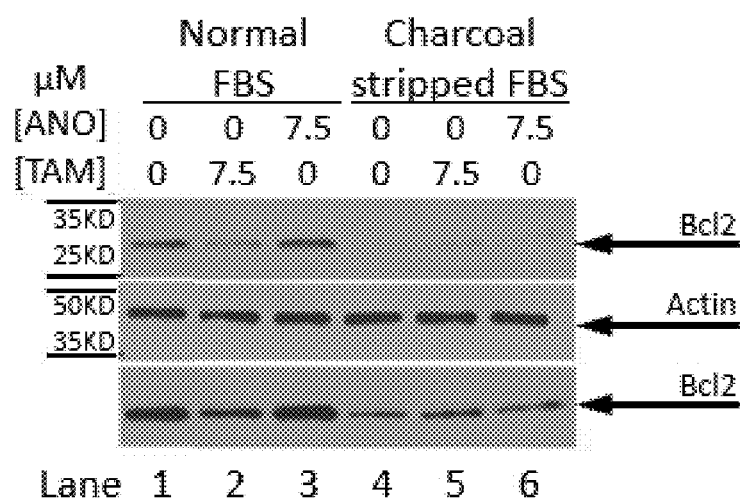
Figure 6:
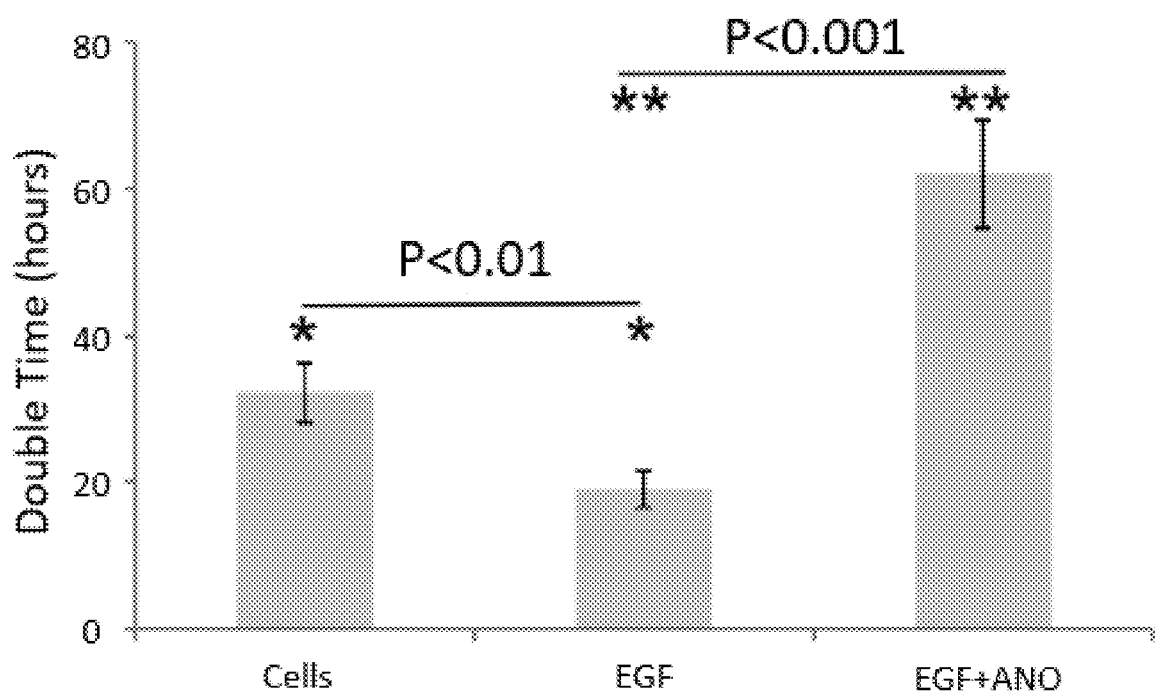
FIG. 6: Anordrin or analog thereof (such as anordrin) (7.5 μM) blocks EGF (10 ng/ml) induced cell growth in T47D cells.

Bcl-2 is a key member of the anti-apoptosis family of proteins. Its overexpression has been linked to many kinds of cancers in humans. The Bcl-2 promoter contains an ERE sequence, and Bcl-2 mRNA expression in MCF-7 cells has been found to be positively regulated by E2 and inhibited by tamoxifen (19). In agreement with Nehra's results, we found that the expression level of Bcl-2 protein was enhanced by estrogen (FIG. 1C, Lane 1 and 4), and 7.5 μM tamoxifen was found to inhibit Bcl-2 expression (FIG. 1C, lane 2). In contrast, the expression level of either Bcl-2 mRNA (data not shown) or protein (FIG. 1C, Lane 3) was not affected in MCF-7 cells treated with 7.5 μM anordrin or analog thereof (such as anordrin). Neither tamoxifen nor anordrin or analog thereof (such as anordrin) were found to affect Bcl-2 protein expression in cells cultured in medium using charcoal-stripped FBS in phenol red free DMEM medium (FIG. 1C, lane 5 and 6, respectively). The expression of BRCA1 mRNA has also been reported to be under the control of estrogen in MCF-7 cells (20). We further demonstrated that anordrin or analog thereof (such as anordrin) did not significantly affect the mRNA level of BRCA1 as measured using RT-qPCR in MCF-7 cells, while tamoxifen significantly inhibited the synthesis of BRCA1 mRNAs under the same conditions (FIG. 13B, column 2 and 4). These results further support that anordrin or analog thereof (such as anordrin) is not involved in the classic pathway of estrogen regulation. Interestingly, while anordrin or analog thereof (such as anordrin) did not appear to modulate gene transcription through classic ER pathways, we did find that 7.5 µM anordrin was able to inhibit MCF-7 cell growth by more than 50% (FIG. 13A, column 1, row 1 and 2). Furthermore, treatment of T47D cells with 7.5 µM anordrin or analog thereof (such as anordrin) not only blocked the increase in cell growth induced by 10 ng/ml EGF, but resulted in a further decrease below basal levels (FIG. 6).

Figure 13C:
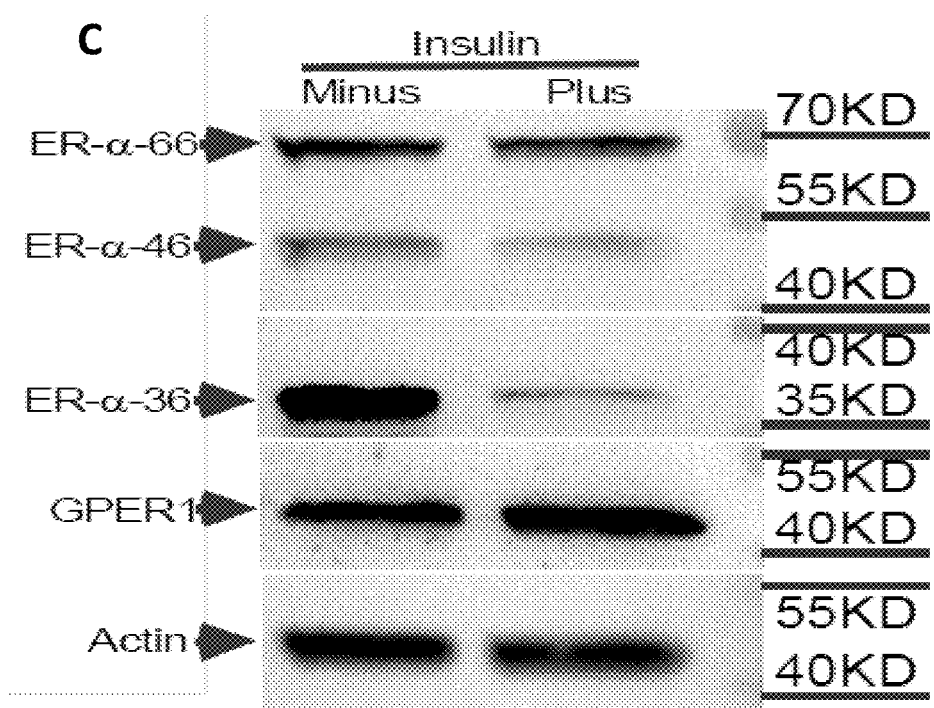

Insulin (IL) binds to insulin receptor (IR), stimulating the phosphorylation of insulin receptor substrate (IRS) through the insulin like growth factor receptor 1 (IGFR1) pathway. Phosphorylated IRS interacts with estrogen-ER complex, which can then translocate into the nucleus to regulate RNA transcription through the estrogen classical pathway. The proliferation of MCF-7 cells is modulated by IL, and the sensitivity of these cells to tamoxifen was found to be increased after IL was temporarily removed from culture medium (21) or when IRS expression was transiently knocked down using IRS-specific siRNA (22). Thus the IL-IRS-IGFR1-ER pathway plays an important role in the regulation of MCF-7 proliferation. Interruption of the IL-IRS-IGFR1-ER pathway should lead to the proliferation of MCF-7 cells being much more dependent on MIES. Consequently, the tamoxifen sensitivity of MCF-7 cells with disruption in the IL-IRS-ER pathway would be decreased, while the response to modulators of MIES would be increased. To test this hypothesis we induced MCF-7 cells in IL-free medium for two months. Drug sensitivity of cell growth was tested by counting the cell number after 144 h of inoculation (FIG. 13A). The data on IC50 of MCF-7 cell growth indicate that IL enhances the sensitivity of MCF-7 cells to tamoxifen (column2), while decreasing the sensitivity to anordrin or analog thereof (such as anordrin) (column 1). Moreover, the presence of 200 nM anordrin in the culture medium did not affect the ability of tamoxifen to inhibit MCF-7 cell growth (column2-row1 vs row4). As expression of ER-α-36 in MCF-7 cells increased in response to removal of insulin from the culture media, the expression levels of GPER1 and ER-α-66 did not change (FIG. 13C). These results further illustrate that the activity of anordrin is independent of the classical pathway. Furthermore, they suggest that anordrin may inhibit MCF-7 cell growth through inhibition of the MIES pathway, especially such as ER-α-36 pathway.

Figure 2A:
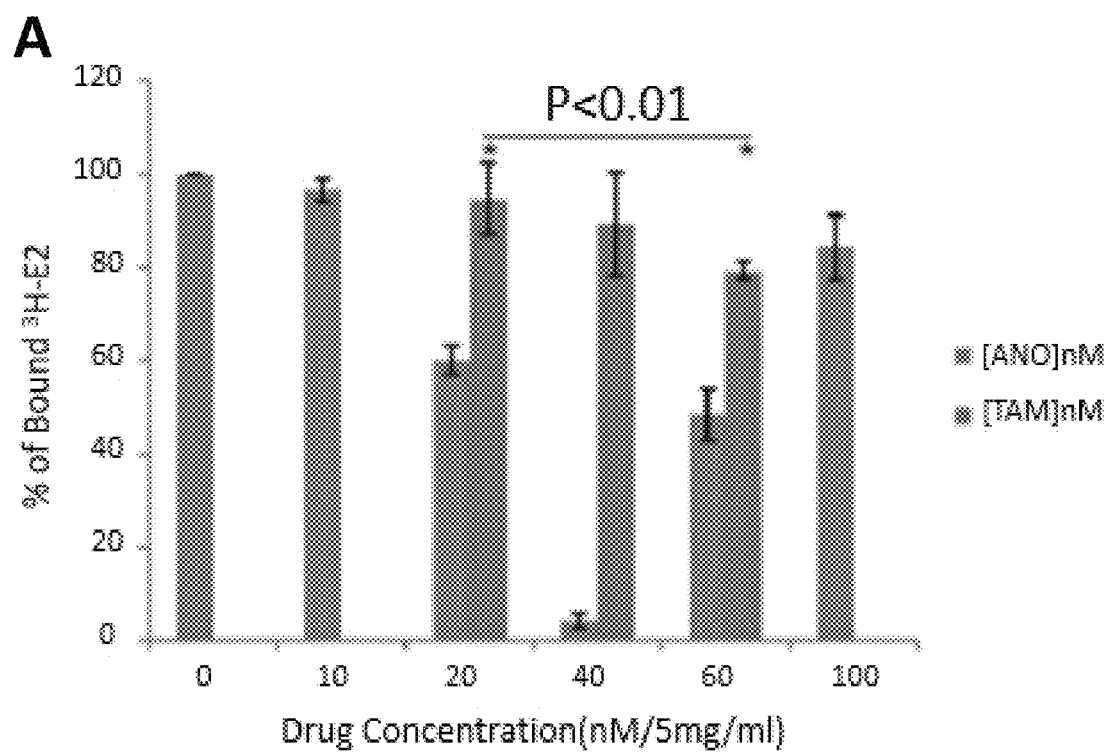
FIGS. 2A-2H: Anordrin or analog thereof (such as anordrin) blocks $^3$H-E2 binding to ER-α-36 expressed in HEK-293 cells and inhibits MDA-MB-231 cell growth and migration through the distribution of integrin β1 onto plasma membrane.
Figure 2B:
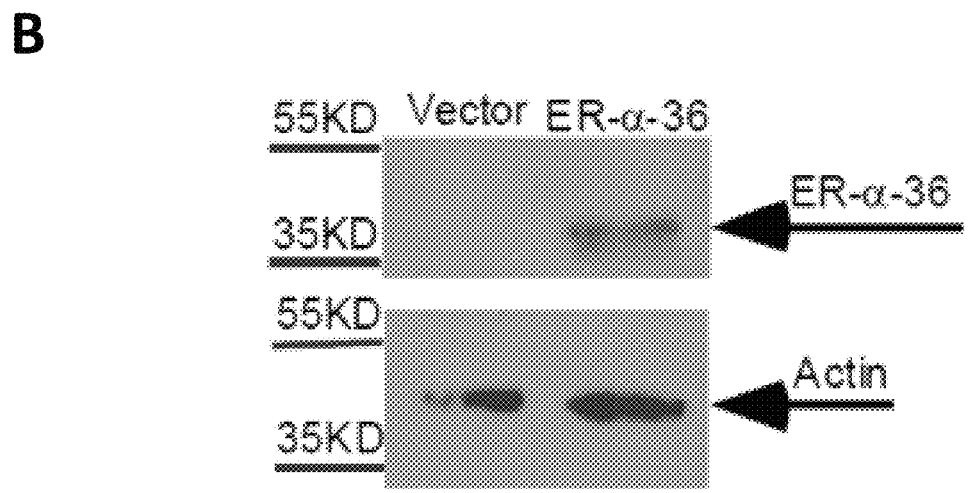
Figure 20:
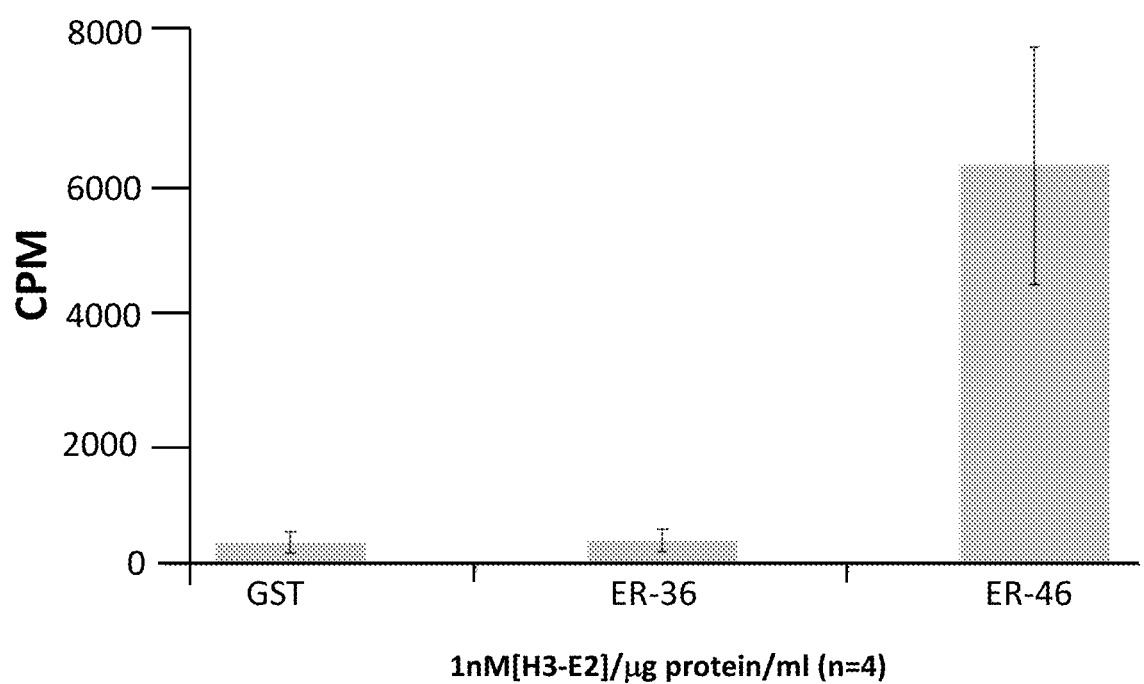
FIG. 20: $^3$H-E2 does not bind to soluble ER-α-36.

MIESs effect their regulation of cell proliferation, migration, cell-cell junction and matrix, and energy metabolism through a series of scaffold protein complexes. ER-α association with the plasma membrane is facilitated by palmitoylation at residue C447 in the LBD. ER-α-36 is a truncated ER-α variant, retaining the palmitoylation motif (445-453) and possessing a unique C-terminal 27 amino acid sequence in place of the typical 140 amino acids (456-595) of full-length ER-α (1). Since ER-α-36 possesses a partial LBD and predominantly localizes to plasma membrane and cytosol, it may have impaired estrogen binding, resulting in loss of the modulating ability of the estrogen classical pathway. To verify this, we measured the binding affinity of 3H-E2 with GST-ER-α-36 expressed and purified from E. coli. The results indicate that GST-ER-α-36 expressed from E. coli does not bind to 3H-E2 (FIG. 20). In contrast, 3H-E2 does bind to GST-ER-α-46, which has a full length ER-α-LBD. We next confirmed that ER-α-36 expressed in HEK 293 cells binds to 3H-E2 with a similar affinity (Kd≈1.9 nM) as found by Kang (23, data not shown). Interestingly, anordrin displayed a biphasic effect on 3H-E2 binding to ER-α-36, blocking 3H-E2 binding to ER-α-36 at low concentrations and facilitating binding at higher concentrations (FIG. 2A). Taken together, our data in light of the published studies on ER-α-36 suggest that it may be exclusively involved in the MIES pathway. We proceeded to make use of ER-α-36 to study the physiological consequences of MIES modulation by E2 and SERMs.

Figure 2C:
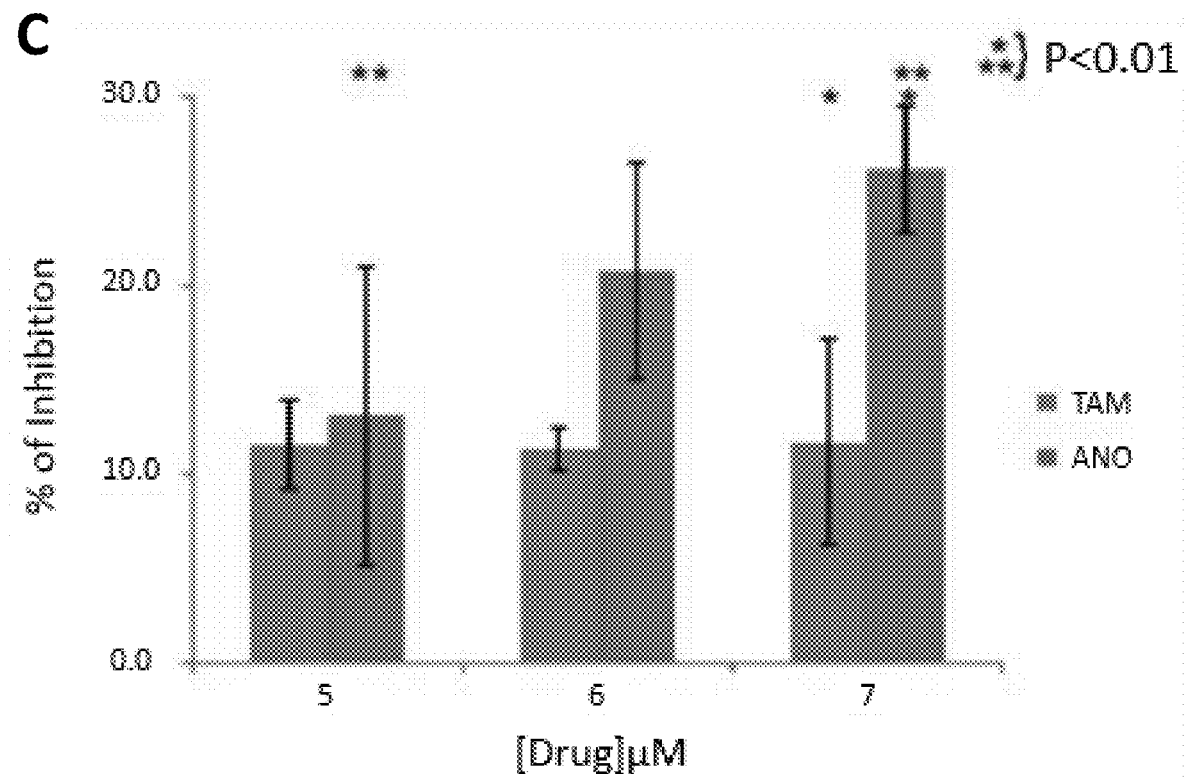
Figure 2D:
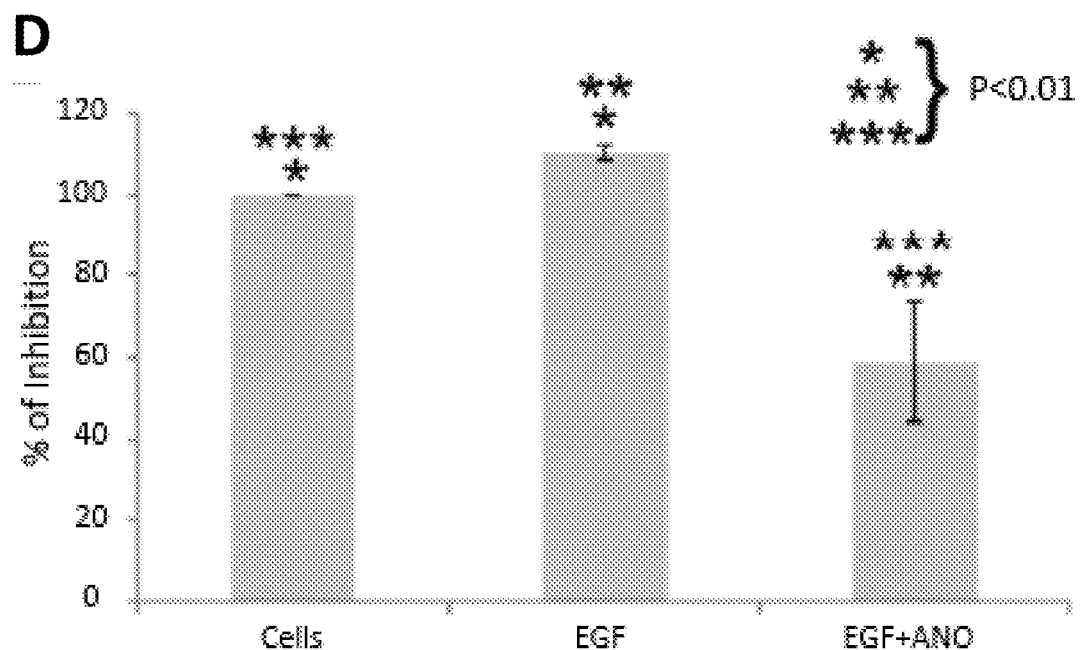
Figure 7A:
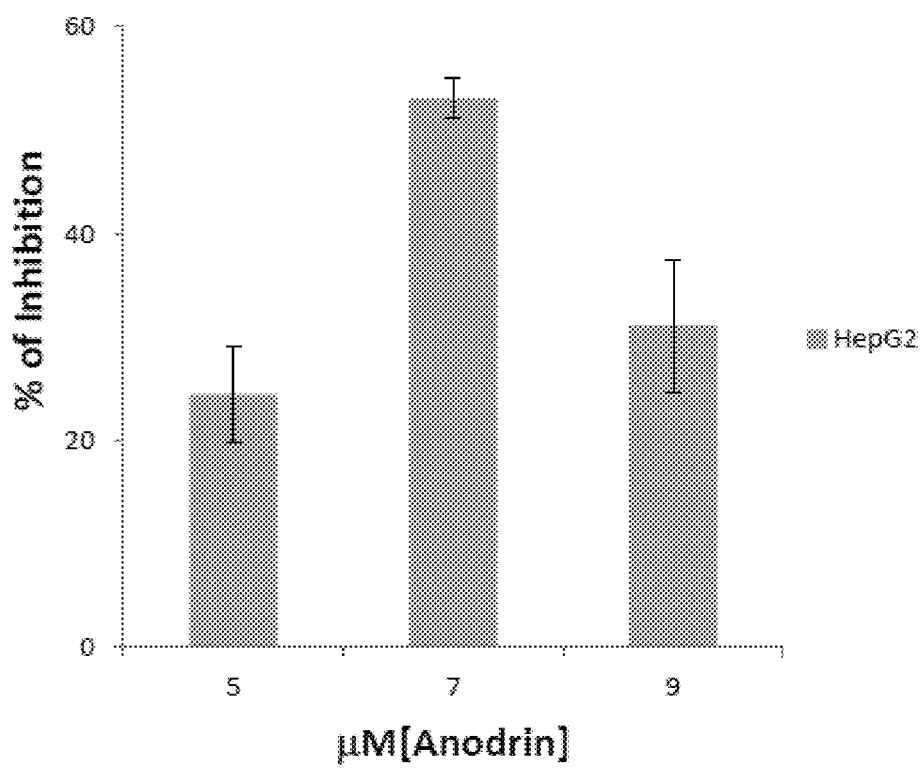
FIGS. 7A-7B: Anordrin or analog thereof (such as anordrin) inhibits HepG2 cell growth and induces phosphorylation of ERK.
Figure 7B:
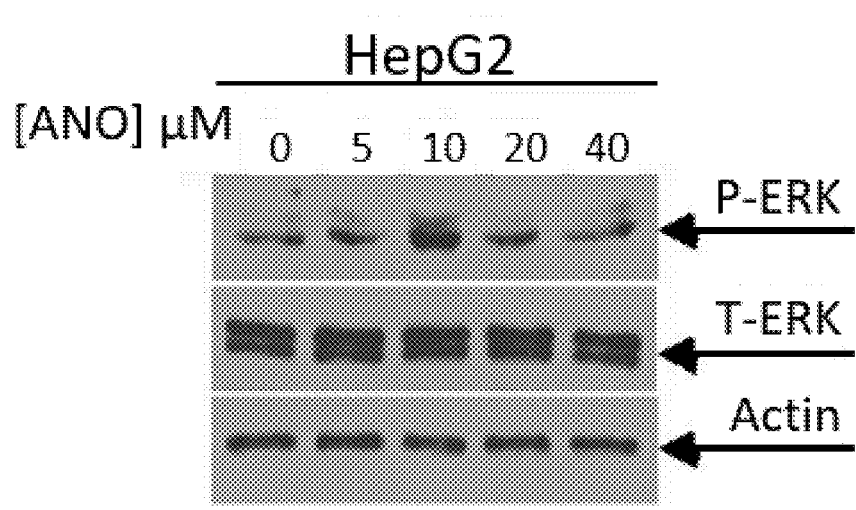
Figure 14A:
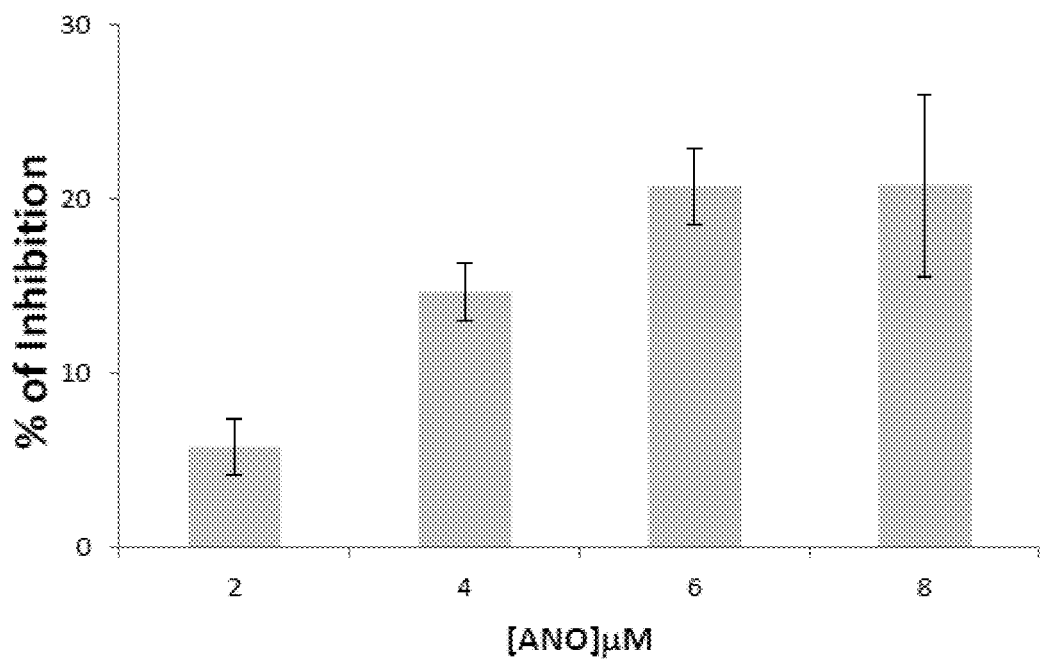
FIGS. 14A-14B: Anordrin or analog thereof (such as anordrin) inhibits Hec1A and Ishikawa cell growth.
Figure 14B:
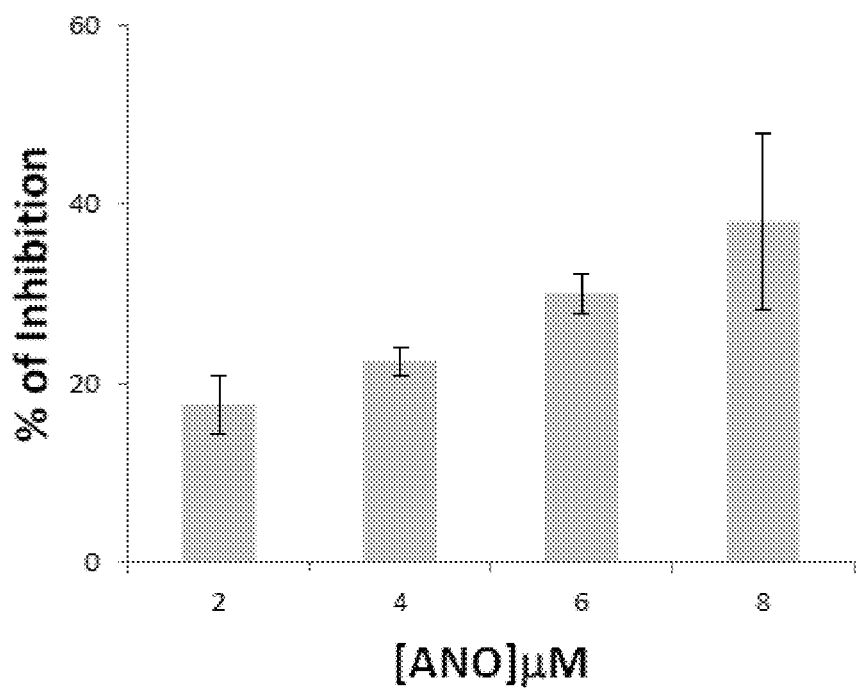

ER-α-36 is a unique and highly expressed ER-α variant in MDA-MB-231 and Hec1A cells and was demonstrated to regulate cell proliferation through the modulation of MAPK/ERK (1/2) pathways (23). We examined the sensitivity of MDA-MB-231 to anordrin in terms of cell growth. Our cell counting results indicate that 6 µM anordrin inhibits MDA-MB-231 cell growth significantly, while tamoxifen treatment has no effect (FIG. 2C). Anordrin treatment was also found to inhibit the proliferation of both Hec1A and Ishikawa cells at doses ranging from 2-8 µM (FIGS. 14A-14B). Additionally, anordrin treatment of HepG2 cells showed inhibition of cell growth characterized by a biphasic dose response, with intermediate concentrations around 7 µM showing the greatest degree of inhibition (FIG. 7A). Phosphorylation of ERK in HepG2 cells showed a similar non-monotonic dose response to anordrin treatment, with maximal phosphorylation occurring at a concentration of 10 µM anordrin (FIG. 7B), suggesting anordrin may act through the ERK pathway to mediate its inhibitory effects on cell growth. Based on our findings we predict a route of action through MIES modulation and propose a useful application for anordrin in a combination therapy protocol to abrogate the side effects induced by traditional estrogen blocking treatments.

Figure 2E:
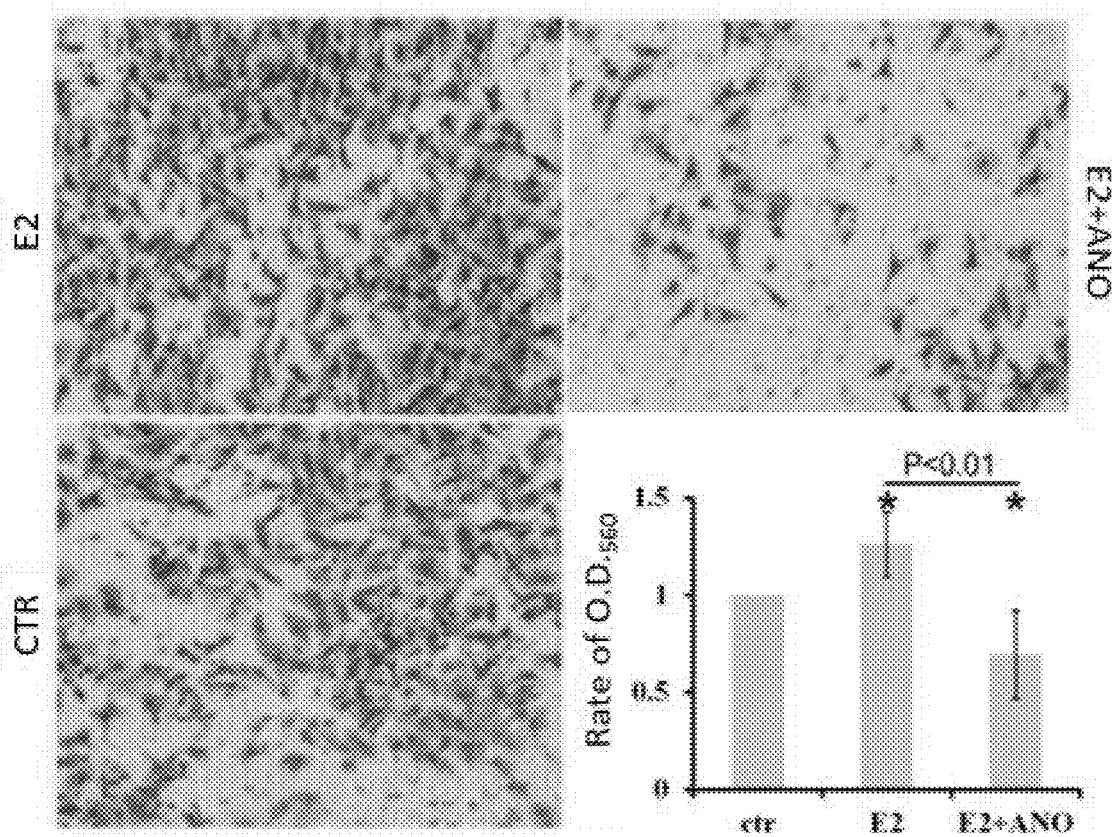
Figure 2F:
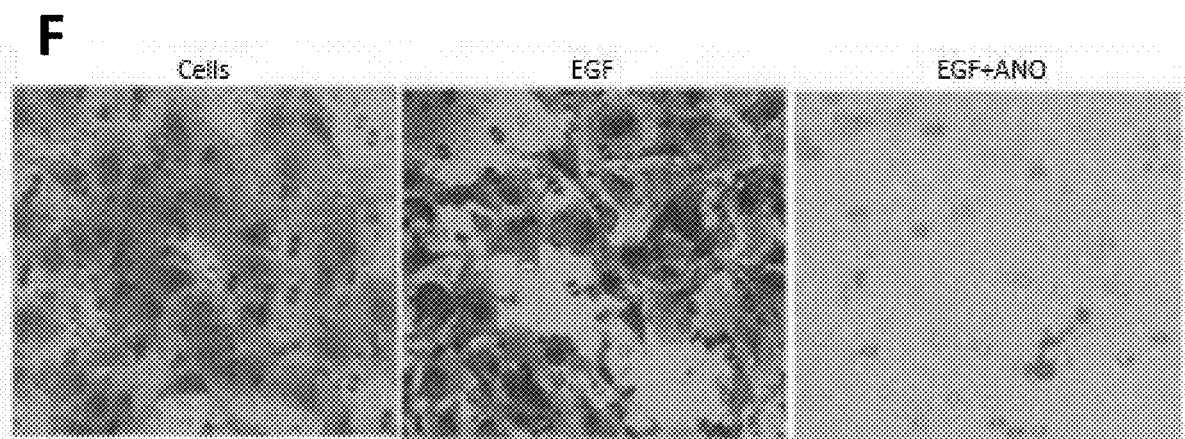
Figure 22A:
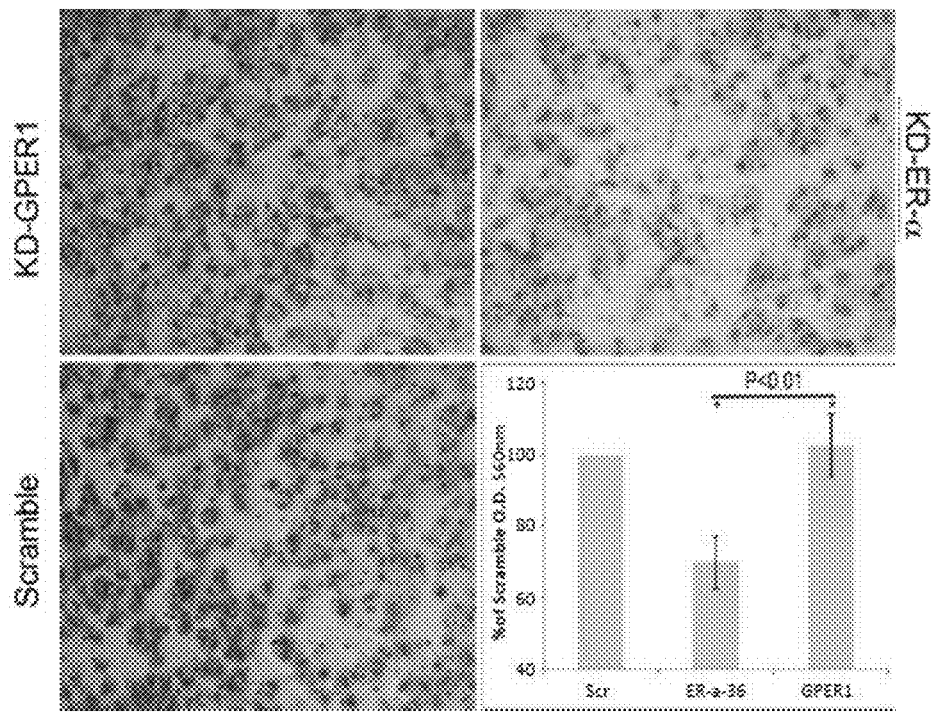
FIGS. 22A-22B.
Figure 22B:
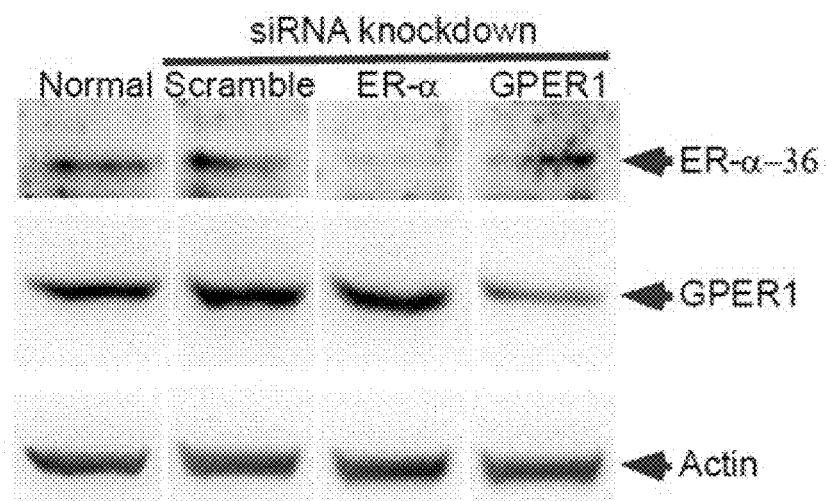

E2-ER complexes associated with the plasma membrane can modulate the biological functions of scaffolding proteins, such as Cas-associated substrate (p130Cas), also known as breast cancer antiestrogen resistance 1 (BCAR1) in humans. The integrin-p130Cas complex plays a fundamental role in the regulation of extracellular matrix (ECM) and cancer cell migration and invasion. ER-α-36 has previously been shown to modulate MDA-MB-231 cell migration (24). As anordrin has been reported as an anti-angiogenic agent resulting in inhibition of cell migration and invasion (16), we studied its ability to modulate MDA-MB-231 cell migration using matrixgel. MDA-MB-231 cells were exposed to either 10 nM E2 or 10 ng/ml EGF in combination with anordrin or vehicle control in basal wells. After 20 hours migrated cells were stained and quantified using a plate reader at 560 nm. We found that both E2 and EGF slightly enhanced MDA-MB-231 cell migration. 6 µM anordrin significantly inhibited the migration of MDA-MB-231 cells in medium containing either E2 or EGF (FIG. 2E and FIG. 2F). Interestingly, anordrin more efficiently inhibited MDA-MB-231 cell migration mediated by EGF than by E2. Furthermore, we knocked down ER-α-36 or GPER1 in MDA-MB-231 cells using specific siRNAs. We found that the migration efficiency of MDA-MB-231 cells decreased in response to ER-α-36 knockdown. In contrast, the cell migration efficiency was not affected when expression of GPER1 was knocked down in MDA-MB231 cells (FIGS. 22A-22B).

Figure 2G:
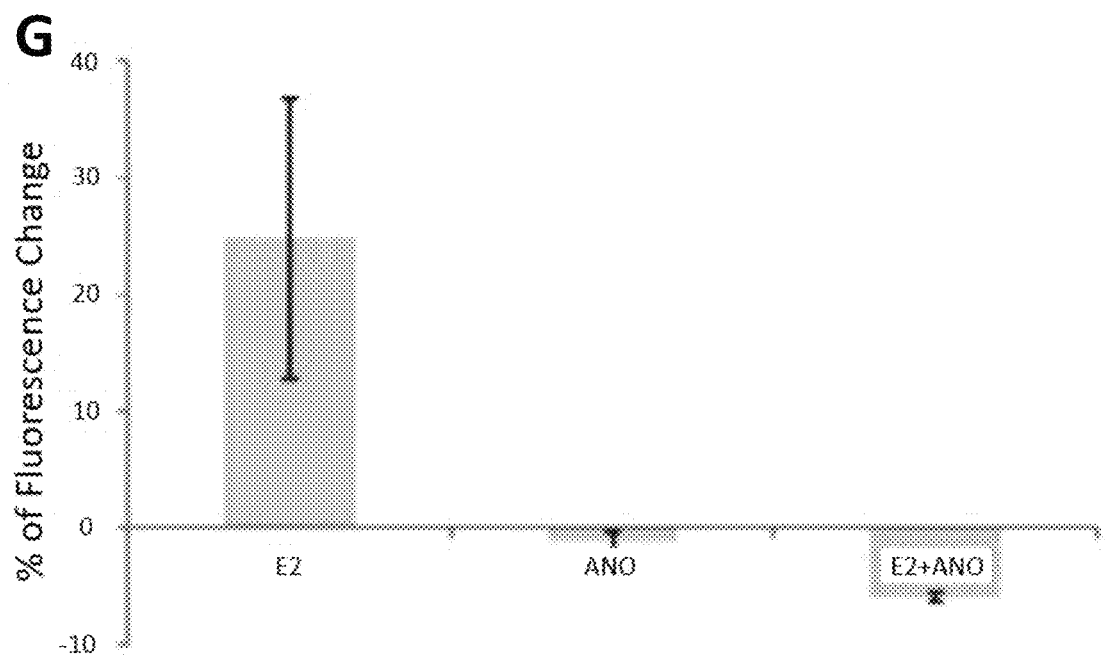
Figure 2H:
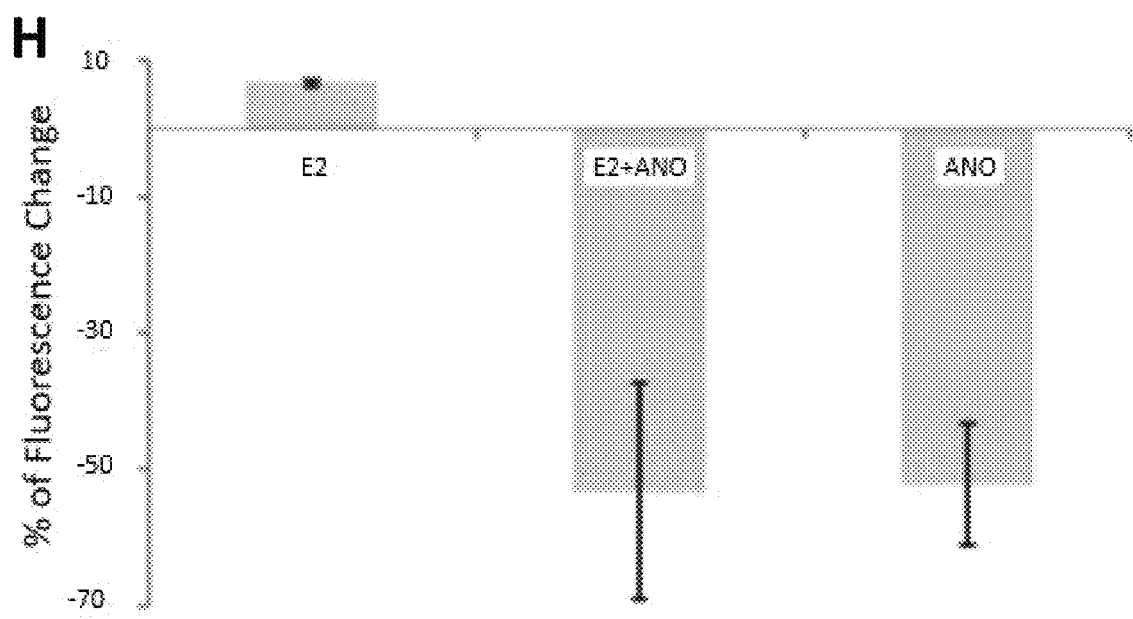
Figure 15:
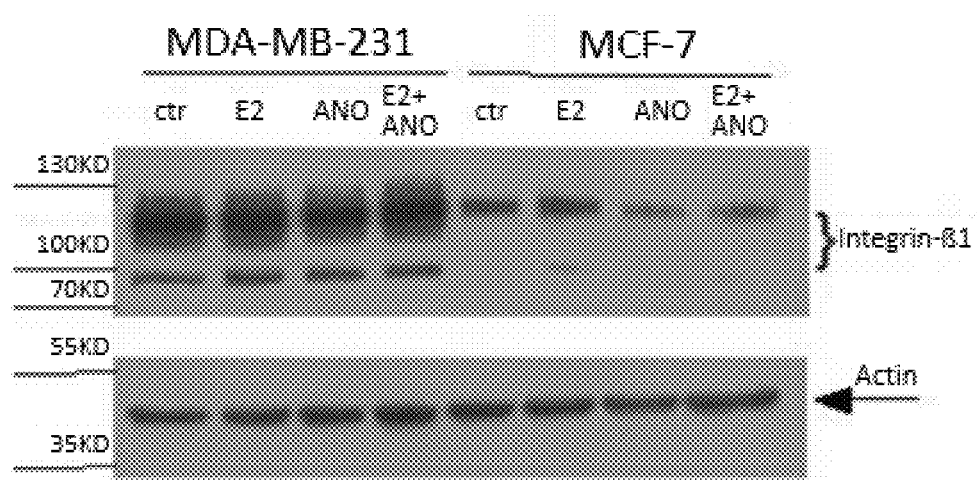
FIG. 15: 6 μM ANO does not change the expression level of integrin β1 in both MCF-7 and MDA-MB-231 cells. MCF-7 cells were harvested and lysed in RIPA buffer. 40 μg total protein of cellular lysate was used for Western blotting to determinate the expression level of integrin β1. Upper gel shows the expression level of integrin β1; Bottom gel shows the amount of actin.

Integrin translocation to the cell surface is regulated by the p130Cas scaffold protein complex to play a fundamental role in cell attachment and migration. Integrin α3β1 has been reported to be involved in MCF-7 cell attachment as well as MDA-MB-231 cell migration (25, 26). Our results suggest a role for anordrin as a possible down-regulator of integrin distribution onto the cell membrane through negative modulation of the E2-ER-p130cas-integrin signaling pathway. To verify the hypothesis, we treated MCF-7 and MDA-MB-231 cells with 6 μM anordrin for 16 hours and measured cell surface integrin β1 distribution using a FITC-labeled anti-integrin β1 antibody. We found that anordrin down-regulated integrin β1 distribution to the plasma membrane of MCF-7 (FIG. 2H) and MDA-MB-231 (FIG. 2G) cells. However, it did not affect the expression level of integrin β1 in either MCF-7 or MDA-MB-231 cells (FIG. 15). Taken together, we conclude that anordrin or analog thereof (such as anordrin) binds to membrane-associated ER to inhibit cell migration and proliferation.

Figure 3A:
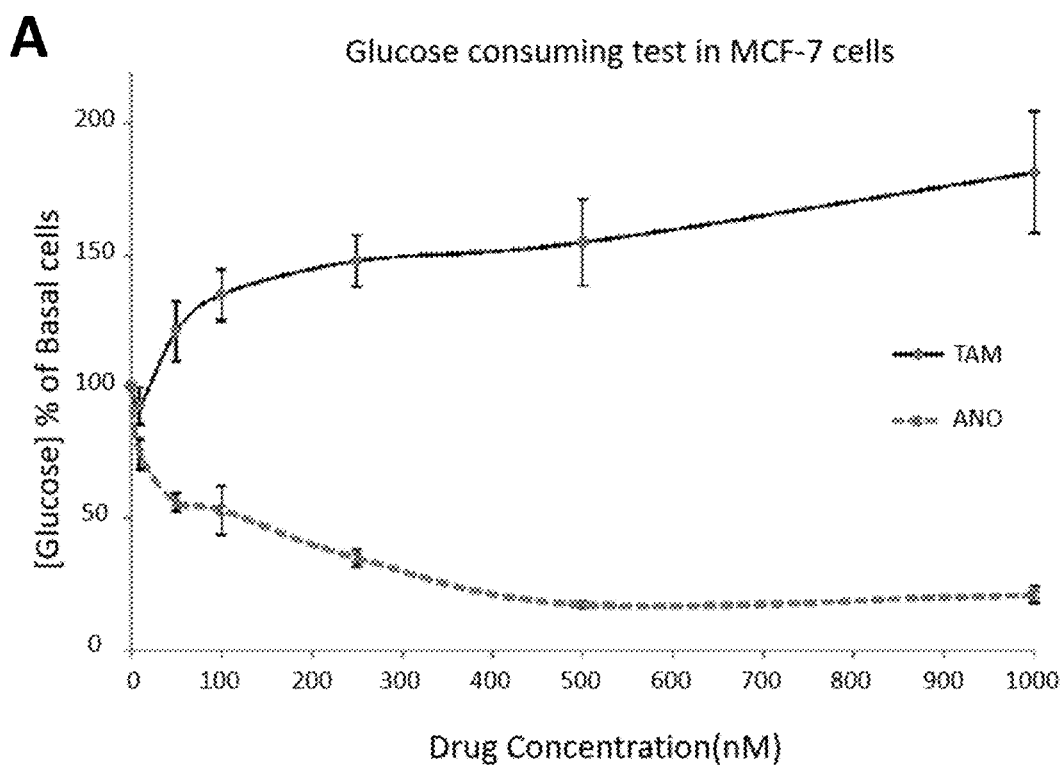
FIGS. 3A-3C: Anordrin or analog thereof (such as anordrin) promotes glucose consumption in MCF-7 cells and decreases blood glucose in mice.
Figure 3B:
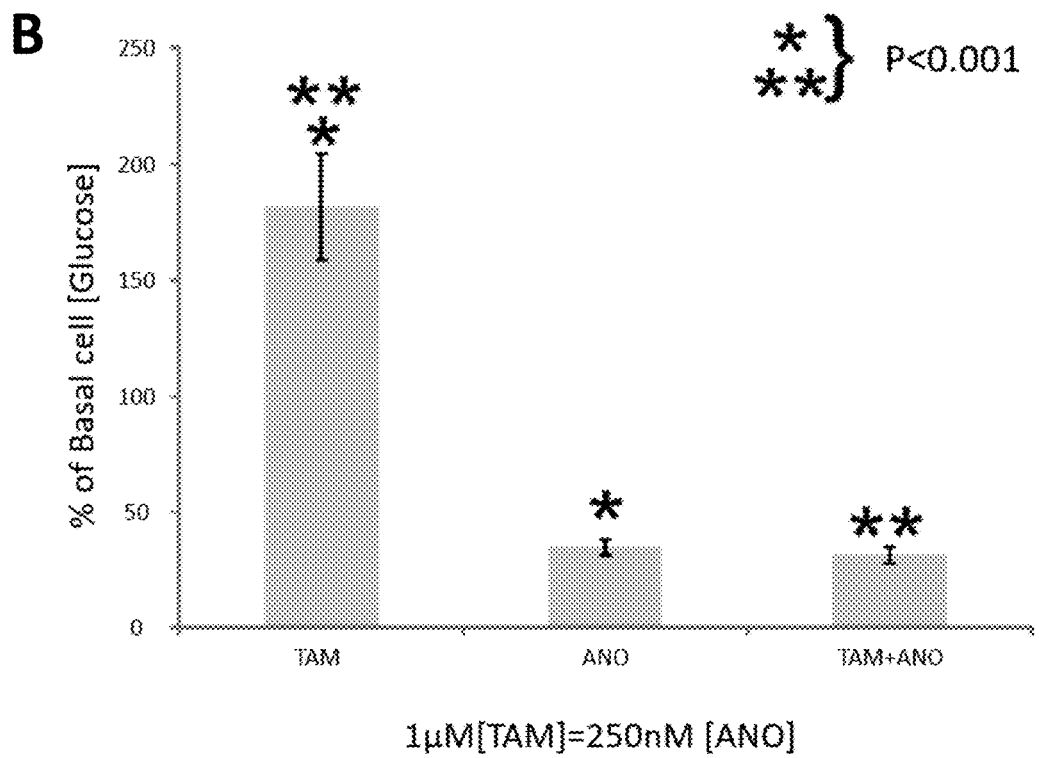
Figure 3C:
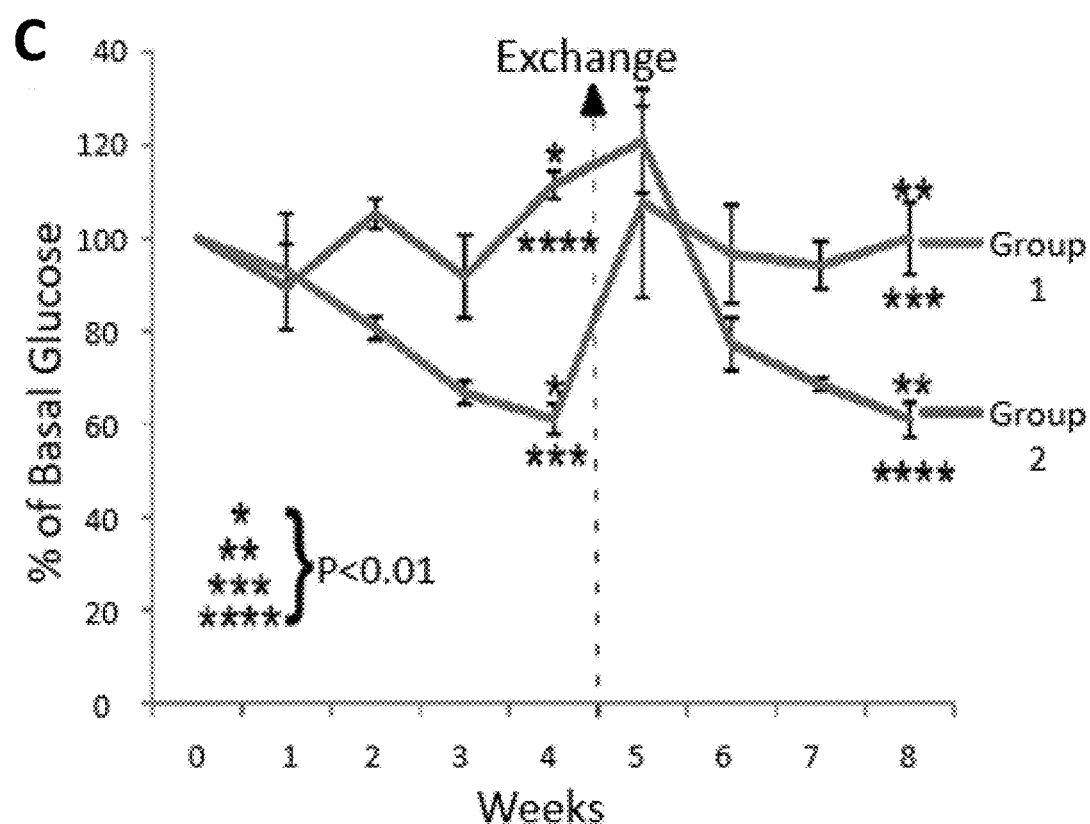
Figure 4A:
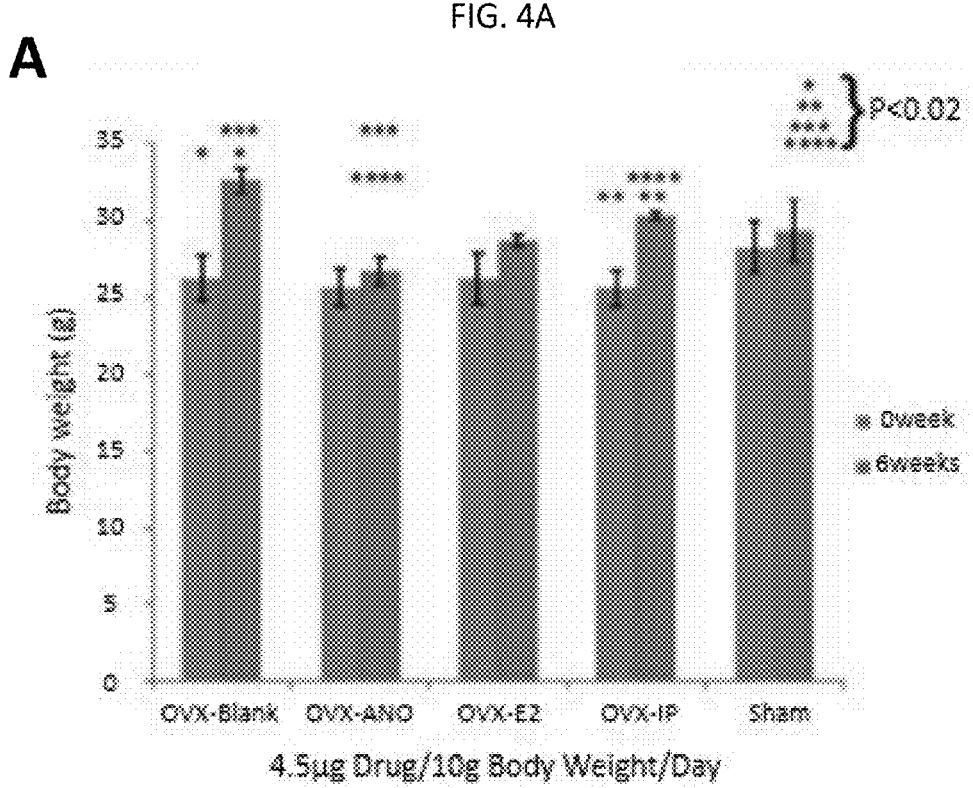
FIGS. 4A-4G: Anordrin or analog thereof (such as anordrin) prevents increased body mass and triglyceride accumulation in liver of ovariectomized (OVX) mice or normal mice treated with tamoxifen.
Figure 4B:
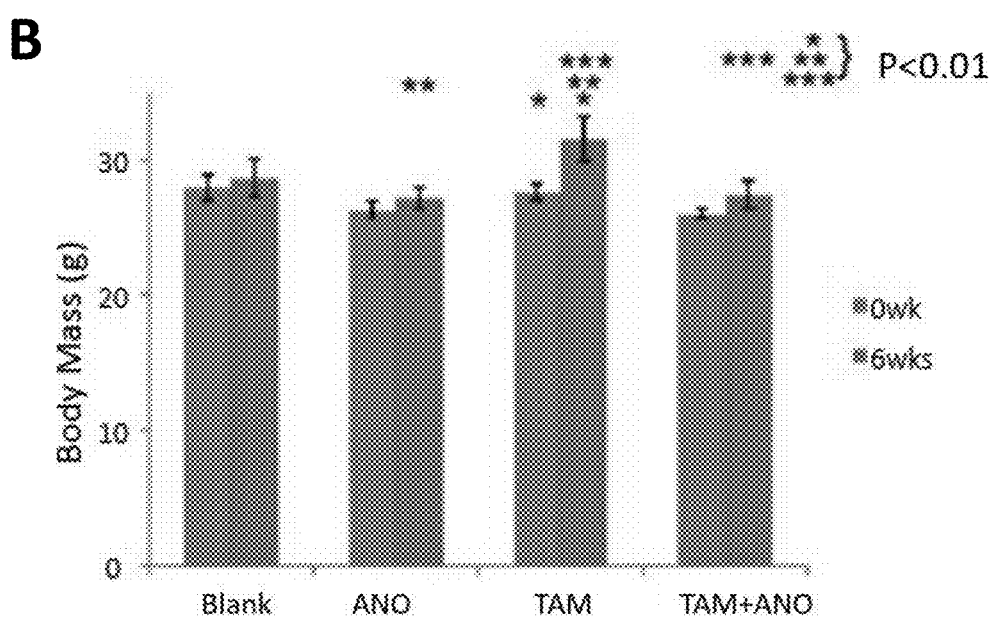
Figure 16A:
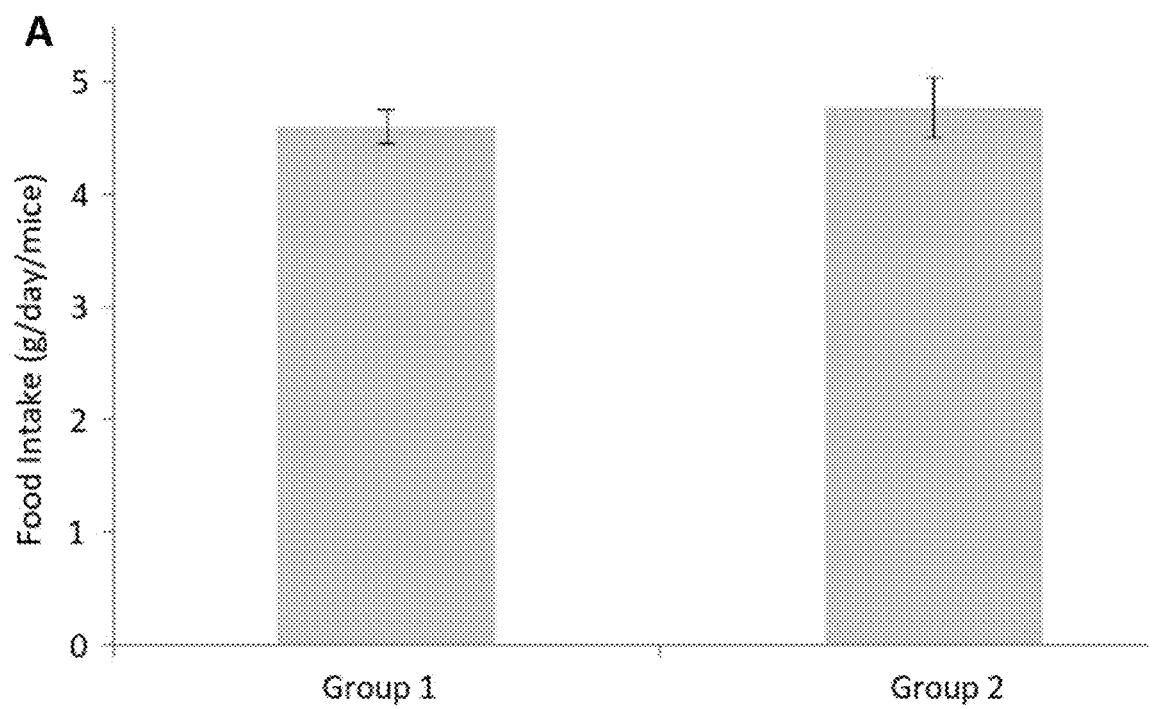
FIGS. 16A-16C: ANO does not change food uptake significantly in all experimental groups under our testing conditions.
Figures 18A, 18B:
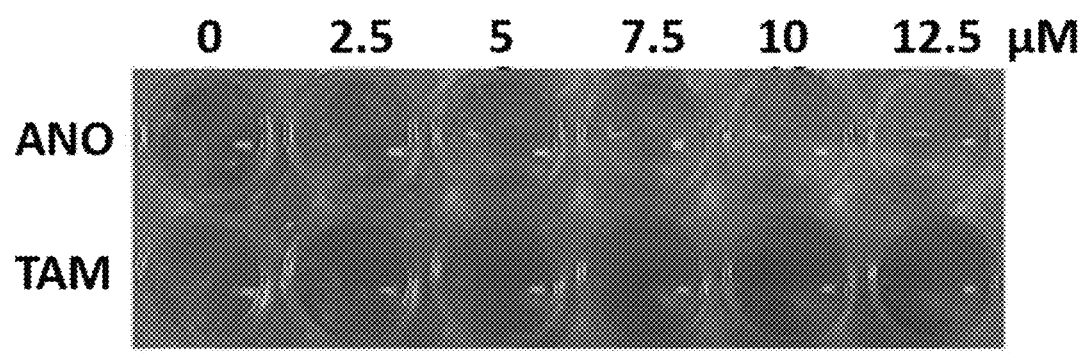
FIGS. 18A-18B: Anordrin or analog thereof (such as anordrin) caused MCF-7 culture medium to have decreased pH, turning yellow. MCF-7 cells were seeded into a 24 well plate at density of 5×10$^5$ cells per well containing drug at indicated concentrations in 0.75 ml medium for 24 hours. The pH of medium was measured using a pH meter.
Figures 19A, 19B:
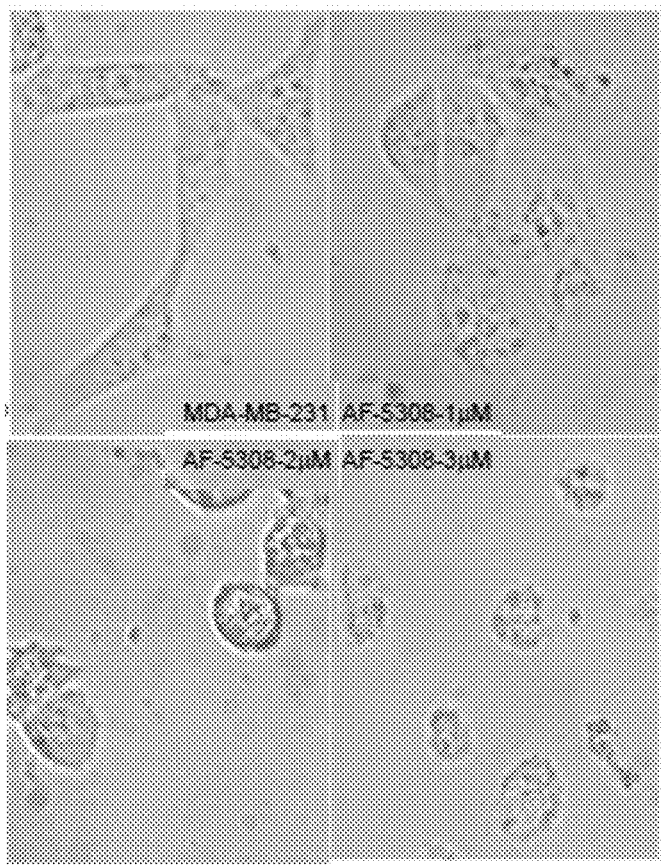
FIGS. 19A-19B: Hydrogene ion of anordrin is a dominant site responsible for inhibiting cell proliferation. Ethyne is substituted by alkyl or alkenyl amine from C2-18 to synthesize derivatives of anordiol. MDA-MB-231 cells are used to measure the drug activity.

Estrogen also plays an important role in the control of energy balance in female mammals. Estrogen modulation of metabolic signaling affects the central nervous system, liver, skeletal muscle, bone, kidney, the cardiovascular systems, etc. The complex of estrogen and its receptor cross-talks with insulin (IL)-insulin receptor (IR) complex or leptin/neuron peptide Y (NPY) and their receptors to regulate food intake, glucose metabolism and adipocyte composition. While studying the effects of anordrin and tamoxifen on MCF-7 cell growth, we observed that the media of cells treated with anordrin was more yellow, indicating decreased pH (FIGS. 18A-18B). One cause for this would be enhanced glucose consumption in anordrin-treated cells compared to those treated with tamoxifen. To determine whether this was the case we treated MCF-7 cells with different concentrations of either anordrin or tamoxifen for 60 hours. The glucose concentration in the culture medium was measured using a glucose assay kit. FIG. 3A shows that the glucose concentration of media from anordrin-treated cells was lower compared to medium from cells treated with tamoxifen. We next tested whether anordrin could increase glucose metabolism in tamoxifen-treated MCF-7 cells. 2×10 MCF-7 cells per well in 100 medium containing 1 μM tamoxifen and 200 nM anordrin were seeded into 96-well plates. Glucose concentration in the medium was measured after 60 hours. FIG. 3B shows that 200 nM anordrin not only reversed the inhibitory effect of 1 μM tamoxifen on glucose metabolism but further enhanced glucose consumption compared to control (FIG. 4B, bar TAM vs bar TAM+ANO). In a mouse model of leptin resistance (db/db), E2 has been shown to increase energy expenditure, leading to reduced body weight (28). We administered anordrin (suspended in 200l sterile water containing 2.5% methyl cellulose) daily at a dose of 0.45μg/g body mass to db/db mice and measured whole blood glucose weekly for 4 weeks using a glucose assay kit. The results show improved glucose consumption in anordrin-treated female mice (group1) compared to controls (group 2) (FIG. 3G). Food intake and body mass did not change significantly during the testing period (FIG. 16A). Interestingly, anordrin had no affect on glucose consumption in male db/db mice (data not shown).

Figure 4C:
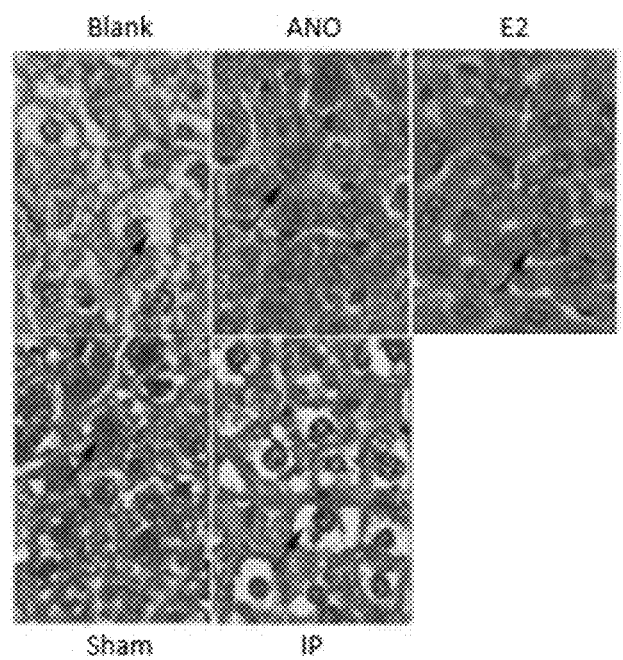
Figure 4D:
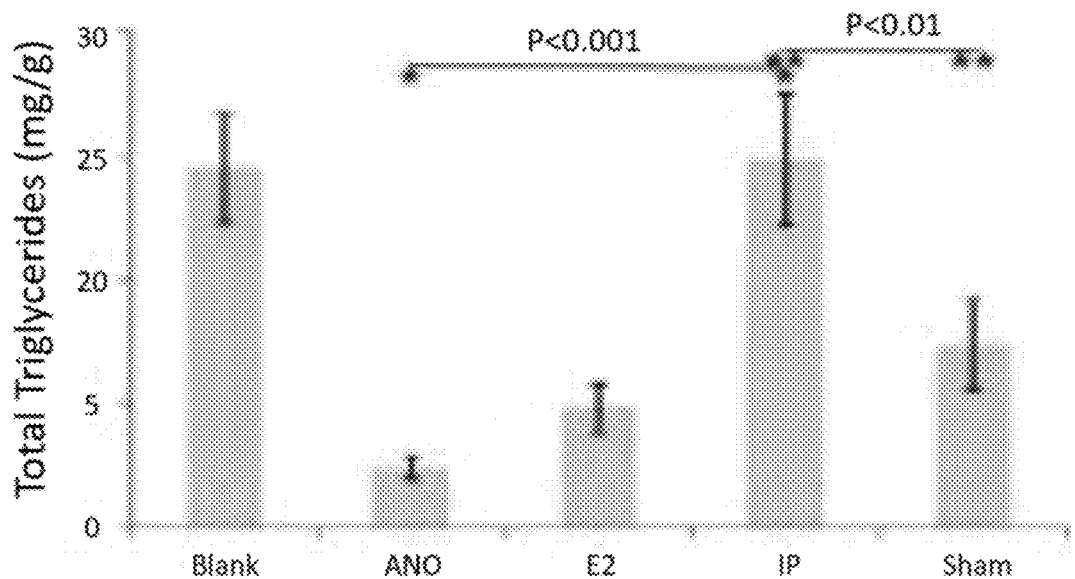
Figure 4E:
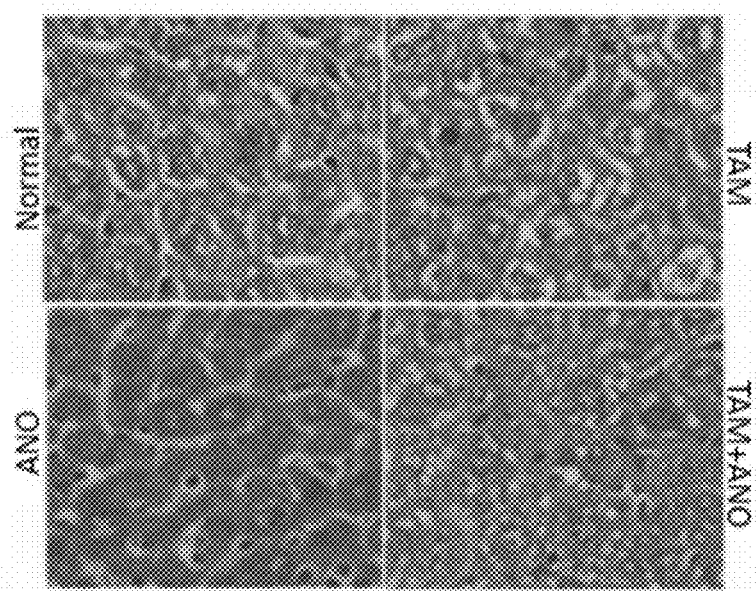
Figure 4F:
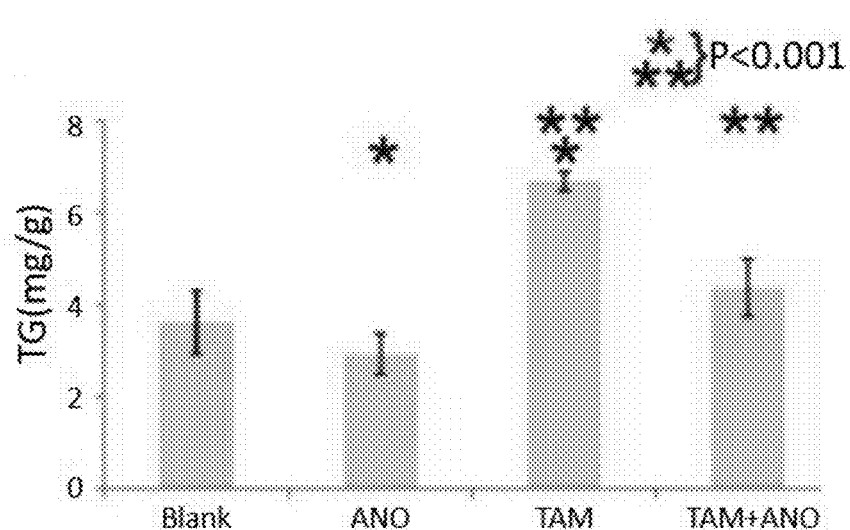
Figure 4G:
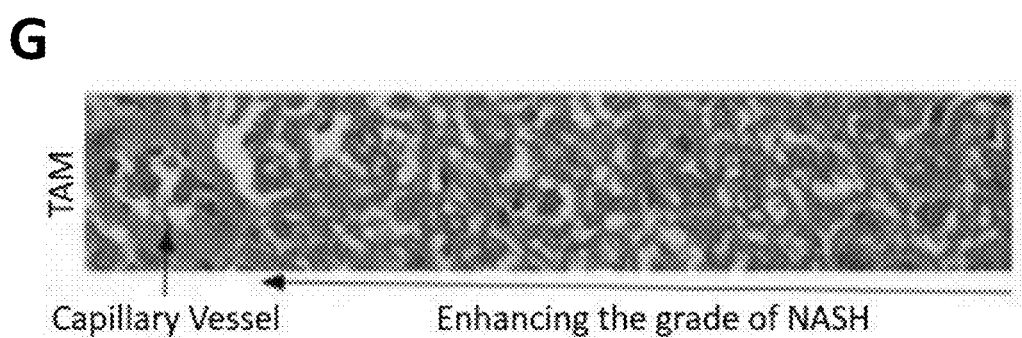
Figure 5A:
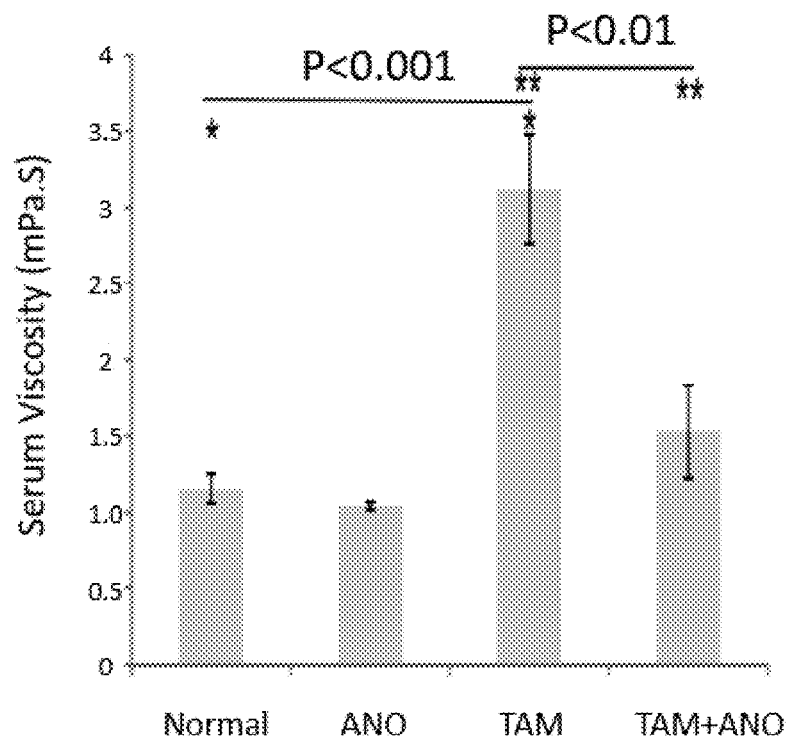
FIGS. 5A-5B: Anordrin or analog thereof (such as anordrin) decreases serum TG and viscosity induced by tamoxifen.
Figure 5B:
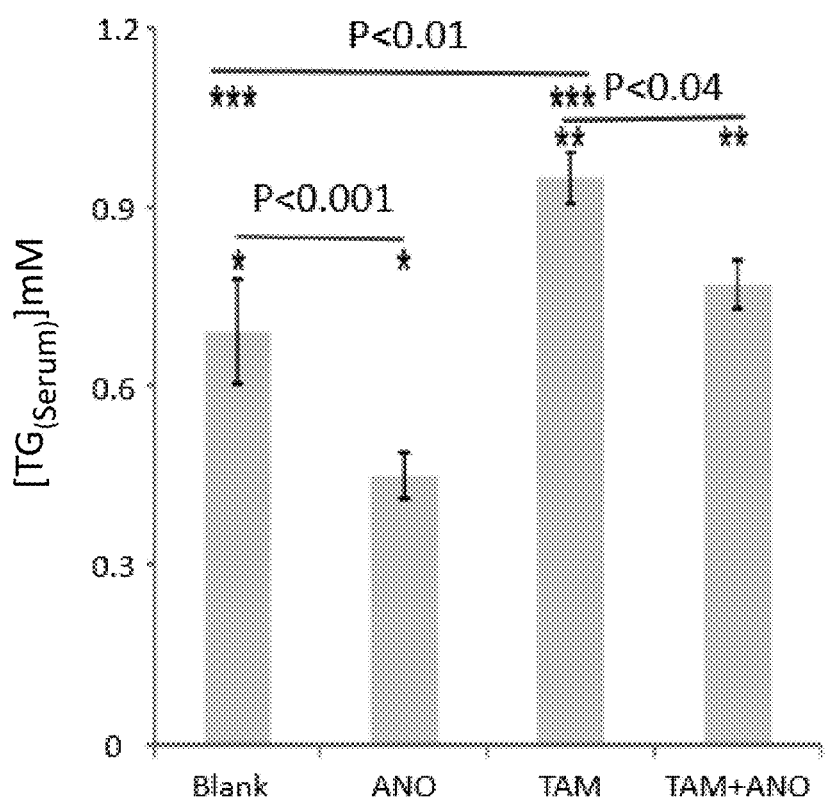
Figure 16B:
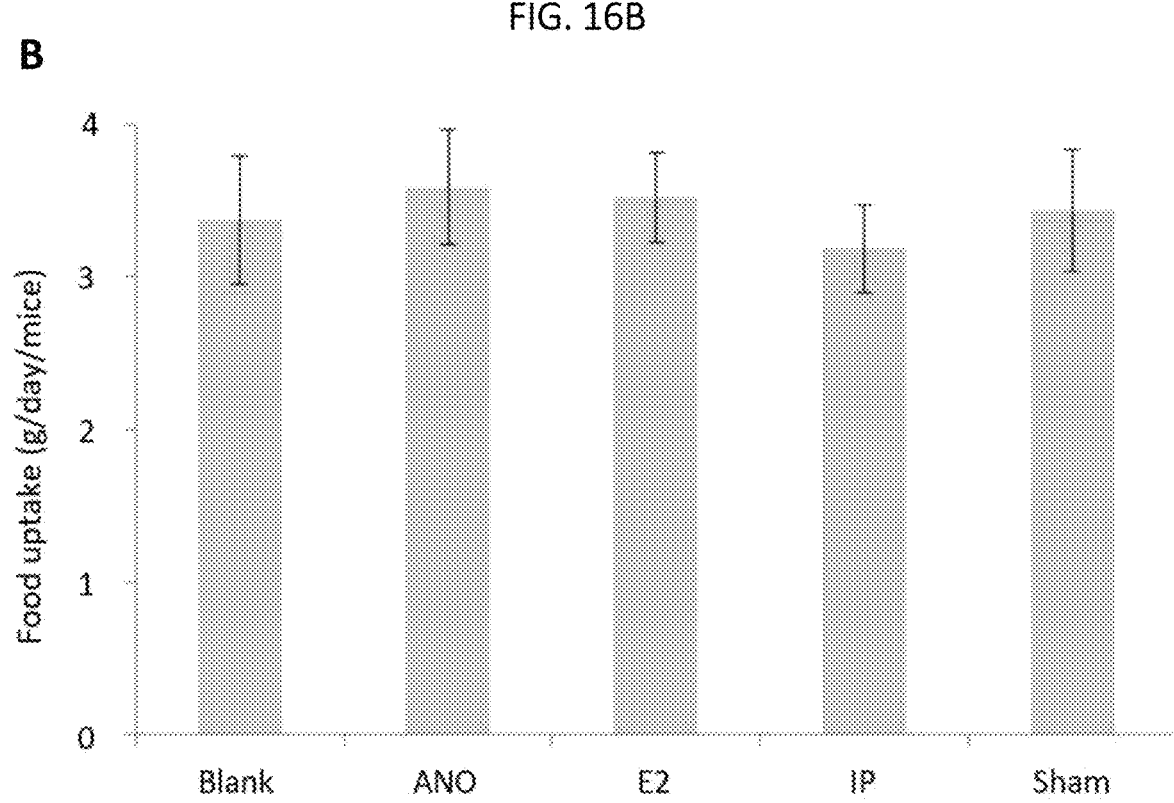
Figure 16C:
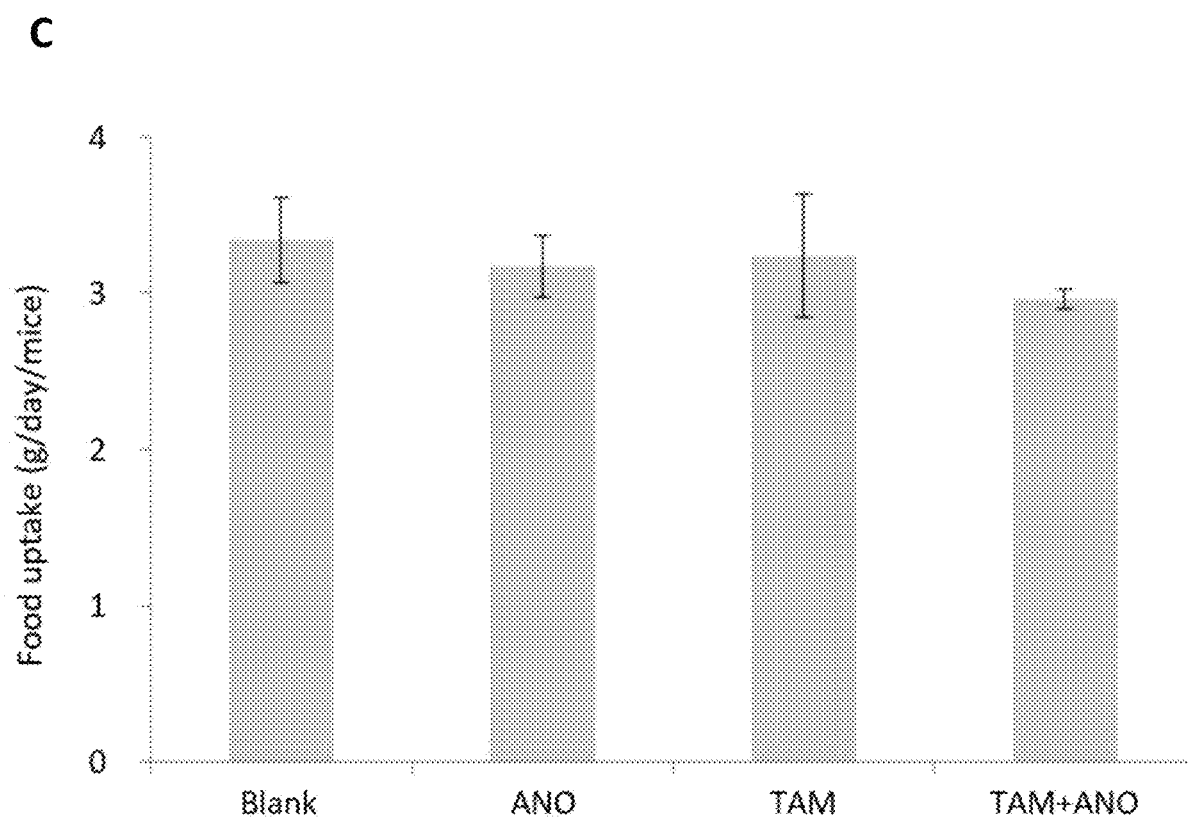
Figure 17A:
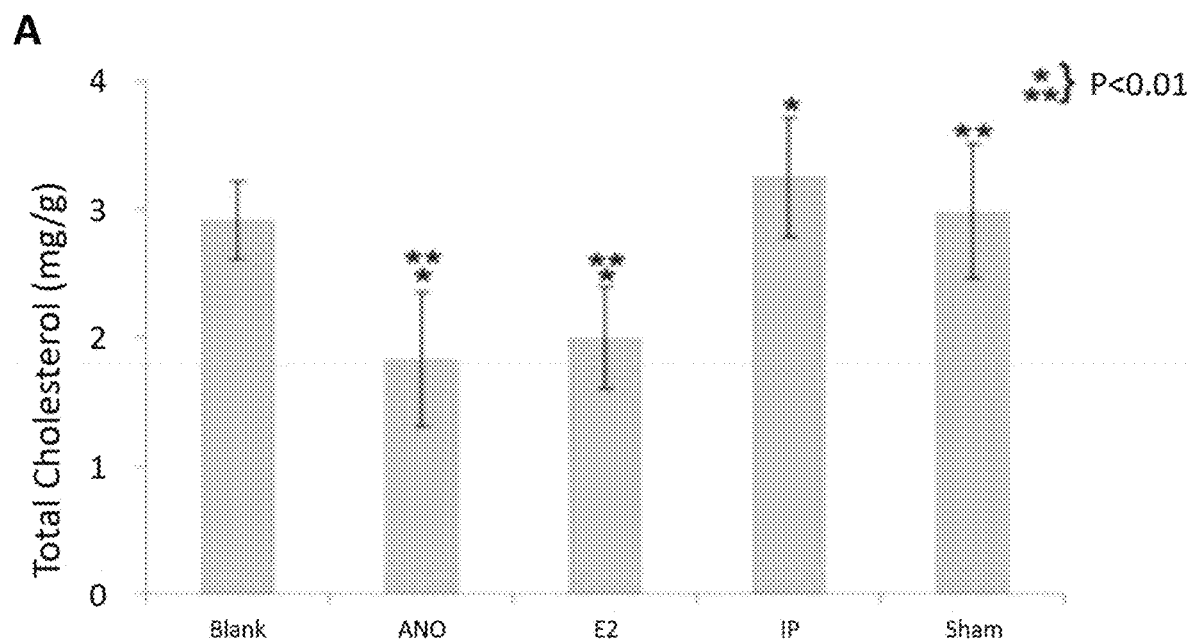
FIGS. 17A-17B: Total cholesterol in liver.
Figure 17B:
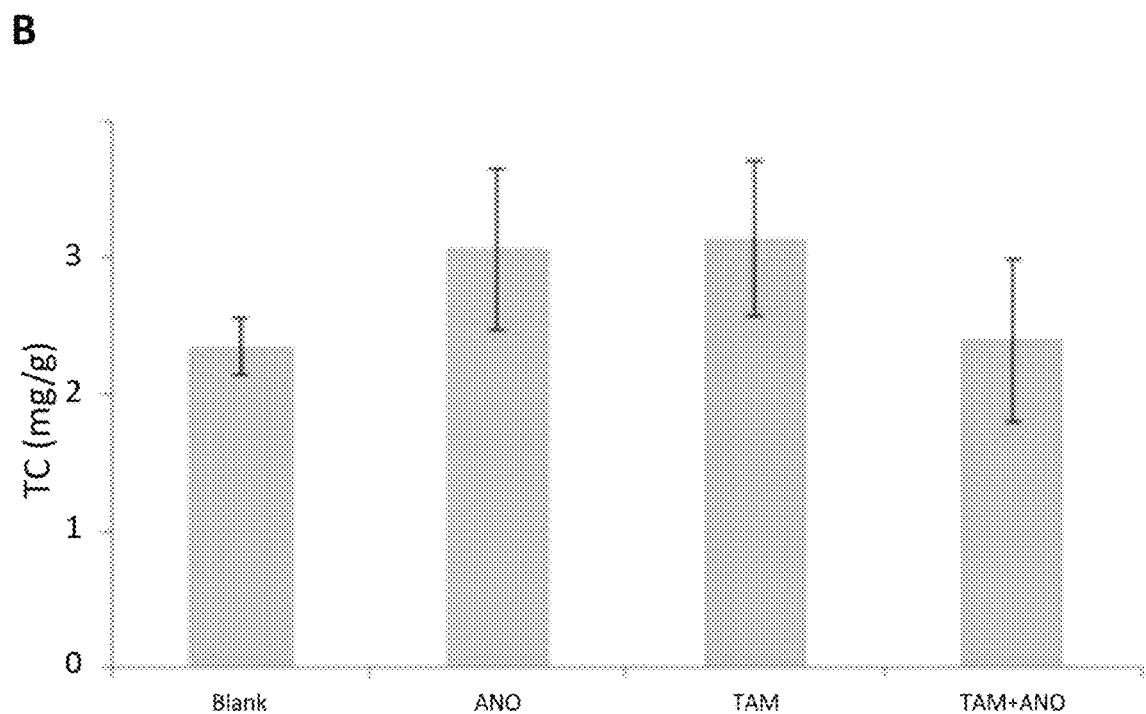
Figure 21:
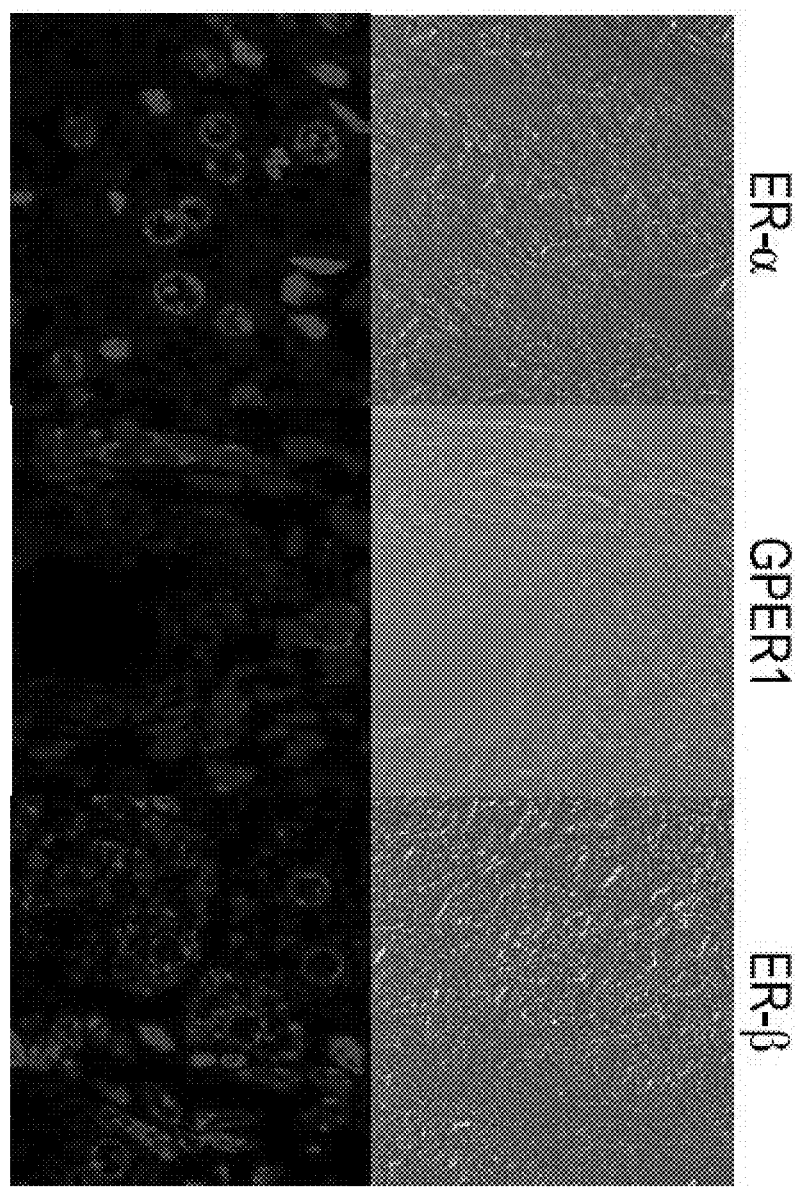
FIG. 21: Immunofluorescence staining (left panels) of paraffin sections of mouse livers using fluorescently labeled (red) antibodies against ER-α (top), GPER1 (middle) and ER-b (bottom). Nuclei were stained using DAPI (blue). Images in the right panels are corresponding bright-field images. Only GPER1 showed perinuclear localization.

Estrogen is one of the key adipokines involved in the regulation of glucose metabolism, modulating the balance between ATP synthesis and deposition of fat in adipose tissue. Decreasing estrogen levels can lead to increased fat storage and obesity in postmenopausal women, increasing the incidence of diabetes II and non-alcohol steatohepatitis (NASH). Consequently, anti-estrogen therapies, such as tamoxifen, enhance the incidence of NASH in breast cancer patients. Our results have already shown that anordrin enhances glucose metabolism in MCF-7 cells and db/db mice, and we predicted that it could prevent increased liver fat in ovariectomized (OVX) mice as well as NASH induced by tamoxifen in normal mice. To test this hypothesis, the ovaries of 6 week old mice were surgically excised. 3 days post surgery, the mice were given intragastric injection of ipriflavone, E2, anordrin or vehicle control. Body mass and food intake were measured weekly. We found that after 6 weeks body mass increased in ipriflavone and control groups, but remained unchanged in sham, E2 and anordrin groups (FIG. 4A). Food intake was not affected in any of the groups (FIG. 16B), indicating the differences were due to changes in energy expenditure. Mice were then sacrificed to harvest 30-50 mg of liver, and total lipid was extracted using a 1 ml mixture of chloroform:methanol (2:1) and 0.5 ml physiological salt solution. Total cholesterol (TC) and triglyceride (TG) levels in the organic phase were measured using TC and TG assay kits (29). The results show decreased amounts of TC and TG in the livers of ovariectomized (OVX) mice for the anordrin and E2 groups compared to controls, but no change for the ipriflavone group (FIG. 4D, FIG. 17A). The paraffin sections of livers from the anordrin and E2 groups exhibited smaller fat deposits compared to those from the control and ipriflavone groups (FIG. 4C). To further study the effects of anordrin and tamoxifen on glucose metabolism, normal 6-week old mice were treated with either drug alone or in combination. Mice fed with tamoxifen at a dose of 4.5 μg/g body mass per day for 9 weeks showed an increase in body mass (FIG. 4B) and had increased indicators of NASH syndrome (such as TG deposition in the perinucleus) and liver TG levels compared to control mice (FIGS. 4E-4F). Body weight, NASH syndrome and liver TG phenotypes were completely reversed in mice fed with tamoxifen as above in combination with anordrin at a dose of 0.45 μg/g body mass (FIGS. 4B, 4E, and 4F). Liver TC levels were not different between any of the groups (FIG. 17B). We also found that anordrin can reverse the increased serum viscosity and TG levels induced by tamoxifen treatment (FIGS. 5A-5B). Furthermore, immunofluorescence (IF) staining of paraffin sections of mice liver using antibodies against GPER1, ER-α, and ER-β respectively showed that only GPER1 was localized at the perinucleus compared to other estrogen receptors (ER-α, and ER-β, FIG. 21). Taken together, the results suggest that tamoxifen may induce NASH through inhibiting the function of GPER1. In contrast, anordrin or analog thereof (such as anordrin) is an agonist of GPER1.

Figure 23A:
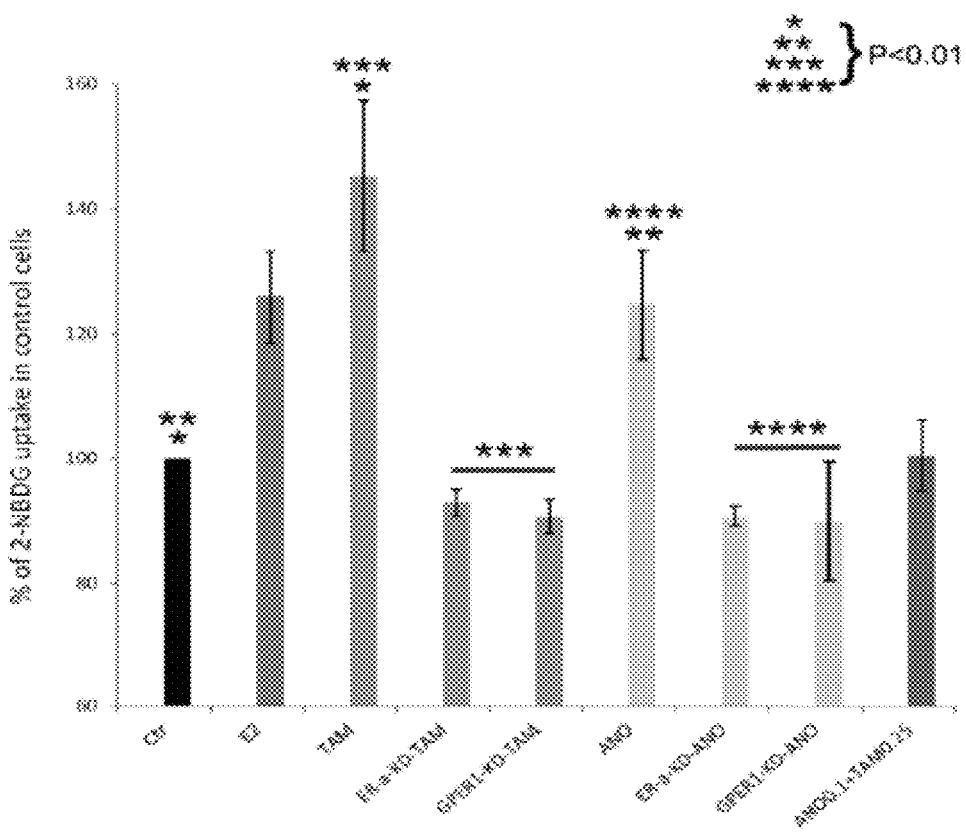
FIGS. 23A-23C: Transient knockdown of ER-α-36 or GPER1 using specific siRNAs decreased the sensitivity of MCF-7 cells to both tamoxifen and anordrin (or anordrin analogs) in terms of effects of the drugs on glucose uptake and cellular ATP levels.
Figure 23B:
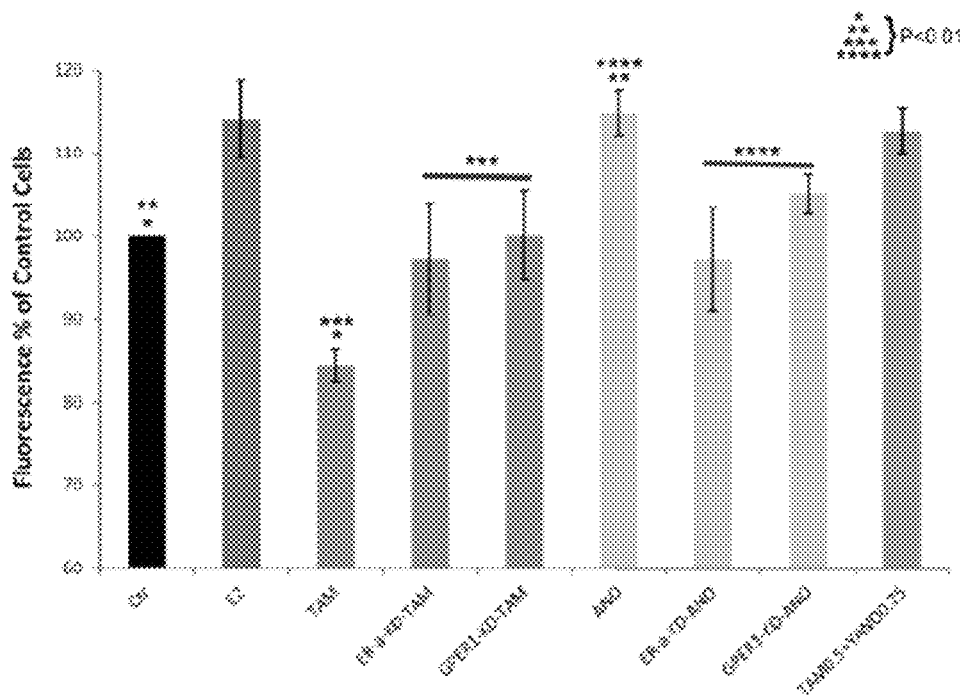
Figure 23C:
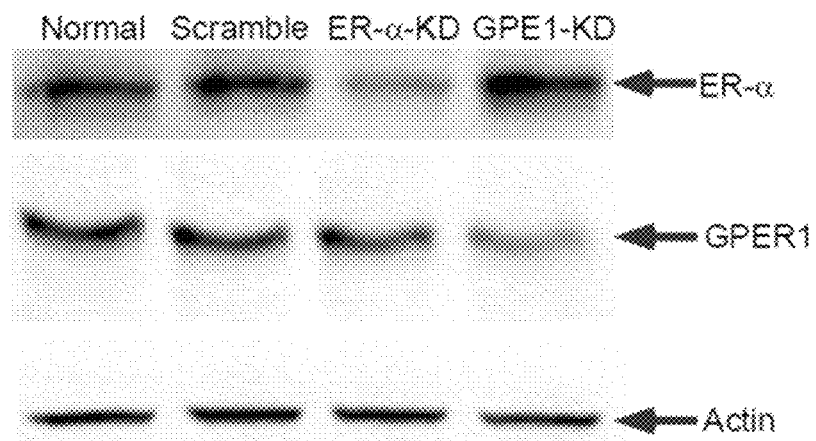

Elevated TG deposition in the perinucleus may be caused by increased glucose uptake or a decreased cellular ATP concentration. Therefore, we tested whether tamoxifen and anordrin or analog thereof (such as anordrin) can regulate glucose uptake and cellular ATP concentrations through ER-α or GPER1. Glucose uptake was measured using fluorescently labeled glucose (2-NBDG), and ATP concentrations were measured using an ATP analysis kit. We found that anordrin enhanced 2-NBDG uptake and cellular ATP concentrations (FIGS. 23A and 23B). Tamoxifen enhanced 2-NBDG uptake, but decreased cellular ATP concentrations (FIGS. 23A-23B). Combination of anordrin and tamoxifen did not change the 2-NBDG uptake level in MCF-7 cells as compared to control with no drug treatment (FIG. 23A). This result indicates that anordrin or analog thereof (such as anordrin) and tamoxifen may regulate glucose uptake through inverse mechanisms. When ER-α or GPER1 was knocked down individually by specific siRNAs in MCF-7 cells (FIG. 23C), we found that the effects of each drug on 2-NBDG uptake and cellular ATP concentrations were reduced (FIGS. 23A-23B). These results suggest that tamoxifen and anordrin or analog thereof (such as anordrin) regulate glucose uptake and cellular ATP concentrations through the crosstalk between ER-α and GPER1.

Figure 8A:
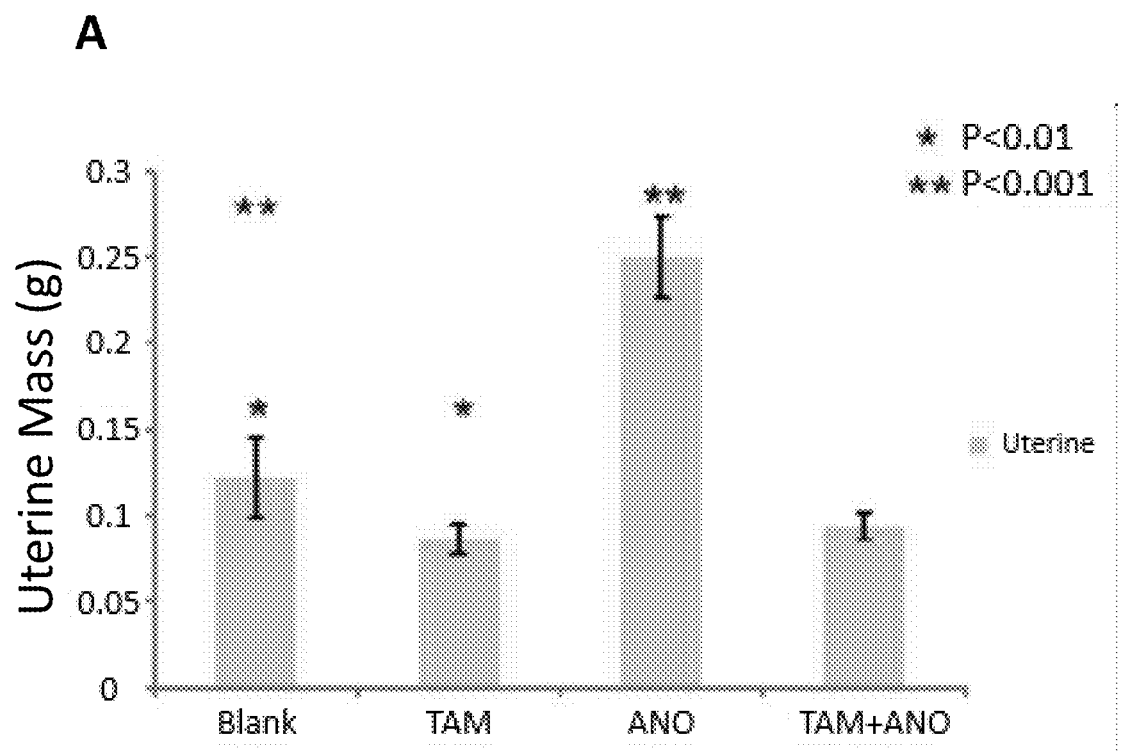
FIGS. 8A-8D: Anordrin or analog thereof (such as anordrin) prevents atrophy of uterine and vagina in ovariectomized or tamoxifen treated mice.
Figure 8B:
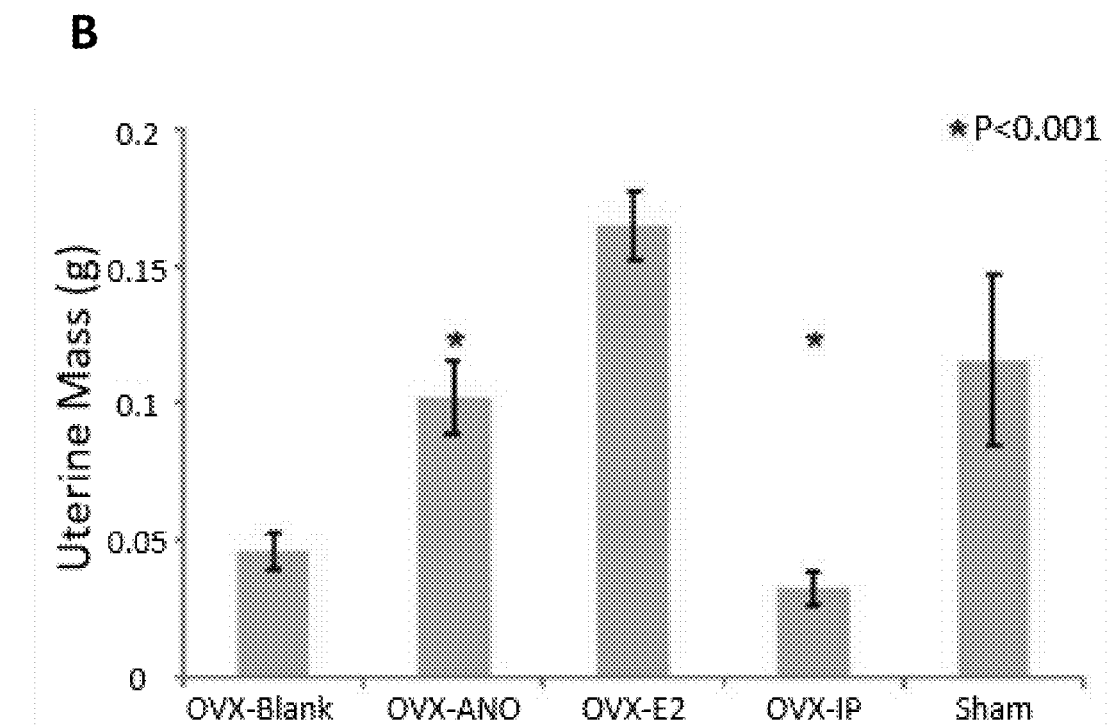
Figure 8C:
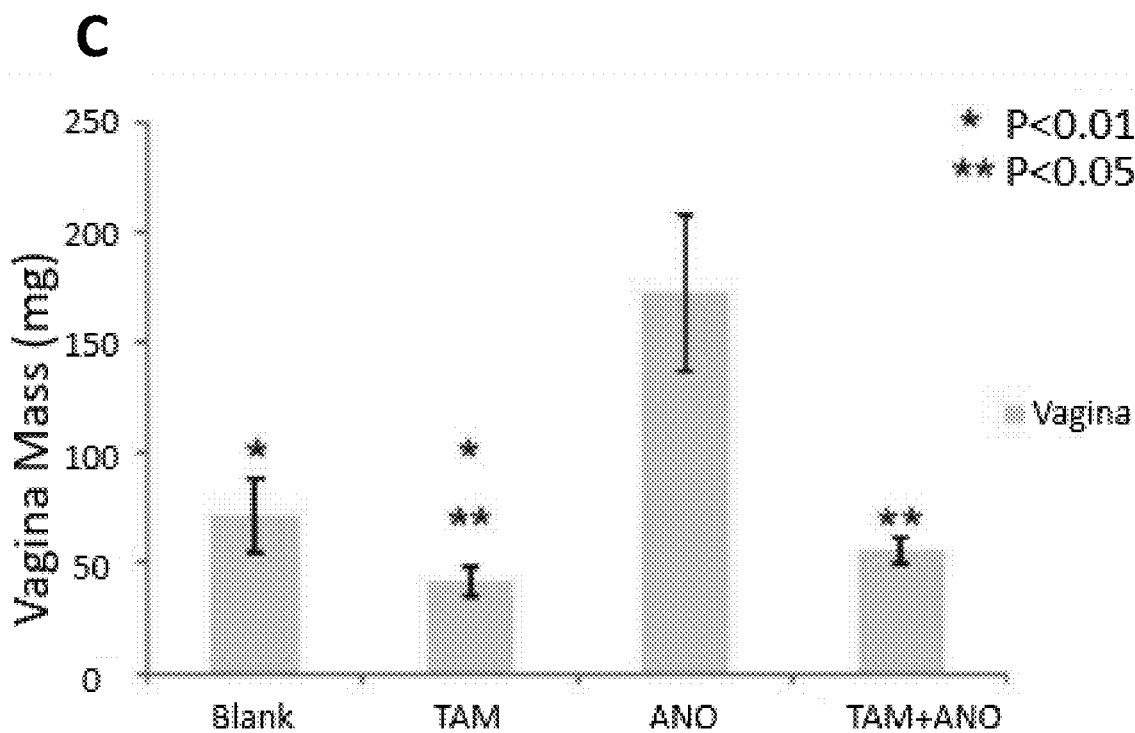
Figure 8D:
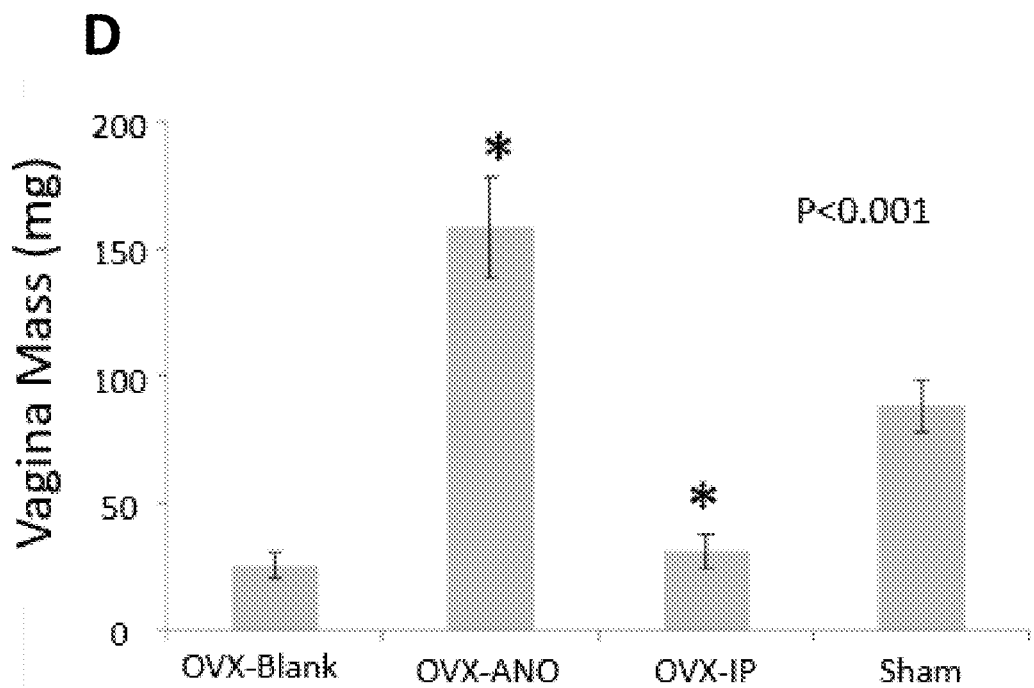
Figure 9A:
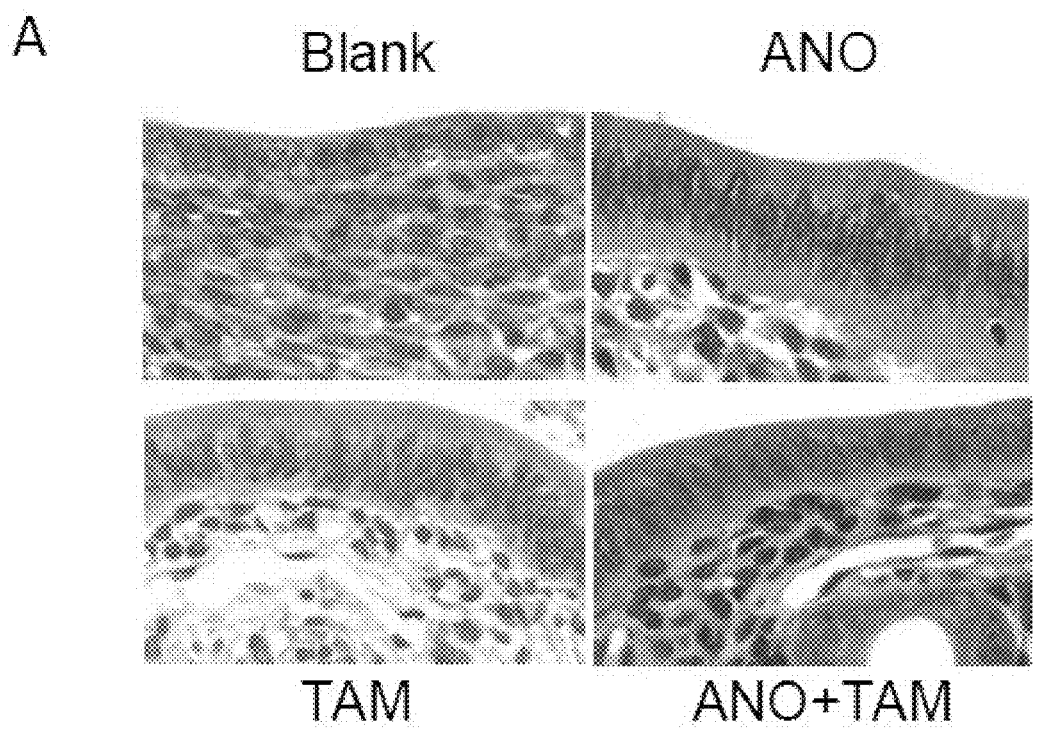
FIGS. 9A-9D: Anordrin or analog thereof (such as anordrin) causes hypertrophy of endometrial epithelial cells (increased cell size while retaining monolayer), but does not induce endometrial epithelial cell proliferation in mice.
Figure 9B:
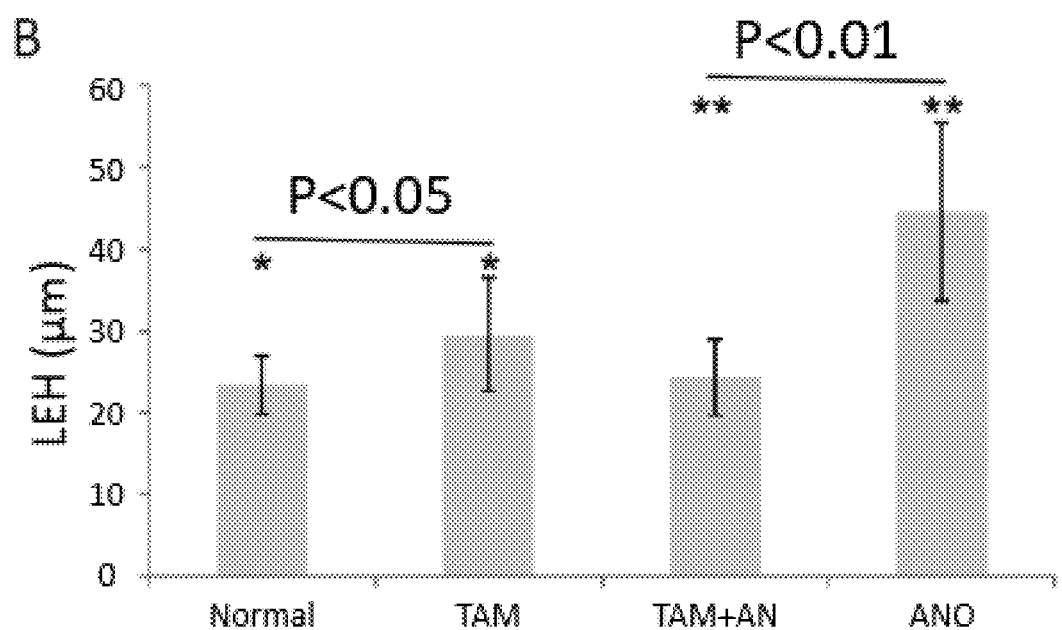
Figure 9C:
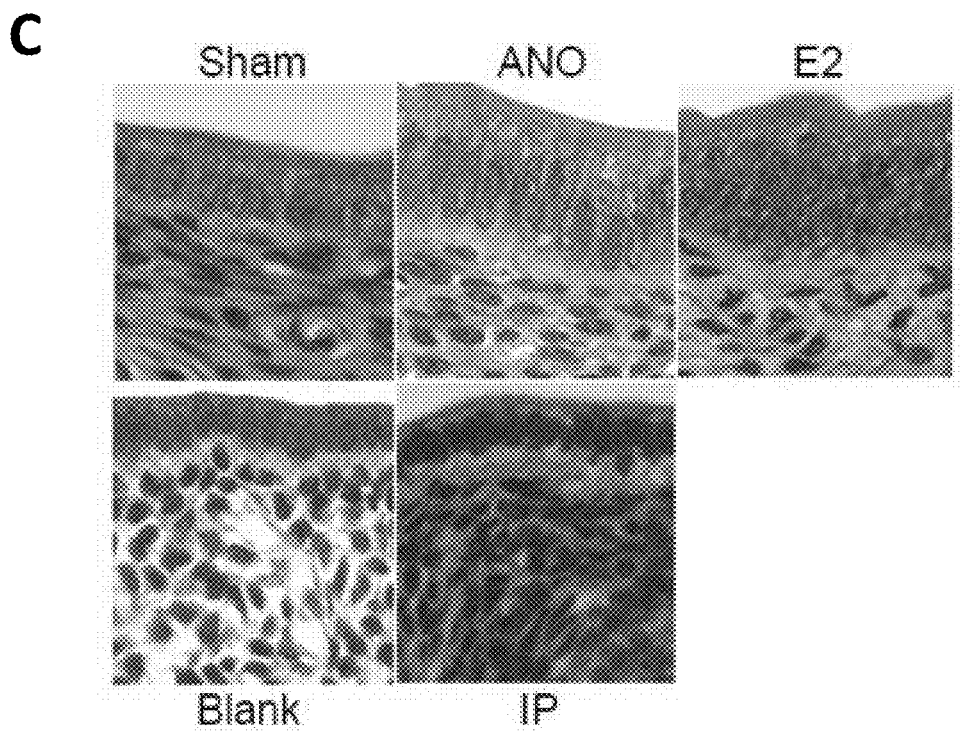
Figure 9D:
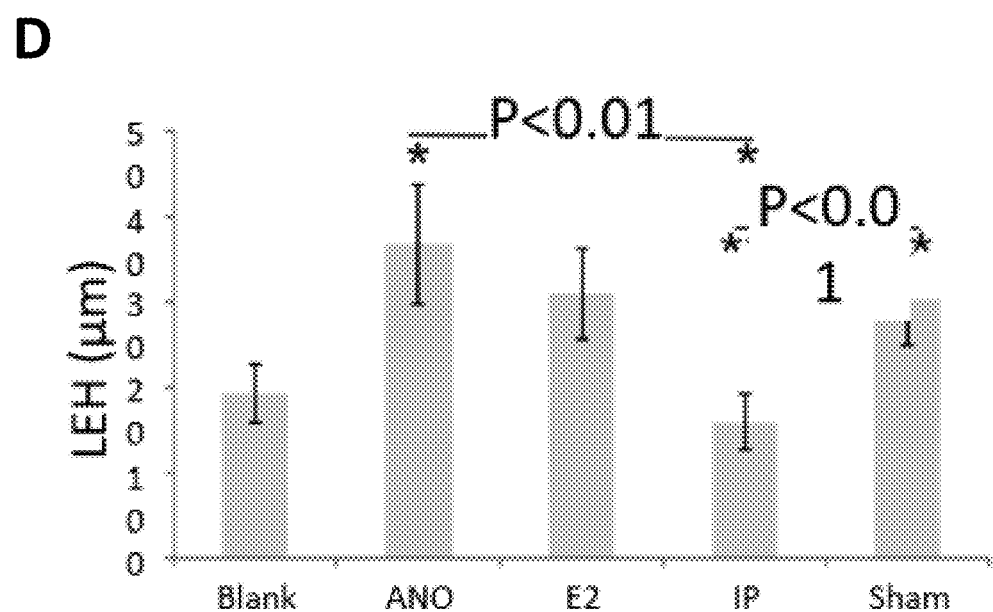
Figure 10:
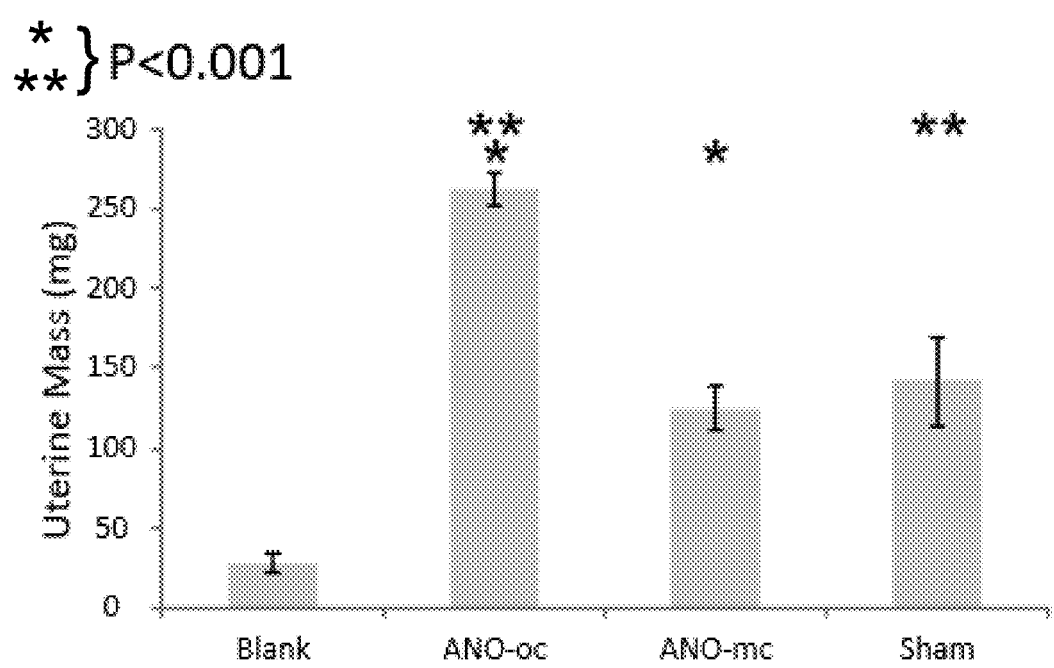
FIG. 10: Corn oil and casein formula (column oc) of anordrin or analog thereof (such as anordrin) enhances its activity to prevent atrophy of mice uterus compared to methyl-cellulose (column mc).

Anordrin or analog thereof (such as anordrin) also has potential therapeutic benefits in the treatment of post-menopausal women. It was found to prevent uterine atrophy in ovariectomized mice (FIG. 8B), and to decrease the extent of tamoxifen-induced uterine and vaginal atrophy (FIGS. 8A and 8C). In particular, a corn oil and casein formulation of anordrin enhanced its activity to prevent uterine atrophy in mice as compared to a formulation using methyl-cellulose (FIG. 10). Importantly, while anordrin causes hypertrophy of endometrial epithelial cells in mice, it does not induce endometrial epithelial cell proliferation, with the epithelium remaining a monolayer, as compared to tamoxifen and E2, which both induce proliferation and development of a polylayer (FIGS. 9A and 9C). Combination treatment with anordrin and tamoxifen resulted in neither hypertrophy nor increased proliferation (FIG. 9A).

Figure 11A:
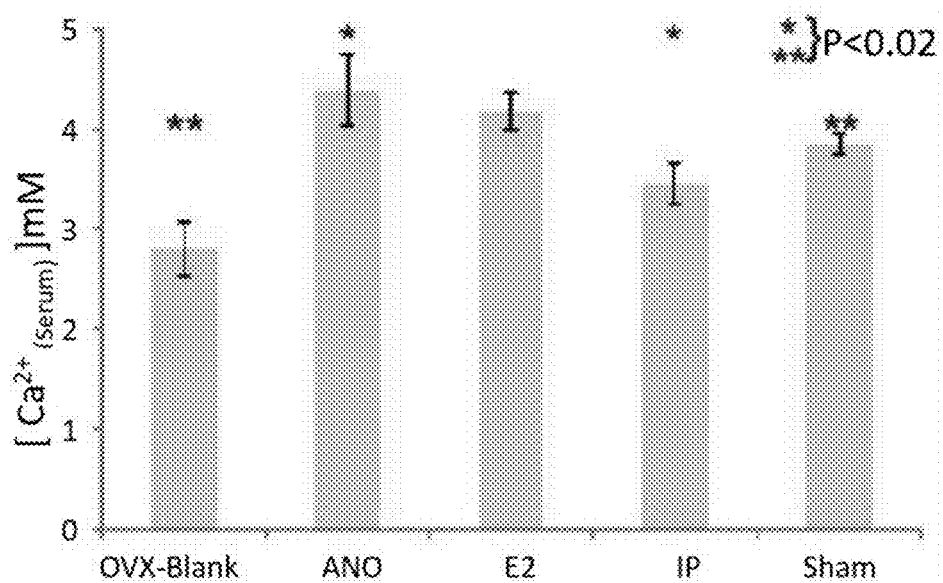
FIGS. 11A-11E: Anordrin or analog thereof (such as anordrin) prevents osteoporosis in ovariectomized mice.
Figure 11B:
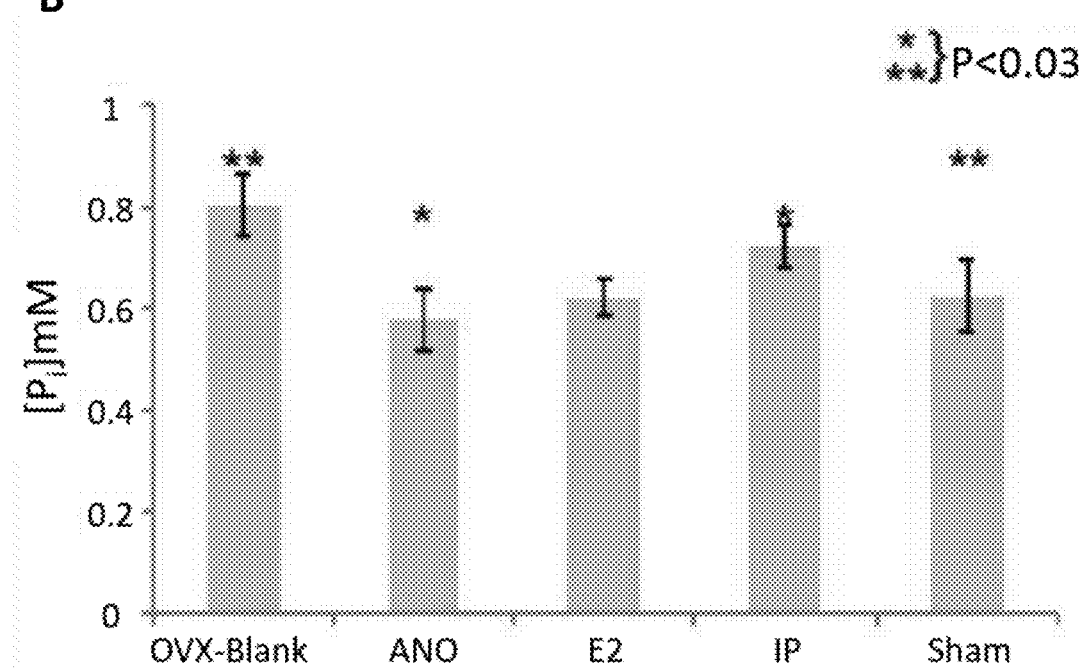
Figure 11C:
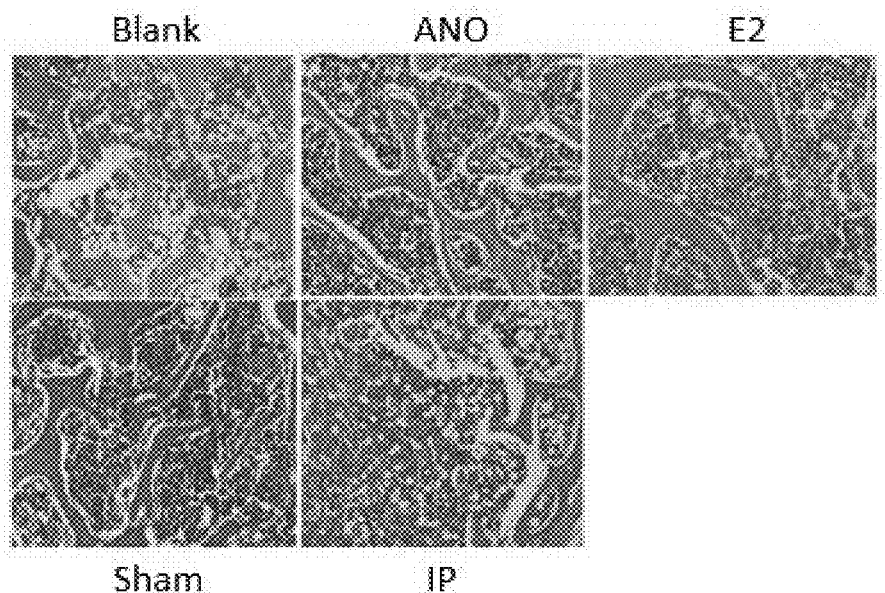
Figure 11D:
Figure 11E:
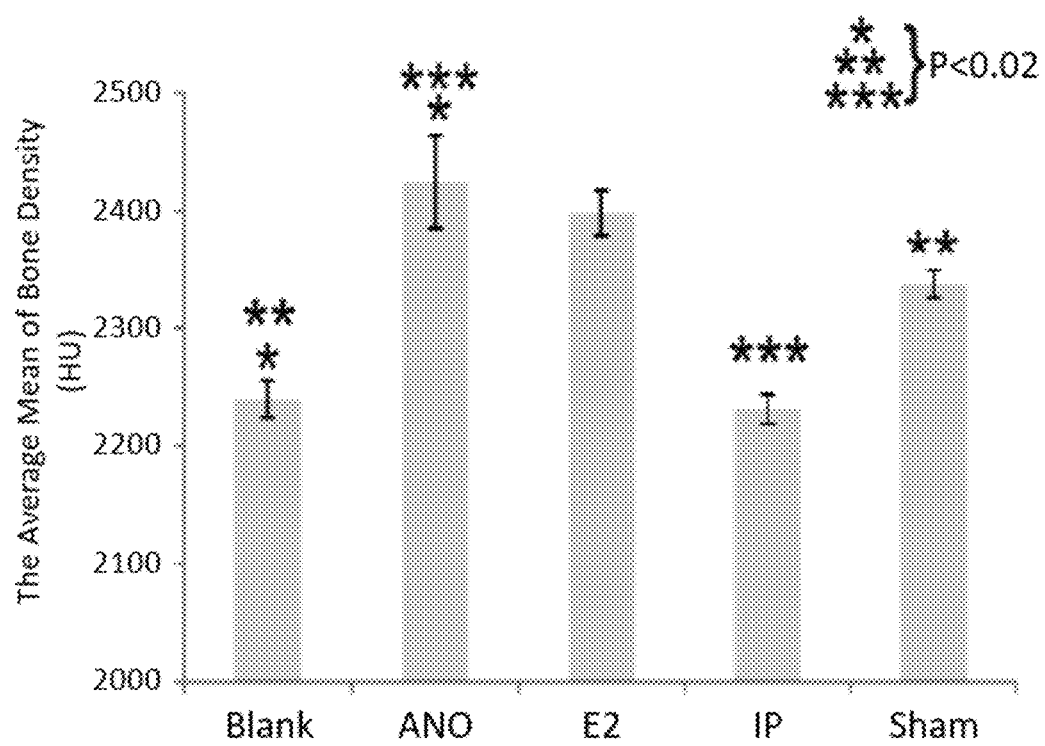

Osteoporosis is a progressive bone disease common in post-menopausal women, characterized by decreased bone mass and density. Decreased serum $Ca^{2+}$ concentration ($[Ca^{2+}]$) and increased phosphate concentration ($[P_i]$) are clinical diagnostic markers used to indicate progression of osteoporosis. Anordrin was found to prevent osteoporosis in ovariectomized mice as indicated by increased serum $Ca^{2+}$ (FIG. 11A), decreased $P_i$ (FIG. 11B), and increased bone density (FIGS. 11D-11E). It was also found to prevent decrease in bone marrow cells (FIG. 11C).

Estrogen, tamoxifen and raloxifene all bind to the LBD of ERs to modulate the estrogen classical pathway. Estrogen replacement therapy or treatment with tamoxifen or raloxifene can enhance expression of ApoD, a component of HDL (FIG. 13B, column3), potentially leading to blood clot formation. We hypothesize that a SERM that does not modulate the classical pathway of estrogen would not cause blood clots or thromboembolism. After a large scale screen, anordrin was identified as a compound that does not modulate the ER classical pathway, and also decreases serum viscosity induced by tamoxifen. We found that the methyl group in $R^6$ of anordrin is essential in decreasing anordrin binding affinity to ER-LBD compared with dinordrin (FIG. 1A, dinordrin vs anordrin). Therefore, an alkyl or alkenyl group in R6 of anordrin is necessary for prevention of blood clots and thromboembolism.

Tamoxifen is a useful therapeutic as an antagonist of the ER classical pathway, but is also an agonist of mERs, inducing the proliferation of endometrial epithelial cells. Anordrin can neutralize tamoxifen-induced proliferation of endometrial epithelial cells, and as such is useful in combination therapy. Based on our findings, we conclude that anordrin is an antagonist of mER. Anordrin does not modulate the ER classical pathway, but it can enhance estrogen metabolic signaling. We propose that anordrin is an agonist of GPER1, through which it modulates estrogen metabolic signaling. In contrast, tamoxifen is an antagonist of GPER1 and inhibits estrogen metabolic signaling.

DISCUSSION

Figure 12:
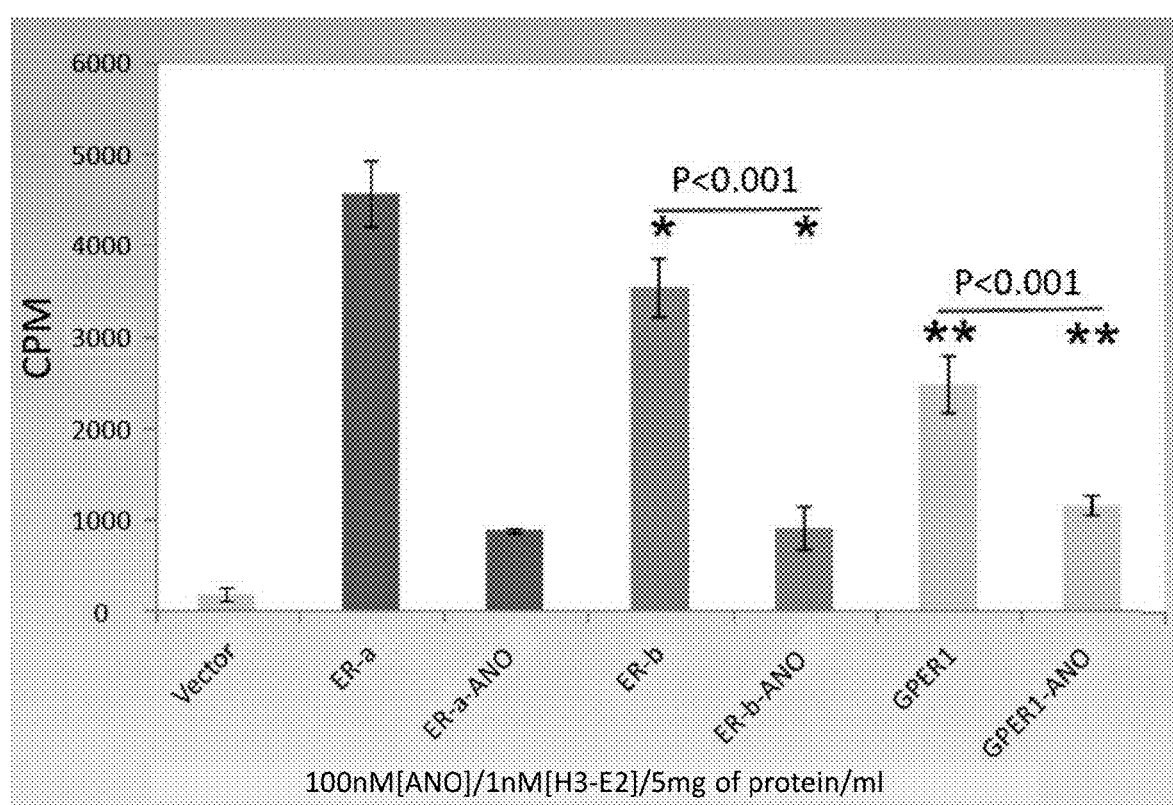
FIG. 12: Anordrin or analog thereof (such as anordrin) inhibits $^3$H-E2 binding to ER-β and GPER1 fusion proteins expressed in HEK-293 cells.

Estrogen binding to its membrane-associated receptors can lead to cytosolic $Ca^{2+}$ oscillations, conveying signals to the extracellular matrix (ECM) and impacting cell migration. InsP3R is one of the major $Ca^{2+}$ channels involved in the regulation of diverse signal transduction pathways. It has been reported to take part in the estrogen modulation of $Ca^{2+}$ release from endoplasmic reticulum (30), and has also been shown to be involved in functional regulation of actin filaments (31). However, the detailed molecular mechanisms underlying this action are not clearly understood. The E2-ER complex has been reported to regulate cell migration through c-Src (32). c-Src is a non-receptor tyrosine kinase that plays an important role in the regulation of cell adhesion, invasion, growth and differentiation. The key regulatory mechanisms of c-Src tyrosine kinase involve the control of its phosphorylation states and kinase activity, which can be modulated by $Ca^{2+}$ signaling induced by E2 interaction with ER. The c-Src-FAK (focal adhesion kinase)-p130Cas scaffold reacts with focal adhesion complexes to regulate the actin cytoskeleton, resulting in the modulation of cell motility and adhesion. The p130Cas/BCAR1 complex interacts with integrin to regulate ECM and migration. Anordrin binds to membrane-associated ER and blocks the signal transduction pathway of estrogen-mediated integrin translocation, resulting in the inhibition of cell migration. Conversely, tamoxifen is an agonist of this signal transduction pathway, and BCAR1, as a core component of this scaffold, is thought to be implicated in the development of tamoxifen-resistance during the treatment of breast cancer patients. Moreover, the FAK-CDC42-ARHGAP21 pathway has been reported to regulate the formation of integrin-F-actin scaffold complex, and consequently glioblastomas cell migration (33). We found that the carboxyl terminus of ARHGAP21 interacts with the carboxyl terminus of InsP3R to enhance $Ca^{2+}$ release from endoplasmic reticulum through InsP3R $Ca^{2+}$ channels. The interaction of ARHGAP21 with InsP3R regulates the formation of F-actin and HEK-293 cell migration. Therefore, we propose that estrogen binds to membrane associated ER to modulate ECM and cell migration through a c-Src-CDC42-ARHGAP21-InsP3R-integrin pathway (FIG. 12).

EGF binds to Her1, resulting in activation of the c-Src phosphorylation pathway to regulate cell proliferation and migration. Anordrin modulation of cell proliferation and migration has also been demonstrated to act through the c-Src pathway. We found that anordrin could block the stimulatory effects of EGF on cell migration in MDA-MB-231 cells and cell growth in T47D cells. When anordrin was used as an anti-tumor medicine in the 1990's, it was found to improve the quality of life and increase the lifespan of patients whose cancers were potentially caused by EGF/Her1 and failed to be inhibited by an EGF competitor. Our results suggest that anordrin can be used in anti-tumor therapies to treat those patients whose tumor growth is dependent on membrane-associated ER and the Her1-c-Src pathway.

GPER1 has been primarily considered to be linked to anti-estrogen resistance in reproductive cancers, since it was found to be involved in activation of MAPK/ERK and PI3K/AKT by estrogen through the EGFR pathway in ER-negative, but GPER1 positive, breast cancer cell lines (34). Subsequently, it was reported to be abundantly expressed in biopsy specimens of reproductive cancers from patients. Notably, GPER1 expression is associated with tumor size, ER-negative-her-2/neu, and extramammary metastases (35). However, reports showed that knockdown of GPER1 failed to correlate with ERK activity (36). The GPER1-selective agonist G1 also failed to exert an estrogenic effect in the uterus or mammary gland (37). Our results show that anordrin is a pure antagonist of membrane-associated ER and functions as a GPER1 agonist. In contrast, tamoxifen exhibits the opposite properties. Based on our results, combination of anordrin and tamoxifen can therefore minimize the side effects of tamoxifen.

Estrogen regulation of energy balance has been reported to be primarily mediated by ER-α. Knockout of ER-α has been shown to result in loss of estrogen modulation of obesity (39). 25% of GPER1 knockout mice have been shown to exhibit obesity (40). In contrast, ER-β knockout mice do not show increased rates of obesity (41). These results suggest that cross-talk between ER-α and GPER1 is important for the estrogen regulation of energy balance. GPER1 is predominantly localized to the endoplasmic reticulum, where estrogen and phosphatidylinositol 3, 4, 5-triphosphate ($IP_3$) signals are generated, leading to $Ca^{2+}$ release from InsP3R (5). White et al. reported that $Ca^{2+}$ release from InsP3R enhances the bioenergetics of mitochondria (42). In the present example, we found accumulation of lipid around the nucleus of liver cells in both ovariectomized (OVX) and tamoxifen-treated mice. Taken together, we predict that GPER1 agonists possibly enhance InsP3R activity to deliver $Ca^2$ from the endoplasmic reticulum to mitochondria, leading to enhanced mitochondrial metabolism of glucose to ATP.

Although GPER1 has been found to also localize to the plasma membrane, cross-talk between GPER1 and IL-IR complex has never been reported. On the other hand, estrogen-ER-α not only regulates Glut-4 expression and its translocation to cell membrane (43), it also cross-talks with IL-IR complex to regulate glucose uptake in MCF-7 and skeletal muscle cells (44, 45). Interestingly, tamoxifen was found to prevent osteoporosis during clinical usage. Anordrin was also found to prevent osteoporosis in our experiments (FIGS. 11A-11E).

Tamoxifen can enhance 2-NBDG uptake and inhibit ATP generation. The elevated intake of glucose caused by tamoxifen cannot be metabolized into APT. Consequently, excess glucose can be transformed into TG. This chain of events explains why tamoxifen can induce NASH when used for breast cancer therapy. On the other hand, when excessive amount of uptaken glucose cannot be metabolized, excessive amount of TG is stored up, leading to inhibition of further uptake of glucose even at the presence of high insulin concentrations. This scenario may explain why tamoxifen induces insulin resistance, and thereby increases the incidence of diabetes II. Anordrin or analog thereof (such as anordrin) can counteract the effects of tamoxifen on glucose uptake and glucose metabolism to ATP and TG. Therefore, combination of anordrin and tamoxifen can prevent tamoxifen-induced insulin resistance and incidence of diabetes II.

Materials and Methods

Plasmid construction, protein expression, purification and characterization by LC-MSMS: ER-α ligand binding domain and ER-α-36 were cloned into pGEX-6P-1 at EcoRI and XhoI sites. GST-ER fusion proteins were induced using 0.1 µM IPTG and expressed in *E. coli* at 25° C. for 3 hours. Bacteria were harvested. GST fusion proteins were purified following manufacturer's instructions. Purified protein on GST-beads was eluted using 1× sample buffer at 100° C. for 5 minutes. The supernant was run on 10% SDS-PAGE. Gel was stained using Coomassie blue-R250. Protein bands were cut and characterized by LC-MSMS. ER-α-36 and GPER1 cDNAs were purchased from YR gene and subcloned into pRetro-AcGFP and pQXIX-EGFP vectors, respectively (Clontech).

Cell culture, retrovirus packaging, cell sorting and construction of stable cell line and drug inhibition assay: MCF-7, T47D, MDA-MB-231, Hec-1A, CHO-K1 and HEK-293 cells were grown following ATCC protocol. The plasmids of pVSV-G protein cDNA with ER-α-36 or GPER1 cDNA were co-transfected into HEK-293 package cells. After 72 hours of transfection, supernatant was harvested and concentrated using ultracentrifugation at 25krpm for 2 hours. Virus was resuspensed using culture medium of stable cells. Cells were infected using virus at 37° C. for 2 hours, grown for 2 days and GFP-positive cells were seeded into 96well plates at one cell per well. The expression of GFP fusion protein was checked using western blotting.

Binding and competition assays: GST and GST-ER-α fusion proteins were expressed in *E. coli* and purified using glutathione beads. 2 µg/ml GST (40-80 nM) fusion proteins in 1 ml TE buffer was mixed with 1 nM $^3$H-E2 at 4° C. for 2 h. Radioactivity on beads was measured using a GM meter. HEK-293 cells were transfected to express GST fusion proteins of ER-β or GPER1. Cells were lysed in 1×TE buffer containing protease inhibitor cocktail (sigma) on ice for 30 min, 80% glycerol was added to reach 20% glycerol. Tubes were centrifuged at 300 g for 5 min and supernatant was collected. Protein concentration was measured by Bio-rad protein concentration assay kit. 100 nM anordrin and 1 nM $^3$H-E2 was added to 1 ml lysate (5 mg/ml total protein) at 4° C. for 2 h. Radioactivity on beads was measured using GM meter.

Isolation of microsome and Drug competition assay: Cells were harvested and lysed in TE buffer (50 mM Tris (pH8.0), 5 mM EDTA, 2 mM PMSF and protease inhibitor cocktail (Sigma)) for 30 min with vortexing every 5 min. 80% glycerol in TE buffer was added to cell lysates to reach 20% and centrifuged at 800 g for 5 min. The supernatant was transferred to new tubes and total protein concentration was adjusted to 5 mg/ml. Drugs and $^3$H-E2 were added to 1 ml protein solution and incubated at 4° C. for 2 hours. Microsome was precipitated at 25krpm for 2 hours. Bound $^3$H-E2 was measured using GM meter.

Drug inhibition assay: Cells were inoculated into 24 well plates and treated using the designated concentration of drugs. Cell number was counted using a cell counter (Count Star).

Transwell and flow cytometry assay: Cells were starved for 48 hours in phenol red free medium containing 5% charcoal-stripped FBS, and then changed into phenol red free medium for an additional 24 hours. Transwell was performed following the Chemicon kit instructions (CAT # ECM551). Briefly, cells were trypsinized, washed using 1×DPBS containing Ca2+ and Mg2+ (Sigma) and resuspensed in serum and phenol red free medium at a cell density of $0.5 \times 10^6$ cells/ml. 200 µl cell suspension containing drugs was added into the upper chamber and inserted into the lower chamber containing 0.5 ml medium with 10% FBS for 16 hours. Flow cytometry was performed by suspending cells in trypsin-free cell suspension buffer (Millipore), and labeling with FITC-antibody (millinpore) following company instructions.

The specific siRNAs against ER-α and GPER1 were designed according to references 46 and 47 respectively, and were synthesized by Genepharma Co., LTD.

Glucose concentration assay: glucose concentration in medium or total blood from mouse tail was measured using glucose assay kits following manufacturer's instructions (Yicheng, Beijing).

Construction of ovariectomized (OVX) mice model and administration of drugs: The ovaries of 6 week old mice were excised by surgery. 3 days post surgery drugs were administered by gastric tract injection every day or mixed with food.

Preparation of paraffin sections and HE staining: The tissue of mice was excised by surgery and fixed using 2.5% formaldehyde in 1×PBS. Paraffin section preparation and HE staining was performed following the standard protocol from GLP laboratory of BK animal model, Inc.

Measurement of TC and TG in liver and serum of mice: 30-50 mg of mouse liver was excised by surgery and homogenized in 1 ml Cholroform:Methanol (2:1) mixture and extracted using 0.5 ml $ddH_2O$. The organic phase was transferred to new tubes and air dried. The amount of TC and TG was measured using kits following manufacturer's instructions. The error was corrected by using internal standard controls.

Bone density assay using micro-CT: Thighbone was fixed in 1×DPBS containing 3% formaldehyde for two weeks. The fixation solution was exchanged after one week. The density of thighbone was measured by Siemens Inveon Micro-CT. Inveon Research Workplace (IRW) was used to analyze the HU2000 value at the following measurement conditions: 80KVP, 500 mA, 1500 ms exposure time; CCD Readout installation: 2048axial, 2048 binning; FOV Transaxial: 19.03 mm, axial: 19.03 mm, pixels size: 9.29 μm.

Extraction of cellular lysate, Western blotting, total RNA extraction and RT-qPCR: Cells were harvested and lysed in RIPA buffer or 1×DPBS containing 1% triton-x100 and protease inhibitor cocktail. Total protein concentration was measured using Bio-rad protein staining dye. Western blotting was performed following standard protocol using nitrocellulose membrane (Millipore) and Bio-rad semi-dry transfer system. Total RNA was extracted using RNA extract solution (sigma). RT-qPCR was performed using the Roche Sybr qPCR kit, ABI7900HT PCR machine using the program: 95° C. for 10 min followed by 40 cycles of 95° C. for 10 sec and 60° C. for 1 min.

Statistical analysis: In tables and figures, the results were presented as mean+STDEV. Asterisks indicate a statistically significant difference calculated using student's t-test, two-tailed.

Example 2. Binding Assays of Anordrin and Dinordrin

Dinordrin has a similar structure as anordrin except that it has an —H at R6 position. We found that 50 nM dinordrin blocked 63.2±5.7% of 0.5 nM [$H^3$-E2] binding to 1 μg of GST-ER-α-LBD on beads. By contrast, no inhibition by anordrin that blocks [$H^3$-E2] binding to 1 μg of GST-ER-α-LBD.

Further, 6 μM dinordrin increased Bcl-2 mRNA transcription for 147.2%±22.73% (P<0.001). By contrast, statistically non-significantly different by anordrin 3.18%±3.22% in MCF-7 cells was measured using RT-qPCR.

The results showed that the R6-$CH_3$ (as opposed to —H) is essential for the unique functional characteristics of anordrin.

Paraffin was removed from mouse liver sections using xylene. The liver sections were stained using antibodies against GPER1, ER-α or ER-β respectively.

REFERENCES

1. Boonyaratanakornkit, V., Steriods. 76, 877-884, (2011).
2. Mauvais-jarvis, F., Clegg, D J., and Hevener, A I., Endocrine Reviews. 34(3), 309-338 (2013)
3. Kuang, L G., Zhang, X T., Xie, Y., et al., Molecular endocrinology. 24(4), 709-721 (2010)
4. Rao, J., Jiang, X M., Wang, Y., and Chen, B. Journal of Steroid Biochemistry and Molecular Biology. 127, 231-237 (2011)
5. Revankar, C M., Cimno D., Sklar, L A., Arterburn, J B., and Prossnitz, E R. Science. 307 (11), 1625-1630 (2005)
6. Nilsson, B O., Olde, B., and Leeb-Lundberg, L F. British Journal of Pharmacology. 163. 1131-1139 (2011)
7. Zhang, X T., Ding, L., Kang, L G., and Wang, Y. PLos one. 7(1), e30174 (2012)
8. O'Brien, J E., Peterson, T J., Tong, M H., et al. J. of Biol. Chem. 281(36). 26683-26692 (2006)
9. Takamura, T., shimizu, A., Kumura, T., Ando, K Zen, Y., et al. Internal Med. 579-581 (2007)
10. Barrett-Connor, E., Mosca, L., Collins, P., et al. N Engl. J. Med. 355. 125-137 (2006)
11. Alexanderson, P., Toussaint, A., Christiansen, C., et al. JAMA. 285(11). 1482-8 (2001)
12. Hershberger, P A., Stabile, L P., Kanterewicz, B., et al. J. of Steroid Biochem. & Mol. Biol. 16. 102-9 (2009)
13. Bank, U. K. and Pincus, U., Proc. Soc. Expt. Biol. Med. 111, 595 (1962).
14. Pincus, U. and Gordon, H. L., Steroids, 5, 193, (1965).
15. Xu, B., Zhou, P. Q., and Yu, W. J., Tumor, 9, 197 (1989).
16. Ma, Z. C., Lou, L. G., Zhang, Z., and Bin, X, Acta Pharmacol. Sin, 21, 939 (2000).
17. Li R. L., Lee, D. Y., Cheng, Q. L., U.S. Pat. No. 5,001,120 (1991).
18. Mehta, R. R., Jenco, J. M., and Chatterton, R. T., Steroids, 38, 679 (1981).
19. Nehra, R., Riggins, R B., Shajahan, A N et al. FASEB J. 24(6). 2040-55 (2010)
20. Watanabe, T., Inoue, S., Hiroi, H., Orimo, A., et al. Mol. Cell. Biol. 18.442-9 (1998)
21. Butler, W B., Kelsey, S J., Castagna, M. and Blumberg, P M. Cancer Res. 41(1). 82-8 (1981)
22. Cesarone G, Garofalo C, Abrams M T, et al. J Cell Biochem. 98(2). 440-50 (2006)
23. Kang, L G., Zhang, X T., Xie, Y., Tu, Y P., et al. Mol. Endocrinol. 24(4). 709-21 (2010)
24. Zhang, J., Li, G., Li, Z., Yu, X., Zhang, H., et al. Steroids. 77(6). 666-73 (2012)
25. Melchiori, A., Mortarini, R., Carlone, S., et al. *Exp. Cell Res.,* 219, 233-242(1995).
26. Morini, M., Mottolese, M., Ferrari, N., Ghiorzo, F., et al. *Int. J. Cancer:* 87, 336-342(2000)
27. Garrido P, Morin J, Alonso A, González S, et al. Endocrinology. 154(6):1979-89 (2013)
28. Garris D R., and Garris, B L. Cell Tissue Res. 319 (2). 231-42 (2005)
29. Wang Q., Jiang, L., Wang, J. et al. Hepatology. 49. 1166-75 (2009)
30. Szatkowski C., Parys, J B., Quadid-Ahidouch, H., et al. Mol. Cancer. 9.156(2010)
31. Fukatsu K, Bannai H, Inoue T, Mikoshiba K. J Neurochem. 114(6):1720-33. (2010)
32. Cabodi, S., Moro, L., Baj, G., et al. J Cell Sci. 117. 1603-11 (2004)
33. Bigarella C L, Borges L, Costa F F, Saad S T. Biochim Biophys Acta. 1793(5):806-16. (2009)
34. Filardo E J, Quinn J A, Bland K I, Frackelton Jr. A R. Mol. Endocrinol. 14:1649-60 (2000)
35. Filardo E J, Graeber C T, Quinn J A et al. Clin. Cancer Res. 12:6359-66 (2006)
36. Pedram A, Razandi M, Levin E R. Mol. Endocrinol. 20: 1996-2009 (2006)

37. Otto C, Rohde-schuzl B, Schwarz GFuchs I, et al. Endocrinology. 149:4846-56 (2008)
38. Edward J, Filardo and Thomas P. Endocrinology. 153(7): 2953-62 (2012)
39. Geary, N., Asarian, L., Korach, K S et al. Endocrinology. 142, 4751-7 (2001)
40. Ohlsson, C., Hellberg, N., Parini, P. et al. Biochem. Biophys. Res. Commun. 278, 640-5 (2000)
41. Langer, G., Bader, B., Meoli, L., et al. Steroids. 75, 603-10 (2010)
42. White, C., Li, C., Yang, J., et al. Nat. Cell Biol. 7(10), 1021-8 (2005)
43. Muthusamy T, Murugesan P, Balasubramanian K. Metabolism. 58(11):1581-92 (2009)
44. Ceusta, P G., Suarez, J M., Garcia, A A. et al. Endocrinology. (2013)
45. Gorres, B K., Bomhoff, G L., Morris, J K., and Geiger, P C. J Physiol. (2013)
46. Foulstone E J, Zheng L, Perks C M, Holly J M. Endocrinology, 154 (5):1780-1793. (2013)
47. Luo H, Yang G, Yu T, Luo S, Wu C, Sun Y, Liu M, Tu G. Endocr. Relat. Cancer. 21(2): 355-69 (2014).

The invention claimed is:

1. A method of treating a cancer in an individual comprising administering to the individual an effective amount of an anordrin, wherein the cancer is ER-α-36 positive.

2. The method of claim 1, wherein the cancer is selected from the group consisting of breast cancer, lung cancer, pancreatic cancer, gastric cancer, colon cancer, liver cancer, endometrial cancer, and CLL.

3. The method of claim 1, further comprising administering to the individual an effective amount of at least one other agent selected from the group consisting of tamoxifen, or functional equivalent thereof, an EGFR inhibitor and a VEGFR inhibitor.

4. The method of claim 3, wherein the cancer is resistant to treatment with the other agent, wherein the other agent is not administered in combination with anordrin.

5. The method of claim 4, wherein the other agent is tamoxifen.

6. The method of claim 4, wherein the other agent is EGFR inhibitor.

7. The method of claim 4, wherein the other agent is VEGFR inhibitor.

8. The method according to claim 2, wherein the cancer is endometrial cancer, wherein the endometrial cancer is induced by tamoxifen, and wherein tamoxifen is not administered in combination with anordrin.

9. The method of claim 1, wherein the cancer is positive for membrane bound ER-α-36.

10. The method of claim 4, wherein the cancer is positive for membrane bound ER-α-36.

11. The method of claim 3, wherein the other agent and anordrin are administered sequentially, simultaneously or concurrently.

12. The method of claim 3, wherein the other agent and anordrin are formulated in a single pharmaceutical composition.

13. The method of claim 1, wherein the individual is a human.

* * * * *